United States Patent
Lansalot-Matras et al.

(10) Patent No.: US 9,499,571 B2
(45) Date of Patent: Nov. 22, 2016

(54) GERMANIUM- AND ZIRCONIUM-CONTAINING COMPOSITIONS FOR VAPOR DEPOSITION OF ZIRCONIUM-CONTAINING FILMS

(71) Applicant: L'Air Liquide, Société Anonyme pour l'Etude et l'Exploitation des Procédés Georges Claude, Paris (FR)

(72) Inventors: Clement Lansalot-Matras, Seoul (KR); Julien Lieffrig, Seoul (KR); Hana Ishii, Seoul (KR); Christian Dussarrat, Tokyo (JP)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 217 days.

(21) Appl. No.: 14/580,324

(22) Filed: Dec. 23, 2014

(65) Prior Publication Data
US 2015/0110958 A1    Apr. 23, 2015

(51) Int. Cl.
   *C23C 16/00*      (2006.01)
   *C07F 7/30*       (2006.01)
   (Continued)

(52) U.S. Cl.
   CPC ............. *C07F 7/30* (2013.01); *C07F 7/006* (2013.01); *C23C 16/40* (2013.01); *C23C 16/405* (2013.01); *C23C 16/45553* (2013.01)

(58) Field of Classification Search
   CPC ............. C23C 16/40; C23C 16/405; C23C 16/45553; C07F 7/30; C07F 7/006
   See application file for complete search history.

(56) References Cited

U.S. PATENT DOCUMENTS 4,931,417 A  *  6/1990  Miya et al. ............ C07F 17/00
                                                      502/117
5,527,752 A     6/1996  Reichle et al.
(Continued)

FOREIGN PATENT DOCUMENTS

EP    1 067 595    1/2001
EP    1 524 299    4/2005
(Continued)

OTHER PUBLICATIONS

Chung et al. Trimethylsilylcyclopentadienyl tris( dimethylamino )zirconium as a single-source metal precursor for the atomic layer deposition of Zr xSi 1-x04, Thin Solid Films, 564 (2014), pp. 140-145.*
(Continued)

*Primary Examiner* — Kelly M Gambetta
(74) *Attorney, Agent, or Firm* — Patricia E. McQueeney

(57) ABSTRACT

Disclosed are Germanium- and Zirconium-containing precursors having one of the following formulae:

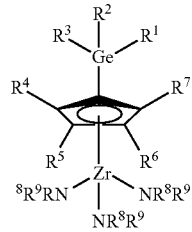

Formula I

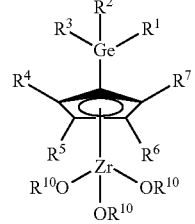

Formula II wherein each $R^1$, $R^2$, $R^3$, $R^4$, $R^5$, $R^6$, $R^7$, $R^8$, $R^9$ and $R^{10}$ is independently selected from H; a C1-C5 linear, branched, or cyclic alkyl group; and a C1-C5 linear, branched, or cyclic fluoroalkyl groups. Also disclosed are methods of synthesizing the disclosed precursors and using the same to deposit Zirconium-containing films on substrates via vapor deposition processes.

20 Claims, 2 Drawing Sheets

(51) Int. Cl.
  *C07F 7/00* (2006.01)
  *C23C 16/40* (2006.01)
  *C23C 16/455* (2006.01)

(56) References Cited

U.S. PATENT DOCUMENTS

| | | |
|---|---|---|
| 5,846,895 A | 12/1998 | Gila et al. |
| 5,861,352 A | 1/1999 | Gila et al. |
| 6,001,742 A | 12/1999 | Chang |
| 6,197,683 B1 | 3/2001 | Kang et al. |
| 6,268,448 B1 | 7/2001 | Collins et al. |
| 6,445,023 B1 | 9/2002 | Vaartstra et al. |
| 6,548,424 B2 | 4/2003 | Putkonen |
| 6,669,990 B2 | 12/2003 | Min et al. |
| 6,689,675 B1 | 2/2004 | Parker et al. |
| 6,743,473 B1 | 6/2004 | Parkhe et al. |
| 6,858,547 B2 | 2/2005 | Metzner et al. |
| 6,984,591 B1 | 1/2006 | Buchanan et al. |
| 7,108,747 B1 | 9/2006 | Leskela et al. |
| 2001/0001949 A1 | 5/2001 | Westmoreland et al. |
| 2004/0235312 A1 | 11/2004 | Loftin et al. |
| 2005/0056219 A1 | 3/2005 | Dip et al. |
| 2005/0260357 A1 | 11/2005 | Olsen et al. |
| 2006/0062917 A1 | 3/2006 | Muthukrishnan et al. |
| 2006/0097305 A1 | 5/2006 | Lee |
| 2006/0228888 A1 | 10/2006 | Lee et al. |
| 2008/0308793 A1 | 12/2008 | Jeong et al. |
| 2009/0203222 A1 | 8/2009 | Dussarrat et al. |
| 2009/0311879 A1 | 12/2009 | Blasco et al. |
| 2013/0208403 A1 | 8/2013 | Rocklein et al. |

FOREIGN PATENT DOCUMENTS

| | | |
|---|---|---|
| JP | 11 307519 | 11/1999 |
| JP | 2001 102326 | 4/2001 |
| JP | 2001 355070 | 12/2001 |
| JP | 2002 069641 | 3/2002 |
| JP | 2002 093803 | 3/2002 |
| JP | 2002 093804 | 3/2002 |
| JP | 2004 507551 | 3/2004 |
| JP | 2004 300579 | 10/2004 |
| JP | 2004 349710 | 12/2004 |
| JP | 2005 104994 | 4/2005 |
| JP | 2005 171291 | 6/2005 |
| JP | 2005 209766 | 8/2005 |
| KR | 2008 0101040 | 11/2008 |
| KR | 10 1284664 | 7/2012 |
| WO | WO 96 27032 | 9/1996 |
| WO | WO 97 49105 | 12/1997 |
| WO | WO 02/18394 | 3/2002 |
| WO | WO 2003 035926 | 5/2003 |
| WO | WO 2004 010469 | 1/2004 |
| WO | WO 2005 113852 | 12/2005 |
| WO | WO 2007 141059 | 6/2006 |
| WO | WO 2006 131751 | 12/2006 |
| WO | WO 2007 005088 | 1/2007 |
| WO | WO 2007 011973 | 1/2007 |
| WO | WO 2007 030673 | 3/2007 |
| WO | WO 2007 066546 | 6/2007 |
| WO | WO 2007 140813 | 12/2007 |
| WO | WO 2007 141059 | 12/2007 |
| WO | WO 2009 036046 | 3/2009 |
| WO | WO 2009 087609 | 7/2009 |
| WO | WO 2009 106433 | 9/2009 |
| WO | WO 2011 020042 | 2/2011 |

OTHER PUBLICATIONS

Ciruelo et al. Synthesis and reactivity of new silyl substituted monocyclopentadienyl zirconium complexes. X-ray molecular structure of [Zr{ η 5-C 5H4( SiMe2CH2Ph) }( CH2Ph) 3], J. Organometallic Chem, 547 (1997) pp. 287-296.*
Ciruelo, G. et al., "Synthesis and reactivity of new silyl substituted monocyclopenta-dienyl zirconium complexes. X-ray molecular structure of [Zr{η$^5$-C$_5$H$_4$(SiMe$_2$CH$_2$Ph)} (CH$_2$Ph)$_3$]," Journal of Organometallic Chemistry 547 (1997) 287-296.
Qian, X. et al., "Synthesis of new substituted cyclopentadienyl titanium monomethoxy-difluorides with BF$_3$•OEt$_2$ as fluorinating reagent and their use in syndiotactic polymerization of styrene," Journal of Organometallic Chemistry 689 (2004) 1503-1510.
International Search Report and Written Opinion for corresponding PCT/US2015/066434, Apr. 12, 2016.
Beachley, O. T., et al., "Reagents based on cyclopentadienyl derivatives of the Group 14 elements for the synthesis of indium(I) derivatives. Crystal and molecular structure of In(C5H4SiMe3)," Organometallics 1990, 9, 2488-2492.
Becker, J.S. et al., "Atomic layer deposition of hafnium and zirconium nitrides", Chem. Mater. 2004, 16, 3497-3501.
Boscherini, F., et al., "Atomic scale mechanism for the Ge-induced stabilization of the tetragonal, very high-k phase of ZrO2," Applied Physics Letters 99, 121909 (2011).
Burger, H., et al., "Titan-Stickstoff-Verbindungengen, Darstellung and Eigenschaften Substituierter Cyclopentadienyl-Titan-Dialkylamide," Journal of Organometallic Chemistry, 101 (1975) 295-306.
Cano, J. et al., "Neutral and cationic [bis(n1-amidosilyl)-n5-cyclopentadienyl]titanium and -zirconium complexes: synthesis, x-ray molecular structures and DFT calculations", Eur. J. lnorg. Chem. 2003 2463-2474.
Carta, G. et al., "Thermal properties of volatile organohafnium precursors for HfO$_2$ MOCVD processes," Electrochemical Society Proceedings vol. 2005-09, pp. 260-267.
Caymax, M. et al., "High-k materials for advanced gate stack dielectrics: a comparison of ALCVD and MOCVD as deposition technologies," 2003 Materials Research Society Symposium Proceedings, vol. 765, pp. 47-58.
Chandra, G. et al. "Amido-derivatives of metals and metalloids. Part VI. Reactions of titanium(IV), zirconium(IV), and hafnium(IV) amides with protic compounds," Journal of Chemical Society (A), 1968, pp. 1940-1945.
Chang, H.S. et al. "Electrical and physical properties of HfO$_2$ deposited via ALD using Hf(OtBu)$_4$ and ozone atop Al$_2$O$_3$," Electrochem. Solid-State Letters, 7 (6) F42-F44 (2004).
Ciruelo, G. et al., "Synthesis and reactivity of new silyl substituted monocyclopentadienyl zirconium complexes. X-ray molecular structure of [Zr(N$^5$-C$_5$H$_4$(SiMe$_2$CH$_2$Ph))(CH$_2$Ph)$_3$]", Journal of Organometallic Chemistry 547 (1997) 287-296.
Codato, S. et al. "MOCVD growth and characterization of ZrO$_2$ thin films obtained from unusual organo-zirconium precursors," Chemical Vapor Deposition, Wiley-VCH Verlag, Weinheim, Germany, vol. 11, No. 11, 1999, pp. 159-164.
Cotton, S.A. "Ti, Ar, Hf," Annu. Rep.Prog. Chem., Sect. A: Inorganic Chemistry, 1993, 90, pp. 119-130.
Gilmore, C. M., et al., "Stabilized zirconia-alumina thin films," J. Vac. Sci. Technol. A 4, 2598, Nov./Dec. 1986.
Hausmann, D.M. et al. "Atomic layer deposition of hafnium and zirconium oxide using metal amide precursors," Chem., Mater. 2002, 14, 4350-4353.
Herrmann, W.A. et al., "Volatile metal alkoxides according to the concept of donor functionalization," Angew. Chem. Int. Ed. Engl. 1995, 34, pp. 2187-2206.
Irigoyen, A.M. et al., Synthesis and characterization of chlorobis(dialkylamido) and alkylbis(dialkylamido) derivatives of [(n$^5$—C$_5$Me$_5$)MCl$_3$](M=Ti, Zr), Journal of Organometallic Chemistry, 494 (1995) 255-259.
Juppo, M. et al. "In situ mass spectrometry study on surface reactions in atomic layer deposition of Al$_2$O$_3$ thin films from trimethylaluminum and water," Langmuir 2000, 16, pp. 4034-4039.
Jutzi, P. et al., "Halbsandwich-Komplexe der Elemente Titan and Zirconium mit dem (Diisopropylaminoethyl) cyclopentadienyl-Ligand: Molekülstruktur von [(C$_5$H$_4$CH$_2$CH$_2$N(H)$^i$Pr$_2$)ZrCl$_3$]$^+$Cl$^-$•2CH$_3$OH", Journal of Organometallic Chemistyr 533 (1997), 237-245.
Kawahara, T. et al. "Effect of Hf source, oxidizing agents, and NH$_3$/Ar plasma on the properties of HfAlO$_x$ films prepared by atomic layer deposition," J. Appl. Phys., vol. 43, No. 7A, 2004, pp. 4129-4134.

(56) References Cited

OTHER PUBLICATIONS

Kim, M.-S. et al., "ALD analyses of HfCl4 + O3 and HfCl4 + H2O by mass spectroscopy," Electrochemical Society Proceedings vol. 2005-05, pp. 397-403.
Kittl, J.A., et al., "High-k dielectrics for future generation memory devices," Microelectronic Engineering 86 (2009) 1789-1795.
Kukli, K. et al., "Atomic layer deposition of hafnium dioxide films from 1-methoxy-2-methyl-2-propanolate complex of hafnium," Chem Mater. 2003, 15, pp. 1722-1727.
Kukli, K. et al., "Influence of growth temperature on properties of zirconium dioxide films grown by atomic layer deposition," Journal of Applied Physics, 2002, 92, p. 1833-1840.
Lehn, J.-S. et al., "New precursors for the DVD of zirconium and hafnium oxide films," Chem Vap. Deposition 2006, 12, pp. 280-284.
Miikkulainen, V. et al., "Crystallinity of inorganic films grown by atomic layer deposition: overview and general trends," Applied Physics Reviews (2012) Version 14-9-2012, 1-92.
Niinisto, J. et al "Development of novel processes for atomic layer deposition of high-k dielectrics", 72$^{nd}$ Annual Meeting of the DPG, Feb. 27, 2008, Berlin.
Niinisto, J. et al. "In situ quadrupole mass spectrometry study of atomic-layer deposition of $ZrO_2$ using $Cp_2Zr(CH_3)_2$ and water," Langmuir, 7321, 21, 2005.
Niinisto, J., et al., "Novel mixed alkylamido-cyclopentadienyl precursors for ALD of ZrO2 thin films," J. Mater. Chem., 2008, 18, 5243-5247.
Pinchart, A. et al., "Novel thermally-stable hafnium and zirconium ALD precursors", IEEE/SEMI Advanced Semiconductor Manufacturing Conference (ASMC) 2007.
Potter, R.J. et al., "Deposition of $HfO_2$, $Gd_2O_3$ and $PrO_x$ by liquid injection ALD techniques," Chem. Vap. Deposition 2005, 11, No. 3, pp. 159-169.
Putkonen, M. et al., "Organometallic precursors for atomic layer deposition," Top Organomet Chem, 2005, 9, pp. 125-145.
Putkonen, M. et al. "Zirconia thin films by atomic layer epitaxy. A comparative study on the use of novel precursors with ozone," J. Mater. Chem., 3141, 11, 2001.
Rie, K.-T. et al., "Plasma assisted CVD for low temperature coatings to improve the wear and corrosion resistance," Surface and Coatings Technology, 1996, 86-87, pp. 498-506.
Ritala, M. et al., "Atomic layer deposition," Ch. 2, Handbook of Thin Film Materials, H.S. Nalwa, ed., vol. 1, "Deposition and Processing of Thin Films," Academic Press, San Diego, CA, 2002.
Rogers, J.S. et al., "Fulvene to cyclopentadienyl conversion with homoleptic complexes of zirconium and hafnium", Organometallics 1999 18, 3976-3980.
Schneider, H. et al. "Immobilization of $\eta^5$-cyclopentadienyltris(dimethylamido)zirconium polymerization catalysts on a chlorosilane- and HMDS-modified mesoporous silica surface: A new concept for supporting metallocene amides towards heterogenous single-site-catalysts," Journal of Molecular Catalysts A; Chemical 170 (2001) pp. 127-141.
Senzaki, Y. Y et al. "Atomic layer deposition of hafnium oxide and hafnium silicate thin films using liquid precursors and ozone," J. Vac. Sci. Technol. A 22(4), Jul./Aug. 2004.
Tsoutsou, D., et al., "Stabilization of very high-k tetragonal phase in Ge-doped ZrO2 films grown by atomic oxygen beam deposition," J. Appl. Phys. 106, 024107 (2009).
Tsoutsou, D., et al., "Stabilization of a very high-k tetragonal ZrO2 phase by direct doping with germanium," Microelectronic Engineering 86 (2009) 1626-1628.
Triyoso, D.H. et al. "Physical and electrical characteristics of $HfO_2$ gate dielectrics deposited by ALD and MOCVD," J. Electrochem. Soc., 152 (3) G203-G209 (2005).
Vanderbilt, D., et al., "Structural and dielectric properties of crystalline and amorphous ZrO2," Thin Solid Films 486 (2005) 125-128.
Vollmerhaus, R. et al., "Synthesis and structure of Group 4 iminophosphonamide complexes," Organometallics, 2005, vol. 24, pp. 494-507.
Williams, P.A. et al., "Novel mononuclear alkoxide precursors for the MOCVD of ZrO2 and HfO2 thin films," Chem Vap. Deposition 2002, 8, No. 4, pp. 163-170.
Winter, C.H. et al., "Metallic materials deposition: metal-organic precursors," Encyclopedia of Inorganic Chemistry, 2006, John Wiley & Sons Ltd., DOI: 10.1002/ 0470862106.ia138.
Wu, Y-H., et al., "High density metal-insulator-metal capacitor based on Zr O 2 Al 2 O 3 Zr O 2 laminate dielectric," Applied Physics Letters 93, 033511 (2008).
International Search Report and Written Opinion for corresponding PCT/EP2007/052507, Oct. 31, 2007.
International Search Report and Written Opinion for related PCT/EP2006/062893, Sep. 27, 2007.
International Search Report and Written Opinion for related PCT/EP2009/051683, May 14, 2009.

\* cited by examiner

GERMANIUM- AND ZIRCONIUM-CONTAINING COMPOSITIONS FOR VAPOR DEPOSITION OF ZIRCONIUM-CONTAINING FILMS

TECHNICAL FIELD

Disclosed are Germanium- and Zirconium-containing precursors. Also disclosed are methods of synthesizing the disclosed precursors and using the same to deposit Zirconium-containing films on substrates via vapor deposition processes.

BACKGROUND

With the scaling down of semiconductor devices such as dynamic random access memory (DRAM), new materials with high dielectric constant are required. Indeed, in order to store a sufficient charge in a capacitor with a smaller surface area, capacitors with higher permittivity are needed. Among high-k dielectrics, Group 4 based materials, such as $HfO_2$ or $ZrO_2$, are very promising since their dielectric constant is higher than $SiO_2$ or $Al_2O_3$. However, their dielectric constant varies depending on their crystalline form (Thin Solid Films 486 (2005) 125-128).

Thick $ZrO_2$ layers tend to have a unstable crystalline phase and to have higher leakage current (Applied Physics Reviews (2012) version 14-9-2012). To prevent these defects, a thin layer of $Al_2O_3$ has been introduced in between two layers of $ZrO_2$, forming a so-called ZAZ capacitor, stabilizing the crystalline phase and reducing the leakage current (Applied Physics Letters 93, 033511 (2008); J. Vac. Sci. Techno. A 4 (6), 1986; Microelectronic Engineering 86 (2009) 1789-1795).

The cubic/tetragonal crystalline phase of the $ZrO_2$ layer, which is the phase having the highest k-value, has also been stabilized by doping $ZrO_2$ with a small amount of silicon or germanium (US2013/0208403A1 for silicon and Journal of Applied Physics, 2009, 106, 024107; Microelectronic Engineering, 2009, 86, 1626; Applied Physics Letters, 2011, 99, 121909 for germanium).

Group 4 alkylamide precursors containing cyclopentadienyl ligands have been developed, such as the one show below (Dussarrat et al., WO2007/141059; Niinisto et al., Journal of Materials Chemistry (2008), 18(43), 5243-5247). These precursors show a higher thermal stability in comparison to tetrakis alkylamide precursors.

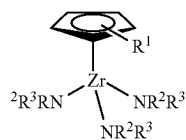

wherein $R^1$ = H, Me, or Et; $R^2$ & $R^3$ = $C_1$-$C_4$ alkyl group

Similar to these compounds, a few germylcyclopentadienyl Group 4 compounds have been reported such as (trimethylgermyl)cyclopentadienyl tris(dimethylamino) Titanium(IV) (Journal of Organometallic Chemistry, 1975, 101, 295).

A need remains for developing novel, liquid or low melting point (<50° C.), highly thermally stable, with low viscosity, zirconium precursor molecules suitable for vapor phase thin film deposition with controlled thickness and composition at high temperature.

SUMMARY

Disclosed are Germanium- and Zirconium-film forming compositions comprising a Germanium- and Zirconium-containing precursor having the following formula:

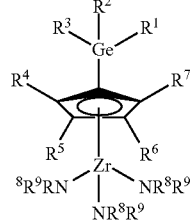

Formula I

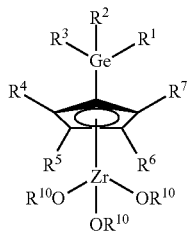

Formula II wherein each $R^1$, $R^2$, $R^3$, $R^4$, $R^5$, $R^6$, $R^7$, $R^8$, $R^9$ and $R^{10}$ is independently selected from H; a C1-C5 linear, branched, or cyclic alkyl group; or a C1-C5 linear, branched, or cyclic fluoroalkyl group. $R^1$, $R^2$ and $R^3$ may be identical or different. $R^4$, $R^5$, $R^6$ and $R^7$ may be identical or different. $R^8$ and $R^9$ may be identical or different. The disclosed Germanium- and Zirconium-film forming compositions may further include one or more of the following aspects:
- Each $R^1$ and $R^2$ and $R^3$ being independently selected from H, F, $CF_3$, Me, Et, nPr, iPr, nBu, iBu, sBu or tBu;
- Each $R^4$, $R^5$, $R^6$ and $R^7$ being independently selected from H, F, $CF_3$, Me, Et, nPr, iPr, nBu, iBu, sBu or tBu;
- Each $R^8$ and $R^9$ being independently selected from H, Me, Et, nPr, iPr, nBu, iBu, sBu or tBu;
- Each $R^{10}$ being Me, Et, nPr, iPr, nBu, iBu, sBu, or tBu;
- the Germanium- and Zirconium-containing precursor being (trimethylgermyl)cyclopentadienyl tris(Dimethylamino) Zirconium(IV) (Zr(TMG-Cp)(NMe$_2$)$_3$);
- the Germanium- and Zirconium-containing precursor being (trimethylgermyl)cyclopentadienyl tris(methylamino) Zirconium(IV) (Zr(TMG-Cp)(NHMe)$_3$);
- the Germanium- and Zirconium-containing precursor being (trimethylgermyl)cyclopentadienyl tris(Diethylamino) Zirconium(IV) (Zr(TMG-Cp)(NEt$_2$)$_3$);
- the Germanium- and Zirconium-containing precursor being (trimethylgermyl)cyclopentadienyl tris(ethylamino) Zirconium(IV) (Zr(TMG-Cp)(NHEt)$_3$);
- the Germanium- and Zirconium-containing precursor being (trimethylgermyl)cyclopentadienyl tris(ethylmethylamino) Zirconium(IV) (Zr(TMG-Cp)(NEtMe)$_3$);
- the Germanium- and Zirconium-containing precursor being (trimethylgermyl)cyclopentadienyl tris(Di n-propylamino) Zirconium(IV) (Zr(TMG-Cp)(NnPr$_2$)$_3$);
- the Germanium- and Zirconium-containing precursor being (trimethylgermyl)cyclopentadienyl tris(n-propylamino) Zirconium(IV) (Zr(TMG-Cp)(NHnPr)$_3$);

the Germanium- and Zirconium-containing precursor being (trimethylgermyl)cyclopentadienyl tris(Diisopropylamino) Zirconium(IV) (Zr(TMG-Cp)(NiPr$_2$)$_3$);
the Germanium- and Zirconium-containing precursor being (trimethylgermyl)cyclopentadienyl tris(isopropylamino) Zirconium(IV) (Zr(TMG-Cp)(NHiPr)$_3$);
the Germanium- and Zirconium-containing precursor being (trimethylgermyl)cyclopentadienyl tris(Di n-butylamino) Zirconium(IV) (Zr(TMG-Cp)(NnBu$_2$)$_3$);
the Germanium- and Zirconium-containing precursor being (trimethylgermyl)cyclopentadienyl tris(n-butylamino) Zirconium(IV) (Zr(TMG-Cp)(NHnBu)$_3$);
the Germanium- and Zirconium-containing precursor being (trimethylgermyl)cyclopentadienyl tris(Di isobutylamino) Zirconium(IV) (Zr(TMG-Cp)(NiBu$_2$)$_3$);
the Germanium- and Zirconium-containing precursor being (trimethylgermyl)cyclopentadienyl tris(isobutylamino) Zirconium(IV) (Zr(TMG-Cp)(NHiBu)$_3$);
the Germanium- and Zirconium-containing precursor being (trimethylgermyl)cyclopentadienyl tris(Di sec-butylamino) Zirconium(IV) (Zr(TMG-Cp)(NsBu$_2$)$_3$);
the Germanium- and Zirconium-containing precursor being (trimethylgermyl)cyclopentadienyl tris(sec-butylamino) Zirconium(IV) (Zr(TMG-Cp)(NHsBu)$_3$);
the Germanium- and Zirconium-containing precursor being (trimethylgermyl)cyclopentadienyl tris(Di tert-butylamino) Zirconium(IV) (Zr(TMG-Cp)(NtBu$_2$)$_3$);
the Germanium- and Zirconium-containing precursor being (trimethylgermyl)cyclopentadienyl tris(tert-butylamino) Zirconium(IV) (Zr(TMG-Cp)(NHtBu)$_3$);
the Germanium- and Zirconium-containing precursor being (trimethylgermyl)cyclopentadienyl tris(methoxy)Zirconium(IV) (Zr(TMG-Cp)(OMe)$_3$);
the Germanium- and Zirconium-containing precursor being (trimethylgermyl)cyclopentadienyl tris(ethoxy) Zirconium(IV) (Zr(TMG-Cp)(OEt)$_3$);
the Germanium- and Zirconium-containing precursor being (trimethylgermyl)cyclopentadienyl tris(n-propoxy)Zirconium(IV) (Zr(TMG-Cp)(OnPr)$_3$);
the Germanium- and Zirconium-containing precursor being (trimethylgermyl)cyclopentadienyl tris(isopropoxy) Zirconium(IV) (Zr(TMG-Cp)(OiPr)$_3$);
the Germanium- and Zirconium-containing precursor being (trimethylgermyl)cyclopentadienyl tris(tert-butoxy) Zirconium(IV) (Zr(TMG-Cp)(OtBu)$_3$);
the Germanium- and Zirconium-containing precursor being (trimethylgermyl)cyclopentadienyl tris(sec-butoxy) Zirconium(IV) (Zr(TMG-Cp)(OsBu)$_3$);
the Germanium- and Zirconium-containing precursor being (trimethylgermyl)cyclopentadienyl tris(n-butoxy)Zirconium(IV) (Zr(TMG-Cp)(OnBu)$_3$);
the Germanium- and Zirconium-containing precursor being (trimethylgermyl)cyclopentadienyl tris(iso-butoxy) Zirconium(IV) (Zr(TMG-Cp)(OiBu)$_3$);
the Germanium- and Zirconium-containing precursor being (dimethylgermyl)cyclopentadienyl tris(Dimethylamino) Zirconium(IV) (Zr(DMG-Cp)(NMe$_2$)$_3$);
the Germanium- and Zirconium-containing precursor being (dimethylgermyl)cyclopentadienyl tris(methylamino) Zirconium(IV) (Zr(DMG-Cp)(NHMe)$_3$);
the Germanium- and Zirconium-containing precursor being (dimethylgermyl)cyclopentadienyl tris(Diethylamino) Zirconium(IV) (Zr(DMG-Cp)(NEt$_2$)$_3$);
the Germanium- and Zirconium-containing precursor being (dimethylgermyl)cyclopentadienyl tris(ethylamino) Zirconium(IV) (Zr(DMG-Cp)(NHEt)$_3$);
the Germanium- and Zirconium-containing precursor being (dimethylgermyl)cyclopentadienyl tris(ethylmethylamino) Zirconium(IV) (Zr(DMG-Cp)(NEtMe)$_3$);
the Germanium- and Zirconium-containing precursor being (dimethylgermyl)cyclopentadienyl tris(Di n-propylamino) Zirconium(IV) (Zr(DMG-Cp)(NnPr$_2$)$_3$);
the Germanium- and Zirconium-containing precursor being (dimethylgermyl)cyclopentadienyl tris(n-propylamino) Zirconium(IV) (Zr(DMG-Cp)(NHnPr)$_3$);
the Germanium- and Zirconium-containing precursor being (dimethylgermyl)cyclopentadienyl tris(Diisopropylamino) Zirconium(IV) (Zr(DMG-Cp)(NiPr$_2$)$_3$);
the Germanium- and Zirconium-containing precursor being (dimethylgermyl)cyclopentadienyl tris(isopropylamino) Zirconium(IV) (Zr(DMG-Cp)(NHiPr)$_3$);
the Germanium- and Zirconium-containing precursor being (dimethylgermyl)cyclopentadienyl tris(Di n-butylamino) Zirconium(IV) (Zr(DMG-Cp)(NnBu$_2$)$_3$);
the Germanium- and Zirconium-containing precursor being (dimethylgermyl)cyclopentadienyl tris(n-butylamino) Zirconium(IV) (Zr(DMG-Cp)(NHnBu)$_3$);
the Germanium- and Zirconium-containing precursor being (dimethylgermyl)cyclopentadienyl tris(Di isobutylamino) Zirconium(IV) (Zr(DMG-Cp)(NiBu$_2$)$_3$);
the Germanium- and Zirconium-containing precursor being (dimethylgermyl)cyclopentadienyl tris(isobutylamino) Zirconium(IV) (Zr(DMG-Cp)(NHiBu)$_3$);
the Germanium- and Zirconium-containing precursor being (dimethylgermyl)cyclopentadienyl tris(Di sec-butylamino) Zirconium(IV) (Zr(DMG-Cp)(NsBu$_2$)$_3$);
the Germanium- and Zirconium-containing precursor being (dimethylgermyl)cyclopentadienyl tris(sec-butylamino) Zirconium(IV) (Zr(DMG-Cp)(NHsBu)$_3$);
the Germanium- and Zirconium-containing precursor being (dimethylgermyl)cyclopentadienyl tris(Di tert-butylamino) Zirconium(IV) (Zr(DMG-Cp)(NtBu$_2$)$_3$);
the Germanium- and Zirconium-containing precursor being (dimethylgermyl)cyclopentadienyl tris(tert-butylamino) Zirconium(IV) (Zr(DMG-Cp)(NHtBu)$_3$);
the Germanium- and Zirconium-containing precursor being (dimethylgermyl)cyclopentadienyl tris(methoxy) Zirconium(IV) (Zr(DMG-Cp)(OMe)$_3$);
the Germanium- and Zirconium-containing precursor being (dimethylgermyl)cyclopentadienyl tris(ethoxy) Zirconium(IV) (Zr(DMG-Cp)(OEt)$_3$);
the Germanium- and Zirconium-containing precursor being (dimethylgermyl)cyclopentadienyl tris(n-propoxy)Zirconium(IV) (Zr(DMG-Cp)(OnPr)$_3$);
the Germanium- and Zirconium-containing precursor being (dimethylgermyl)cyclopentadienyl tris(isopropoxy) Zirconium(IV) (Zr(DMG-Cp)(OiPr)$_3$);
the Germanium- and Zirconium-containing precursor being (dimethylgermyl)cyclopentadienyl tris(tert-butoxy) Zirconium(IV) (Zr(DMG-Cp)(OtBu)$_3$);
the Germanium- and Zirconium-containing precursor being (dimethylgermyl)cyclopentadienyl tris(sec-butoxy) Zirconium(IV) (Zr(DMG-Cp)(OsBu)$_3$);
the Germanium- and Zirconium-containing precursor being (dimethylgermyl)cyclopentadienyl tris(n-butoxy)Zirconium(IV) (Zr(DMG-Cp)(OnBu)$_3$);
the Germanium- and Zirconium-containing precursor being (dimethylgermyl)cyclopentadienyl tris(isobutoxy)Zirconium(IV) (Zr(DMG-Cp)(OiBu)$_3$);
the Germanium- and Zirconium-containing precursor being (trifluorogermyl)cyclopentadienyl tris(Dimethylamino) Zirconium(IV) (Zr(F$_3$Ge-Cp)(NMe$_2$)$_3$);

the Germanium- and Zirconium-containing precursor being (trifluorogermyl)cyclopentadienyl tris(methylamino) Zirconium(IV) (Zr(F$_3$Ge-Cp)(NHMe)$_3$);

the Germanium- and Zirconium-containing precursor being (trifluorogermyl)cyclopentadienyl tris(Diethylamino) Zirconium(IV) (Zr(F$_3$Ge-Cp)(NEt$_2$)$_3$);

the Germanium- and Zirconium-containing precursor being (trifluorogermyl)cyclopentadienyl tris(ethylamino)Zirconium(IV) (Zr(F$_3$Ge-Cp)(NHEt)$_3$);

the Germanium- and Zirconium-containing precursor being (trifluorogermyl)cyclopentadienyl tris(Ethylmethylamino) Zirconium(IV) (Zr(F$_3$Ge-Cp)(NEtMe)$_3$);

the Germanium- and Zirconium-containing precursor being (trifluorogermyl)cyclopentadienyl tris(Di n-propylamino) Zirconium(IV) (Zr(F$_3$Ge-Cp)(NnPr$_2$)$_3$);

the Germanium- and Zirconium-containing precursor being (trifluorogermyl)cyclopentadienyl tris(n-propylamino) Zirconium(IV) (Zr(F$_3$Ge-Cp)(NHnPr)$_3$);

the Germanium- and Zirconium-containing precursor being (trifluorogermyl)cyclopentadienyl tris(Diisopropylamino) Zirconium(IV) (Zr(F$_3$Ge-Cp)(NiPr$_2$)$_3$);

the Germanium- and Zirconium-containing precursor being (trifluorogermyl)cyclopentadienyl tris(isopropylamino) Zirconium(IV) (Zr(F$_3$Ge-Cp)(NHiPr)$_3$);

the Germanium- and Zirconium-containing precursor being (trifluorogermyl)cyclopentadienyl tris(Di n-butylamino) Zirconium(IV) (Zr(F$_3$Ge-Cp)(NnBu$_2$)$_3$);

the Germanium- and Zirconium-containing precursor being (trifluorogermyl)cyclopentadienyl tris(n-butylamino) Zirconium(IV) (Zr(F$_3$Ge-Cp)(NHnBu)$_3$);

the Germanium- and Zirconium-containing precursor being (trifluorogermyl)cyclopentadienyl tris(Di isobutylamino) Zirconium(IV) (Zr(F$_3$Ge-Cp)(NiBu$_2$)$_3$);

the Germanium- and Zirconium-containing precursor being (trifluorogermyl)cyclopentadienyl tris(isobutylamino) Zirconium(IV) (Zr(F$_3$Ge-Cp)(NHiBu)$_3$);

the Germanium- and Zirconium-containing precursor being (trifluorogermyl)cyclopentadienyl tris(Di sec-butylamino) Zirconium(IV) (Zr(F$_3$Ge-Cp)(NsBu$_2$)$_3$);

the Germanium- and Zirconium-containing precursor being (trifluorogermyl)cyclopentadienyl tris(sec-butylamino) Zirconium(IV) (Zr(F$_3$Ge-Cp)(NHsBu)$_3$);

the Germanium- and Zirconium-containing precursor being (trifluorogermyl)cyclopentadienyl tris(Di tert-butylamino) Zirconium(IV) (Zr(F$_3$Ge-Cp)(NtBu$_2$)$_3$);

the Germanium- and Zirconium-containing precursor being (trifluorogermyl)cyclopentadienyl tris(tert-butylamino) Zirconium(IV) (Zr(F$_3$Ge-Cp)(NHtBu)$_3$);

the Germanium- and Zirconium-containing precursor being (trifluorogermyl)cyclopentadienyl tris(methoxy)Zirconium(IV) (Zr(F$_3$Ge-Cp)(OMe)$_3$);

the Germanium- and Zirconium-containing precursor being (trifluorogermyl)cyclopentadienyl tris(ethoxy)Zirconium(IV) (Zr(F$_3$Ge-Cp)(OEt)$_3$);

the Germanium- and Zirconium-containing precursor being (trifluorogermyl)cyclopentadienyl tris(n-propoxy)Zirconium(IV) (Zr(F$_3$Ge-Cp)(OnPr)$_3$);

the Germanium- and Zirconium-containing precursor being (trifluorogermyl)cyclopentadienyl tris(iso-propoxy)Zirconium(IV) (Zr(F$_3$Ge-Cp)(OiPr)$_3$);

the Germanium- and Zirconium-containing precursor being (trifluorogermyl)cyclopentadienyl tris(tert-butoxy)Zirconium(IV) (Zr(F$_3$Ge-Cp)(OtBu)$_3$);

the Germanium- and Zirconium-containing precursor being (trifluorogermyl)cyclopentadienyl tris(sec-butoxy)Zirconium(IV) (Zr(F$_3$Ge-Cp)(OsBu)$_3$);

the Germanium- and Zirconium-containing precursor being (trifluorogermyl)cyclopentadienyl tris(n-butoxy) Zirconium(IV) (Zr(F$_3$Ge-Cp)(OnBu)$_3$);

the Germanium- and Zirconium-containing precursor being (trifluorogermyl)cyclopentadienyl tris(isobutoxy)Zirconium(IV) (Zr(F$_3$Ge-Cp)(OiBu)$_3$);

the Germanium- and Zirconium-containing precursor being (difluorogermyl)cyclopentadienyl tris(Dimethylamino) Zirconium(IV) (Zr(F$_2$HGe-Cp)(NMe$_2$)$_3$);

the Germanium- and Zirconium-containing precursor being (difluorogermyl)cyclopentadienyl tris(methylamino) Zirconium(IV) (Zr(F$_2$HGe-Cp)(NHMe)$_3$);

the Germanium- and Zirconium-containing precursor being (difluorogermyl)cyclopentadienyl tris(Diethylamino) Zirconium(IV) (Zr(F$_2$HGe-Cp)(NEt$_2$)$_3$);

the Germanium- and Zirconium-containing precursor being (difluorogermyl)cyclopentadienyl tris(ethylamino)Zirconium(IV) (Zr(F$_2$HGe-Cp)(NHEO$_3$);

the Germanium- and Zirconium-containing precursor being (difluorogermyl)cyclopentadienyl tris(Ethylmethylamino) Zirconium(IV) (Zr(F$_2$HGe-Cp)(NEtMe)$_3$);

the Germanium- and Zirconium-containing precursor being (difluorogermyl)cyclopentadienyl tris(Di n-propylamino) Zirconium(IV) (Zr(F$_2$HGe-Cp)(NnPr$_2$)$_3$);

the Germanium- and Zirconium-containing precursor being (difluorogermyl)cyclopentadienyl tris(n-propylamino) Zirconium(IV) (Zr(F$_2$HGe-Cp)(NHnPr)$_3$);

the Germanium- and Zirconium-containing precursor being (difluorogermyl)cyclopentadienyl tris(Diisopropylamino) Zirconium(IV) (Zr(F$_2$HGe-Cp)(NiPr$_2$)$_3$);

the Germanium- and Zirconium-containing precursor being (difluorogermyl)cyclopentadienyl tris(isopropylamino) Zirconium(IV) (Zr(F$_2$HGe-Cp)(NHiPr)$_3$);

the Germanium- and Zirconium-containing precursor being (difluorogermyl)cyclopentadienyl tris(Di n-butylamino) Zirconium(IV) (Zr(F$_2$HGe-Cp)(NnBu$_2$)$_3$);

the Germanium- and Zirconium-containing precursor being (difluorogermyl)cyclopentadienyl tris(n-butylamino) Zirconium(IV) (Zr(F$_2$HGe-Cp)(NHnBu)$_3$);

the Germanium- and Zirconium-containing precursor being (difluorogermyl)cyclopentadienyl tris(Di isobutylamino) Zirconium(IV) (Zr(F$_2$HGe-Cp)(NiBu$_2$)$_3$);

the Germanium- and Zirconium-containing precursor being (difluorogermyl)cyclopentadienyl tris(isobutylamino) Zirconium(IV) (Zr(F$_2$HGe-Cp)(NHiBu)$_3$);

the Germanium- and Zirconium-containing precursor being (difluorogermyl)cyclopentadienyl tris(Di sec-butylamino) Zirconium(IV) (Zr(F$_2$HGe-Cp)(NsBu$_2$)$_3$);

the Germanium- and Zirconium-containing precursor being (difluorogermyl)cyclopentadienyl tris(sec-butylamino) Zirconium(IV) (Zr(F$_2$HGe-Cp)(NHsBO$_3$);

the Germanium- and Zirconium-containing precursor being (difluorogermyl)cyclopentadienyl tris(Di tert-butylamino) Zirconium(IV) (Zr(F$_2$HGe-Cp)(NtBu$_2$)$_3$);

the Germanium- and Zirconium-containing precursor being (difluorogermyl)cyclopentadienyl tris(tert-butylamino) Zirconium(IV) (Zr(F$_2$HGe-Cp)(NHtBu)$_3$);

the Germanium- and Zirconium-containing precursor being (difluorogermyl)cyclopentadienyl tris(methoxy) Zirconium(IV) (Zr(F$_2$HGe-Cp)(OMe)$_3$);

the Germanium- and Zirconium-containing precursor being (difluorogermyl)cyclopentadienyl tris(ethoxy) Zirconium(IV) (Zr(F$_2$HGe-Cp)(OEt)$_3$);

the Germanium- and Zirconium-containing precursor being (difluorogermyl)cyclopentadienyl tris(n-propoxy)Zirconium(IV) (Zr(F$_2$HGe-Cp)(OnPr)$_3$);

the Germanium- and Zirconium-containing precursor being (difluorogermyl)cyclopentadienyl tris(isopropoxy)Zirconium(IV) (Zr(F$_2$HGe-Cp)(OiPr)$_3$);

the Germanium- and Zirconium-containing precursor being (difluorogermyl)cyclopentadienyl tris(tert-butoxy)Zirconium(IV) (Zr(F$_2$HGe-Cp)(OtBu)$_3$);

the Germanium- and Zirconium-containing precursor being (difluorogermyl)cyclopentadienyl tris(sec-butoxy)Zirconium(IV) (Zr(F$_2$HGe-Cp)(OsBu)$_3$);

the Germanium- and Zirconium-containing precursor being (difluorogermyl)cyclopentadienyl tris(n-butoxy) Zirconium(IV) (Zr(F$_2$HGe-Cp)(OnBu)$_3$);

the Germanium- and Zirconium-containing precursor being (difluorogermyl)cyclopentadienyl tris(isobutoxy)Zirconium(IV) (Zr(F$_2$HGe-Cp)(OiBu)$_3$);

the Germanium- and Zirconium-containing precursor being (monofluorogermyl)cyclopentadienyl tris(Dimethylamino) Zirconium(IV) (Zr(FH$_2$Ge-Cp)(NMe$_2$)$_3$);

the Germanium- and Zirconium-containing precursor being (monofluorogermyl)cyclopentadienyl tris(methylamino) Zirconium(IV) (Zr(FH$_2$Ge-Cp)(NHMe)$_3$);

the Germanium- and Zirconium-containing precursor being (monofluorogermyl)cyclopentadienyl tris(Diethylamino) Zirconium(IV) (Zr(FH$_2$Ge-Cp)(NEt$_2$)$_3$);

the Germanium- and Zirconium-containing precursor being (monofluorogermyl)cyclopentadienyl tris(ethylamino) Zirconium(IV) (Zr(FH$_2$Ge-Cp)(NHEt)$_3$);

the Germanium- and Zirconium-containing precursor being (monofluorogermyl)cyclopentadienyl tris(Ethylmethylamino) Zirconium(IV) (Zr(FH$_2$Ge-Cp)(NEtMe)$_3$);

the Germanium- and Zirconium-containing precursor being (monofluorogermyl)cyclopentadienyl tris(Di n-propylamino) Zirconium(IV) (Zr(FH$_2$Ge-Cp)(NnPr$_2$)$_3$);

the Germanium- and Zirconium-containing precursor being (monofluorogermyl)cyclopentadienyl tris(n-propylamino) Zirconium(IV) (Zr(FH$_2$Ge-Cp)(NHnPr)$_3$);

the Germanium- and Zirconium-containing precursor being (monofluorogermyl)cyclopentadienyl tris(Diisopropylamino) Zirconium(IV) (Zr(FH$_2$Ge-Cp)(NiPr$_2$)$_3$);

the Germanium- and Zirconium-containing precursor being (monofluorogermyl)cyclopentadienyl tris(isopropylamino) Zirconium(IV) (Zr(FH$_2$Ge-Cp)(NHiPr)$_3$);

the Germanium- and Zirconium-containing precursor being (monofluorogermyl)cyclopentadienyl tris(Di n-butylamino) Zirconium(IV) (Zr(FH$_2$Ge-Cp)(NnBu$_2$)$_3$);

the Germanium- and Zirconium-containing precursor being (monofluorogermyl)cyclopentadienyl tris(n-butylamino) Zirconium(IV) (Zr(FH$_2$Ge-Cp)(NHnBu)$_3$);

the Germanium- and Zirconium-containing precursor being (monofluorogermyl)cyclopentadienyl tris(Di isobutylamino) Zirconium(IV) (Zr(FH$_2$Ge-Cp)(NiBu$_2$)$_3$);

the Germanium- and Zirconium-containing precursor being (monofluorogermyl)cyclopentadienyl tris(isobutylamino)Zirconium(IV) (Zr(FH$_2$Ge-Cp)(NHiBu)$_3$);

the Germanium- and Zirconium-containing precursor being (monofluorogermyl)cyclopentadienyl tris(Di sec-butylamino) Zirconium(IV) (Zr(FH$_2$Ge-Cp)(NsBu$_2$)$_3$);

the Germanium- and Zirconium-containing precursor being (monofluorogermyl)cyclopentadienyl tris(sec-butylamino) Zirconium(IV) (Zr(FH$_2$Ge-Cp)(NHsBu)$_3$);

the Germanium- and Zirconium-containing precursor being (monofluorogermyl)cyclopentadienyl tris(Di tert-butylamino) Zirconium(IV) (Zr(FH$_2$Ge-Cp)(NtBu$_2$)$_3$);

the Germanium- and Zirconium-containing precursor being (monofluorogermyl)cyclopentadienyl tris(tert-butylamino) Zirconium(IV) (Zr(FH$_2$Ge-Cp)(NHtBu)$_3$);

the Germanium- and Zirconium-containing precursor being (monofluorogermyl)cyclopentadienyl tris (methoxy) Zirconium(IV) (Zr(FH$_2$Ge-Cp)(OMe)$_3$);

the Germanium- and Zirconium-containing precursor being (monofluorogermyl)cyclopentadienyl tris (ethoxy)Zirconium(IV) (Zr(FH$_2$Ge-Cp)(OEt)$_3$);

the Germanium- and Zirconium-containing precursor being (monofluorogermyl)cyclopentadienyl tris(n-propoxy) Zirconium(IV) (Zr(FH$_2$Ge-Cp)(OnPr)$_3$);

the Germanium- and Zirconium-containing precursor being (monofluorogermyl)cyclopentadienyl tris(isopropoxy) Zirconium(IV) (Zr(FH$_2$Ge-Cp)(OiPr)$_3$);

the Germanium- and Zirconium-containing precursor being (monofluorogermyl)cyclopentadienyl tris(tert-butoxy) Zirconium(IV) (Zr(FH$_2$Ge-Cp)(OtBu)$_3$);

the Germanium- and Zirconium-containing precursor being (monofluorogermyl)cyclopentadienyl tris(sec-butoxy) Zirconium(IV) (Zr(FH$_2$Ge-Cp)(OsBu)$_3$);

the Germanium- and Zirconium-containing precursor being (monofluorogermyl)cyclopentadienyl tris(n-butoxy) Zirconium(IV) (Zr(FH$_2$Ge-Cp)(OnBu)$_3$);

the Germanium- and Zirconium-containing precursor being (monofluorogermyl)cyclopentadienyl tris(isobutoxy) Zirconium(IV) (Zr(FH$_2$Ge-Cp)(OiBu)$_3$);

the Germanium- and Zirconium-containing precursor being (fluoro dimethylgermyl)cyclopentadienyl tris (Dimethylamino) Zirconium(IV) (Zr(FMe$_2$Ge-Cp)(NMe$_2$)$_3$);

the Germanium- and Zirconium-containing precursor being (fluoro dimethylgermyl)cyclopentadienyl tris(methylamino) Zirconium(IV) (Zr(FMe$_2$Ge-Cp)(NHMe)$_3$);

the Germanium- and Zirconium-containing precursor being (fluoro dimethylgermyl)cyclopentadienyl tris (Diethylamino) Zirconium(IV) (Zr(FMe$_2$Ge-Cp)(NEt$_2$)$_3$);

the Germanium- and Zirconium-containing precursor being (fluoro dimethylgermyl)cyclopentadienyl tris (ethylamino) Zirconium(IV) (Zr(FMe$_2$Ge-Cp)(NHEt)$_3$);

the Germanium- and Zirconium-containing precursor being (fluoro dimethylgermyl)cyclopentadienyl tris (Ethylmethylamino) Zirconium(IV) (Zr(FMe$_2$Ge-Cp)(NEtMe)$_3$);

the Germanium- and Zirconium-containing precursor being (fluoro dimethylgermyl)cyclopentadienyl tris(Di n-propylamino) Zirconium(IV) (Zr(FMe$_2$Ge-Cp)(NnPr$_2$)$_3$);

the Germanium- and Zirconium-containing precursor being (fluoro dimethylgermyl)cyclopentadienyl tris(n-propylamino) Zirconium(IV) (Zr(FMe$_2$Ge-Cp)(NHnPr)$_3$);

the Germanium- and Zirconium-containing precursor being (fluoro dimethylgermyl)cyclopentadienyl tris (Diisopropylamino) Zirconium(IV) (Zr(FMe$_2$Ge-Cp)(NiPr$_2$)$_3$);

the Germanium- and Zirconium-containing precursor being (fluoro dimethylgermyl)cyclopentadienyl tris(isopropylamino) Zirconium(IV) (Zr(FMe$_2$Ge-Cp)(NHiPr)$_3$);

the Germanium- and Zirconium-containing precursor being (fluoro dimethylgermyl)cyclopentadienyl tris(Di n-butylamino) Zirconium(IV) (Zr(FMe$_2$Ge-Cp)(NnBu$_2$)$_3$);

the Germanium- and Zirconium-containing precursor being (fluoro dimethylgermyl)cyclopentadienyl tris(n-butylamino) Zirconium(IV) (Zr(FMe$_2$Ge-Cp)(NHnBu)$_3$);

the Germanium- and Zirconium-containing precursor being (fluoro dimethylgermyl)cyclopentadienyl tris(Di isobutylamino) Zirconium(IV) (Zr(FMe$_2$Ge-Cp)(NiBu$_2$)$_3$);

the Germanium- and Zirconium-containing precursor being (fluoro dimethylgermyl)cyclopentadienyl tris(isobutylamino) Zirconium(IV) (Zr(FMe$_2$Ge-Cp)(NHiBu)$_3$);

the Germanium- and Zirconium-containing precursor being (fluoro dimethylgermyl)cyclopentadienyl tris(Di sec-butylamino) Zirconium(IV) (Zr(FMe$_2$Ge-Cp)(NsBu$_2$)$_3$);

the Germanium- and Zirconium-containing precursor being (fluoro dimethylgermyl)cyclopentadienyl tris(sec-butylamino) Zirconium(IV) (Zr(FMe$_2$Ge-Cp)(NHsBu)$_3$);

the Germanium- and Zirconium-containing precursor being (fluoro dimethylgermyl)cyclopentadienyl tris(Di tert-butylamino) Zirconium(IV) (Zr(FMe$_2$Ge-Cp)(NtBu$_2$)$_3$);

the Germanium- and Zirconium-containing precursor being (fluoro dimethylgermyl)cyclopentadienyl tris(tert-butylamino) Zirconium(IV) (Zr(FMe$_2$Ge-Cp)(NHtBu)$_3$);

the Germanium- and Zirconium-containing precursor being (fluoro dimethylgermyl)cyclopentadienyl tris(methoxy) Zirconium(IV) (Zr(FMe$_2$Ge-Cp)(OMe)$_3$);

the Germanium- and Zirconium-containing precursor being (fluoro dimethylgermyl)cyclopentadienyl tris(ethoxy) Zirconium(IV) (Zr(FMe$_2$Ge-Cp)(OEt)$_3$);

the Germanium- and Zirconium-containing precursor being (fluoro dimethylgermyl)cyclopentadienyl tris(n-propoxy) Zirconium(IV) (Zr(FMe$_2$Ge-Cp)(OnPr)$_3$);

the Germanium- and Zirconium-containing precursor being (fluoro dimethylgermyl)cyclopentadienyl tris(isopropoxy) Zirconium(IV) (Zr(FMe$_2$Ge-Cp)(OiPr)$_3$);

the Germanium- and Zirconium-containing precursor being (fluoro dimethylgermyl)cyclopentadienyl tris(tert-butoxy) Zirconium(IV) (Zr(FMe$_2$Ge-Cp)(OtBu)$_3$);

the Germanium- and Zirconium-containing precursor being (fluoro dimethylgermyl)cyclopentadienyl tris(sec-butoxy) Zirconium(IV) (Zr(FMe$_2$Ge-Cp)(OsBu)$_3$);

the Germanium- and Zirconium-containing precursor being (fluoro dimethylgermyl)cyclopentadienyl tris(n-butoxy) Zirconium(IV) (Zr(FMe$_2$Ge-Cp)(OnBu)$_3$);

the Germanium- and Zirconium-containing precursor being (fluoro dimethylgermyl)cyclopentadienyl tris(isobutoxy) Zirconium(IV) (Zr(FMe$_2$Ge-Cp)(OiBu)$_3$);

the Germanium- and Zirconium-containing precursor being (tris(trifluoromethyl)germyl)cyclopentadienyl tris(Dimethylamino)Zirconium(IV) (Zr((CF$_3$)$_3$Ge-Cp)(NMe$_2$)$_3$);

the Germanium- and Zirconium-containing precursor being (tris(trifluoromethyl)germyl)cyclopentadienyl tris(methylamino) Zirconium(IV) (Zr((CF$_3$)$_3$Ge-Cp)(NHMe)$_3$);

the Germanium- and Zirconium-containing precursor being (tris(trifluoromethyl)germyl)cyclopentadienyl tris(Diethylamino) Zirconium(IV) (Zr((CF$_3$)$_3$Ge-Cp)(NEt$_2$)$_3$);

the Germanium- and Zirconium-containing precursor being (tris(trifluoromethyl)germyl)cyclopentadienyl tris(ethylamino) Zirconium(IV) (Zr((CF$_3$)$_3$Ge-Cp)(NHEt)$_3$);

the Germanium- and Zirconium-containing precursor being (tris(trifluoromethyl)germyl)cyclopentadienyl tris(Ethylmethylamino)Zirconium(IV) (Zr((CF$_3$)$_3$Ge-Cp)(NEtMe)$_3$);

the Germanium- and Zirconium-containing precursor being (tris(trifluoromethyl)germyl)cyclopentadienyl tris(Di n-propylamino)Zirconium(IV) (Zr((CF$_3$)$_3$Ge-Cp)(NnPr$_2$)$_3$);

the Germanium- and Zirconium-containing precursor being (tris(trifluoromethyl)germyl)cyclopentadienyl tris(n-propylamino)Zirconium(IV) (Zr((CF$_3$)$_3$Ge-Cp)(NHnPr)$_3$);

the Germanium- and Zirconium-containing precursor being (tris(trifluoromethyl)germyl)cyclopentadienyl tris(Di isopropylamino)Zirconium(IV) (Zr((CF$_3$)$_3$Ge-Cp)(NiPr$_2$)$_3$);

the Germanium- and Zirconium-containing precursor being (tris(trifluoromethyl)germyl)cyclopentadienyl tris(isopropylamino)Zirconium(IV) (Zr((CF$_3$)$_3$Ge-Cp)(NHiPr)$_3$);

the Germanium- and Zirconium-containing precursor being (tris(trifluoromethyl)germyl)cyclopentadienyl tris(Di n-butylamino)Zirconium(IV) (Zr((CF$_3$)$_3$Ge-Cp)(NnBu$_2$)$_3$);

the Germanium- and Zirconium-containing precursor being (tris(trifluoromethyl)germyl)cyclopentadienyl tris(n-butylamino) Zirconium(IV) (Zr((CF$_3$)$_3$Ge-Cp)(NHnBu)$_3$);

the Germanium- and Zirconium-containing precursor being (tris(trifluoromethyl)germyl)cyclopentadienyl tris(Di isobutylamino)Zirconium(IV) (Zr((CF$_3$)$_3$Ge-Cp)(NiBu$_2$)$_3$);

the Germanium- and Zirconium-containing precursor being (tris(trifluoromethyl)germyl)cyclopentadienyl tris(isobutylamino) Zirconium(IV) (Zr((CF$_3$)$_3$Ge-Cp)(NHiBu)$_3$);

the Germanium- and Zirconium-containing precursor being (tris(trifluoromethyl)germyl)cyclopentadienyl tris(Di sec-butylamino)Zirconium(IV) (Zr((CF$_3$)$_3$Ge-Cp)(NsBu$_2$)$_3$);

the Germanium- and Zirconium-containing precursor being (tris(trifluoromethyl)germyl)cyclopentadienyl tris(sec-butylamino)Zirconium(IV) (Zr((CF$_3$)$_3$Ge-Cp)(NHsBu)$_3$);

the Germanium- and Zirconium-containing precursor being (tris(trifluoromethyl)germyl)cyclopentadienyl tris(Di tert-butylamino)Zirconium(IV) (Zr((CF$_3$)$_3$Ge-Cp)(NtBu$_2$)$_3$);

the Germanium- and Zirconium-containing precursor being (tris(trifluoromethyl)germyl)cyclopentadienyl tris(tert-butylamino)Zirconium(IV) (Zr((CF$_3$)$_3$Ge-Cp)(NHtBu)$_3$);

the Germanium- and Zirconium-containing precursor being (tris(trifluoromethyl)germyl)cyclopentadienyl tris(methoxy) Zirconium(IV) (Zr((CF$_3$)$_3$Ge-Cp)(OMe)$_3$);

the Germanium- and Zirconium-containing precursor being (tris(trifluoromethyl)germyl)cyclopentadienyl tris(ethoxy) Zirconium(IV) (Zr((CF$_3$)$_3$Ge-Cp)(OEt)$_3$);

the Germanium- and Zirconium-containing precursor being (tris(trifluoromethyl)germyl)cyclopentadienyl tris(n-propoxy) Zirconium(IV) (Zr((CF$_3$)$_3$Ge-Cp)(OnPr)$_3$);

the Germanium- and Zirconium-containing precursor being (tris(trifluoromethyl)germyl)cyclopentadienyl tris(isopropoxy) Zirconium(IV) (Zr((CF$_3$)$_3$Ge-Cp)(OiPr)$_3$);

the Germanium- and Zirconium-containing precursor being (tris(trifluoromethyl)germyl)cyclopentadienyl tris(tert-butoxy) Zirconium(IV) (Zr((CF$_3$)$_3$Ge-Cp)(OtBu)$_3$);

the Germanium- and Zirconium-containing precursor being (tris(trifluoromethyl)germyl)cyclopentadienyl tris(sec-butoxy) Zirconium(IV) (Zr((CF$_3$)$_3$Ge-Cp)(OsBu)$_3$);

the Germanium- and Zirconium-containing precursor being (tris(trifluoromethyl)germyl)cyclopentadienyl tris(n-butoxy) Zirconium(IV) (Zr((CF$_3$)$_3$Ge-Cp)(OnBu)$_3$);

the Germanium- and Zirconium-containing precursor being (tris(trifluoromethyl)germyl)cyclopentadienyl tris(isobutoxy) Zirconium(IV) (Zr((CF$_3$)$_3$Ge-Cp)(OiBu)$_3$);

the Germanium- and Zirconium-containing precursor being (bis(trifluoromethyl)germyl)cyclopentadienyl tris(Dimethylamino)Zirconium(IV) (Zr((CF$_3$)$_2$HGe-Cp)(NMe$_2$)$_3$);

the Germanium- and Zirconium-containing precursor being (bis(trifluoromethyl)germyl)cyclopentadienyl tris(methylamino) Zirconium(IV) (Zr((CF$_3$)$_2$HGe-Cp)(NHMe)$_3$);

the Germanium- and Zirconium-containing precursor being (bis(trifluoromethyl)germyl)cyclopentadienyl tris(Diethylamino) Zirconium(IV) (Zr((CF$_3$)$_2$HGe-Cp)(NEt$_2$)$_3$);

the Germanium- and Zirconium-containing precursor being (bis(trifluoromethyl)germyl)cyclopentadienyl tris(ethylamino) Zirconium(IV) (Zr((CF$_3$)$_2$HGe-Cp)(NHEt)$_3$);

the Germanium- and Zirconium-containing precursor being (bis(trifluoromethyl)germyl)cyclopentadienyl tris(Ethylmethylamino)Zirconium(IV) (Zr((CF$_3$)$_2$HGe-Cp)(NEtMe)$_3$);

the Germanium- and Zirconium-containing precursor being (bis(trifluoromethyl)germyl)cyclopentadienyl tris(Di n-propylamino)Zirconium(IV) (Zr((CF$_3$)$_2$HGe-Cp)(NnPr$_2$)$_3$);

the Germanium- and Zirconium-containing precursor being (bis(trifluoromethyl)germyl)cyclopentadienyl tris(n-propylamino) Zirconium(IV) (Zr((CF$_3$)$_2$HGe-Cp)(NHnPr)$_3$);

the Germanium- and Zirconium-containing precursor being (bis(trifluoromethyl)germyl)cyclopentadienyl tris(Di isopropylamino)Zirconium(IV) (Zr((CF$_3$)$_2$HGe-Cp)(NiPr$_2$)$_3$);

the Germanium- and Zirconium-containing precursor being (bis(trifluoromethyl)germyl)cyclopentadienyl tris(isopropylamino)Zirconium(IV) (Zr((CF$_3$)$_2$HGe-Cp)(NHiPr)$_3$);

the Germanium- and Zirconium-containing precursor being (bis(trifluoromethyl)germyl)cyclopentadienyl tris(Di n-butylamino)Zirconium(IV) (Zr((CF$_3$)$_2$HGe-Cp)(NnBu$_2$)$_3$);

the Germanium- and Zirconium-containing precursor being (bis(trifluoromethyl)germyl)cyclopentadienyl tris(n-butylamino) Zirconium(IV) (Zr((CF$_3$)$_2$HGe-Cp)(NHnBu)$_3$);

the Germanium- and Zirconium-containing precursor being (bis(trifluoromethyl)germyl)cyclopentadienyl tris(Di isobutylamino)Zirconium(IV) (Zr((CF$_3$)$_2$HGe-Cp)(NiBu$_2$)$_3$);

the Germanium- and Zirconium-containing precursor being (bis(trifluoromethyl)germyl)cyclopentadienyl tris(isobutylamino) Zirconium(IV) (Zr((CF$_3$)$_2$HGe-Cp)(NHiBu)$_3$);

the Germanium- and Zirconium-containing precursor being (bis(trifluoromethyl)germyl)cyclopentadienyl tris(Di sec-butylamino)Zirconium(IV) (Zr((CF$_3$)$_2$HGe-Cp)(NsBu$_2$)$_3$);

the Germanium- and Zirconium-containing precursor being (bis(trifluoromethyl)germyl)cyclopentadienyl tris(sec-butylamino)Zirconium(IV) (Zr((CF$_3$)$_2$HGe-Cp)(NHsBu)$_3$);

the Germanium- and Zirconium-containing precursor being (bis(trifluoromethyl)germyl)cyclopentadienyl tris(Di tert-butylamino)Zirconium(IV) (Zr((CF$_3$)$_2$HGe-Cp)(NtBu$_2$)$_3$);

the Germanium- and Zirconium-containing precursor being (bis(trifluoromethyl)germyl)cyclopentadienyl tris(tert-butylamino)Zirconium(IV) (Zr((CF$_3$)$_2$HGe-Cp)(NHtBu)$_3$);

the Germanium- and Zirconium-containing precursor being (bis(trifluoromethyl)germyl)cyclopentadienyl tris(methoxy) Zirconium(IV) (Zr((CF$_3$)$_2$HGe-Cp)(OMe)$_3$);

the Germanium- and Zirconium-containing precursor being (bis(trifluoromethyl)germyl)cyclopentadienyl tris(ethoxy) Zirconium(IV) (Zr((CF$_3$)$_2$HGe-Cp)(OEt)$_3$);

the Germanium- and Zirconium-containing precursor being (bis(trifluoromethyl)germyl)cyclopentadienyl tris(n-propoxy) Zirconium(IV) (Zr((CF$_3$)$_2$HGe-Cp)(OnPr)$_3$);

the Germanium- and Zirconium-containing precursor being (bis(trifluoromethyl)germyl)cyclopentadienyl tris(isopropoxy) Zirconium(IV) (Zr((CF$_3$)$_2$HGe-Cp)(OiPr)$_3$);

the Germanium- and Zirconium-containing precursor being (bis(trifluoromethyl)germyl)cyclopentadienyl tris(tert-butoxy) Zirconium(IV) (Zr((CF$_3$)$_2$HGe-Cp)(OtBu)$_3$);

the Germanium- and Zirconium-containing precursor being (bis(trifluoromethyl)germyl)cyclopentadienyl tris(sec-butoxy) Zirconium(IV) (Zr((CF$_3$)$_2$HGe-Cp)(OsBu)$_3$);

the Germanium- and Zirconium-containing precursor being (bis(trifluoromethyl)germyl)cyclopentadienyl tris(n-butoxy) Zirconium(IV) (Zr((CF$_3$)$_2$HGe-Cp)(OnBu)$_3$);

the Germanium- and Zirconium-containing precursor being (bis(trifluoromethyl)germyl)cyclopentadienyl tris(iso-butoxy) Zirconium(IV) (Zr((CF$_3$)$_2$HGe-Cp)(OiBu)$_3$);

the Germanium- and Zirconium-containing precursor being ((trifluoromethyl)dimethylgermyl)cyclopentadienyl tris(Dimethylamino)Zirconium(IV) (Zr((CF$_3$)Me$_2$Ge-Cp)(NMe$_2$)$_3$);

the Germanium- and Zirconium-containing precursor being ((trifluoromethyl)dimethylgermyl)cyclopentadienyl tris(methylamino)Zirconium(IV) (Zr((CF$_3$)Me$_2$Ge-Cp)(NHMe)$_3$);

the Germanium- and Zirconium-containing precursor being ((trifluoromethyl)dimethylgermyl)cyclopentadienyl tris(Diethylamino)Zirconium(IV) (Zr((CF$_3$)Me$_2$Ge-Cp)(NEt$_2$)$_3$);

the Germanium- and Zirconium-containing precursor being ((trifluoromethyl)dimethylgermyl)cyclopentadienyl tris(ethylamino)Zirconium(IV) (Zr((CF$_3$)Me$_2$Ge-Cp)(NHEt)$_3$);

the Germanium- and Zirconium-containing precursor being ((trifluoromethyl)dimethylgermyl)cyclopentadienyl tris(Ethylmethylamino)Zirconium(IV) (Zr((CF$_3$)Me$_2$Ge-Cp)(NEtMe)$_3$);

the Germanium- and Zirconium-containing precursor being ((trifluoromethyl)dimethylgermyl)cyclopentadienyl tris(Di n-propylamino)Zirconium(IV) (Zr((CF$_3$)Me$_2$Ge-Cp)(NnPr$_2$)$_3$);

the Germanium- and Zirconium-containing precursor being ((trifluoromethyl)dimethylgermyl)cyclopentadienyl tris(n-propylamino)Zirconium(IV) (Zr((CF$_3$)Me$_2$Ge-Cp)(NHnPr)$_3$);

the Germanium- and Zirconium-containing precursor being ((trifluoromethyl)dimethylgermyl)cyclopentadienyl tris(Di isopropylamino)Zirconium(IV) (Zr((CF$_3$)Me$_2$Ge-Cp)(NiPr$_2$)$_3$);

the Germanium- and Zirconium-containing precursor being ((trifluoromethyl)dimethylgermyl)cyclopentadienyl tris(isopropylamino)Zirconium(IV) (Zr((CF$_3$)Me$_2$Ge-Cp)(NHiPr)$_3$);

the Germanium- and Zirconium-containing precursor being ((trifluoromethyl)dimethylgermyl)cyclopentadienyl tris(Di n-butylamino)Zirconium(IV) (Zr((CF$_3$)Me$_2$Ge-Cp)(NnBu$_2$)$_3$);

the Germanium- and Zirconium-containing precursor being ((trifluoromethyl)dimethylgermyl)cyclopentadienyl tris(n-butylamino)Zirconium(IV) (Zr((CF$_3$)Me$_2$Ge-Cp)(NHnBu)$_3$);

the Germanium- and Zirconium-containing precursor being ((trifluoromethyl)dimethylgermyl)cyclopentadienyl tris(Di isobutylamino)Zirconium(IV) (Zr((CF$_3$)Me$_2$Ge-Cp)(NiBu$_2$)$_3$);

the Germanium- and Zirconium-containing precursor being ((trifluoromethyl)dimethylgermyl)cyclopentadienyl tris(isobutylamino)Zirconium(IV) (Zr((CF$_3$)Me$_2$Ge-Cp)(NHiBu)$_3$);

the Germanium- and Zirconium-containing precursor being ((trifluoromethyl)dimethylgermyl)cyclopentadienyl tris(Di sec-butylamino)Zirconium(IV) (Zr((CF$_3$)Me$_2$Ge-Cp)(NsBu$_2$)$_3$);

the Germanium- and Zirconium-containing precursor being ((trifluoromethyl)dimethylgermyl)cyclopentadienyl tris(sec-butylamino)Zirconium(IV) (Zr((CF$_3$)Me$_2$Ge-Cp)(NHsBu)$_3$);

the Germanium- and Zirconium-containing precursor being ((trifluoromethyl)dimethylgermyl)cyclopentadienyl tris(Di tert-butylamino)Zirconium(IV) (Zr((CF$_3$)Me$_2$Ge-Cp)(NtBu$_2$)$_3$);

the Germanium- and Zirconium-containing precursor being ((trifluoromethyl)dimethylgermyl)cyclopentadienyl tris(tert-butylamino)Zirconium(IV) (Zr((CF$_3$)Me$_2$Ge-Cp)(NHtBu)$_3$);

the Germanium- and Zirconium-containing precursor being ((trifluoromethyl)dimethylgermyl)cyclopentadienyl tris(methoxy) Zirconium(IV) (Zr((CF$_3$)Me$_2$Ge-Cp)(OMe)$_3$);

the Germanium- and Zirconium-containing precursor being ((trifluoromethyl)dimethylgermyl)cyclopentadienyl tris(ethoxy) Zirconium(IV) (Zr((CF$_3$)Me$_2$Ge-Cp)(OEt)$_3$);

the Germanium- and Zirconium-containing precursor being ((trifluoromethyl)dimethylgermyl)cyclopentadienyl tris(n-propoxy)Zirconium(IV) (Zr((CF$_3$)Me$_2$Ge-Cp)(OnPr)$_3$);

the Germanium- and Zirconium-containing precursor being ((trifluoromethyl)dimethylgermyl)cyclopentadienyl tris(isopropoxy)Zirconium(IV) (Zr((CF$_3$)Me$_2$Ge-Cp)(OiPr)$_3$);

the Germanium- and Zirconium-containing precursor being ((trifluoromethyl)dimethylgermyl)cyclopentadienyl tris(tert-butoxy)Zirconium(IV) (Zr((CF$_3$)Me$_2$Ge-Cp)(OtBu)$_3$);

the Germanium- and Zirconium-containing precursor being ((trifluoromethyl)dimethylgermyl)cyclopentadienyl tris(sec-butoxy)Zirconium(IV) (Zr((CF$_3$)Me$_2$Ge-Cp)(OsBu)$_3$);

the Germanium- and Zirconium-containing precursor being ((trifluoromethyl)dimethylgermyl)cyclopentadienyl tris(n-butoxy) Zirconium(IV) (Zr((CF$_3$)Me$_2$Ge-Cp)(OnBu)$_3$);

the Germanium- and Zirconium-containing precursor being ((trifluoromethyl)dimethylgermyl)cyclopentadienyl tris(isobutoxy)Zirconium(IV) (Zr((CF$_3$)Me$_2$Ge-Cp)(OiBu)$_3$);

the Germanium- and Zirconium-film forming composition comprising between approximately 95% w/w and approximately 100% w/w of the precursor;

the Germanium- and Zirconium-film forming composition comprising between approximately 98% w/w and approximately 100% w/w of the precursor;

the Germanium- and Zirconium-film forming composition comprising between approximately 99% w/w and approximately 100% w/w of the precursor;

the Germanium- and Zirconium-film forming composition comprising between approximately 0.0% w/w and approximately 5.0% w/w impurities;

the Germanium- and Zirconium-film forming composition comprising between approximately 0.0% w/w and approximately 2.0% w/w impurities;

the Germanium- and Zirconium-film forming composition comprising between approximately 0.0% w/w and approximately 1.0% w/w impurities;

the impurities including alcohol; alkylamines; dialkylamines; alkylimines; cyclopentadiene; dicyclopentadiene; alkylgermane; THF; ether; pentane; cyclohexane; heptanes; benzene; toluene; chlorinated metal compounds; lithium, sodium, or potassium alkylamino; lithium, sodium, or potassium alkoxy; and lithium, sodium, or potassium cyclopentadienyl;

the Germanium- and Zirconium-film forming composition comprising between approximately 0.0% w/w and approximately 2.0% w/w alkylamine impurities;

the Germanium- and Zirconium-film forming composition comprising between approximately 0.0% w/w and approximately 2.0% w/w alkylimine impurities;

the Germanium- and Zirconium-film forming composition comprising between approximately 0.0% w/w and approximately 2.0% w/w alcohol impurities;
the Germanium- and Zirconium-film forming composition comprising between approximately 0.0% w/w and approximately 2.0% w/w cyclopentadiene impurities;
the Germanium- and Zirconium-film forming composition comprising between approximately 0.0% w/w and approximately 2.0% w/w dicyclopentadiene impurities;
the Germanium- and Zirconium-film forming composition comprising between approximately 0.0% w/w and approximately 2.0% w/w alkylgermane impurities;
the Germanium- and Zirconium-film forming composition comprising between approximately 0.0% w/w and approximately 2.0% w/w THF impurities;
the Germanium- and Zirconium-film forming composition comprising between approximately 0.0% w/w and approximately 2.0% w/w ether impurities;
the Germanium- and Zirconium-film forming composition comprising between approximately 0.0% w/w and approximately 2.0% w/w pentane impurities;
the Germanium- and Zirconium-film forming composition comprising between approximately 0.0% w/w and approximately 2.0% w/w cyclohexane impurities;
the Germanium- and Zirconium-film forming composition comprising between approximately 0.0% w/w and approximately 2.0% w/w heptanes impurities;
the Germanium- and Zirconium-film forming composition comprising between approximately 0.0% w/w and approximately 2.0% w/w benzene impurities;
the Germanium- and Zirconium-film forming composition comprising between approximately 0.0% w/w and approximately 2.0% w/w toluene impurities;
the Germanium- and Zirconium-film forming composition comprising between approximately 0.0% w/w and approximately 2.0% w/w chlorinated metal compound impurities;
the Germanium- and Zirconium-film forming composition comprising between approximately 0.0% w/w and approximately 2.0% w/w lithium, sodium, or potassium cyclopentadienyl impurities;
the Germanium- and Zirconium-film forming composition comprising between approximately 0.0% w/w and approximately 2.0% w/w lithium, sodium, or potassium alkylamino impurities;
the Germanium- and Zirconium-film forming composition comprising between approximately 0.0% w/w and approximately 2.0% w/w lithium, sodium, or potassium alkoxy impurities;
the Germanium- and Zirconium-film forming composition comprising between approximately 0 ppbw and approximately 1 ppmw metal impurities;
the Germanium- and Zirconium-film forming composition comprising between approximately 0 ppbw and approximately 500 ppbw metal impurities;
the metal impurities including Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), and Zinc (Zn);
the Germanium- and Zirconium-film forming composition comprising between approximately 0 ppbw and approximately 500 ppbw Al impurities;
the Germanium- and Zirconium-film forming composition comprising between approximately 0 ppbw and approximately 500 ppbw As impurities;
the Germanium- and Zirconium-film forming composition comprising between approximately 0 ppbw and approximately 500 ppbw Ba impurities;
the Germanium- and Zirconium-film forming composition comprising between approximately 0 ppbw and approximately 500 ppbw Be impurities;
the Germanium- and Zirconium-film forming composition comprising between approximately 0 ppbw and approximately 500 ppbw Bi impurities;
the Germanium- and Zirconium-film forming composition comprising between approximately 0 ppbw and approximately 500 ppbw Cd impurities;
the Germanium- and Zirconium-film forming composition comprising between approximately 0 ppbw and approximately 500 ppbw Ca impurities;
the Germanium- and Zirconium-film forming composition comprising between approximately 0 ppbw and approximately 500 ppbw Cr impurities;
the Germanium- and Zirconium-film forming composition comprising between approximately 0 ppbw and approximately 500 ppbw Co impurities;
the Germanium- and Zirconium-film forming composition comprising between approximately 0 ppbw and approximately 500 ppbw Cu impurities;
the Germanium- and Zirconium-film forming composition comprising between approximately 0 ppbw and approximately 500 ppbw Ga impurities;
the Germanium- and Zirconium-film forming composition comprising between approximately 0 ppbw and approximately 500 ppbw Ge impurities;
the Germanium- and Zirconium-film forming composition comprising between approximately 0 ppbw and approximately 500 ppbw Hf impurities;
the Germanium- and Zirconium-film forming composition comprising between approximately 0 ppbw and approximately 500 ppbw Zr impurities;
the Germanium- and Zirconium-film forming composition comprising between approximately 0 ppbw and approximately 500 ppbw In impurities;
the Germanium- and Zirconium-film forming composition comprising between approximately 0 ppbw and approximately 500 ppbw Fe impurities;
the Germanium- and Zirconium-film forming composition comprising between approximately 0 ppbw and approximately 500 ppbw Pb impurities;
the Germanium- and Zirconium-film forming composition comprising between approximately 0 ppbw and approximately 500 ppbw Li impurities;
the Germanium- and Zirconium-film forming composition comprising between approximately 0 ppbw and approximately 500 ppbw Mg impurities;
the Germanium- and Zirconium-film forming composition comprising between approximately 0 ppbw and approximately 500 ppbw Mn impurities;
the Germanium- and Zirconium-film forming composition comprising between approximately 0 ppbw and approximately 500 ppbw W impurities;
the Germanium- and Zirconium-film forming composition comprising between approximately 0 ppbw and approximately 500 ppbw Ni impurities;
the Germanium- and Zirconium-film forming composition comprising between approximately 0 ppbw and approximately 500 ppbw K impurities;

the Germanium- and Zirconium-film forming composition comprising between approximately 0 ppbw and approximately 500 ppbw Na impurities;
the Germanium- and Zirconium-film forming composition comprising between approximately 0 ppbw and approximately 500 ppbw Sr impurities;
the Germanium- and Zirconium-film forming composition comprising between approximately 0 ppbw and approximately 500 ppbw Th impurities;
the Germanium- and Zirconium-film forming composition comprising between approximately 0 ppbw and approximately 500 ppbw Sn impurities;
the Germanium- and Zirconium-film forming composition comprising between approximately 0 ppbw and approximately 500 ppbw Ti impurities;
the Germanium- and Zirconium-film forming composition comprising between approximately 0 ppbw and approximately 500 ppbw U impurities; and
the Germanium- and Zirconium-film forming composition comprising between approximately 0 ppbw and approximately 500 ppbw Zn impurities.

Also disclosed are processes for the deposition of Zirconium-containing films on substrates. The Germanium- and Zirconium-film forming compositions disclosed above are introduced into a reactor having a substrate disposed therein. At least part of the precursor is deposited onto the substrate to form the Zirconium-containing film. The disclosed processes may further include one or more of the following aspects:

introducing a reactant into the reactor;
the reactant being plasma-treated;
the reactant being remote plasma-treated;
the reactant not being plasma-treated;
the reactant being selected from the group consisting of $H_2$, $H_2CO$, $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;
the reactant being $H_2$;
the reactant being $NH_3$;
the reactant being selected from the group consisting of $O_2$, $O_3$, $H_2O$, $H_2O_2$, NO, $N_2O$, $NO_2$, oxygen radicals thereof, and mixtures thereof;
the reactant being $H_2O$;
the reactant being plasma treated $O_2$;
the reactant being $O_3$;
the reactant being a Zirconium-containing precursor;
the Zirconium-containing precursor being selected from the group consisting of $ZrCp(NMe_2)_3$, $Zr(MeCp)(NMe_2)_3$, $Zr(EtCp)(NMe_2)_3$, $Zr(iPrCp)(NMe_2)_3$, $Zr(tBuCp)(NMe_2)_3$, $Zr(Cp)(NMeEt)_3$;
the Zirconium-containing precursor being $ZrCp(NMe_2)_3$;
mixing the Germanium- and Zirconium-film forming composition and the Zirconium-containing precursor to form a mixture prior to introduction into the reactor;
the Germanium- and Zirconium-film forming composition and the reactant being introduced into the reactor simultaneously;
the reactor being configured for chemical vapor deposition;
the reactor being configured for plasma enhanced chemical vapor deposition;
the Germanium- and Zirconium-film forming composition and the reactant being introduced into the chamber sequentially;
the reactor being configured for atomic layer deposition;
the reactor being configured for plasma enhanced atomic layer deposition;
the reactor being configured for spatial atomic layer deposition;
the Zirconium-containing film being a pure Zirconium film;
the pure Zirconium film having a Zr concentration between approximately 95 atomic % to approximately 100 atomic %;
the Zirconium-containing film being a Zirconium silicide ($Zr_kSi_l$, wherein each of k and l is an integer which inclusively range from 1 to 6);
the Zirconium silicide being $ZrSi_2$;
the Zirconium-containing film being a Zirconium oxide ($Zr_mO_n$, wherein each of m and n is an integer which inclusively range from 1 to 6);
the zirconium oxide being $ZrO_2$;
the Zirconium-containing film being a Germanium-doped Zirconium oxide ($Zr_oGe_pO_q$), wherein each o and p is a decimal which inclusively ranges from 0 to 1 and q is an integer which inclusively ranges from 1 to 6);
the silicon-doped Zirconium oxide being $Zr_{(0.99\ to\ 0.5)}Ge_{(0.5\ to\ 0.01)}O_2$;
the Zirconium-containing film being a Zirconium nitride ($Zr_uN_v$, wherein each of u and v is an integer which inclusively range from 1 to 6); and
the Zirconium nitride being ZrN.

NOTATION AND NOMENCLATURE

Certain abbreviations, symbols, and terms are used throughout the following description and claims, and include:

As used herein, the indefinite article "a" or "an" means one or more.

As used herein, the terms "approximately" or "about" mean±10% of the value stated.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $Zr(TMGCp)(NR^1R^2)_3$, the three $R^1$ groups may, but need not be identical to each other or to $R^2$.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a propyl group; the abbreviation "nPr" refers to a "normal" or linear propyl group; the abbreviation "iPr" refers to an isopropyl group; the abbreviation "Bu" refers to a butyl group; the abbreviation "nBu" refers to a "normal" or linear butyl group; the abbreviation "tBu" refers to a tert-butyl group, also known as 1,1-dimethylethyl; the abbreviation "sBu" refers to a sec-butyl group, also known as 1-methylpropyl; the abbreviation "iBu" refers to an iso-butyl group, also known as 2-methylpropyl; the abbreviation "amyl" refers to an amyl or pentyl group; the abbreviation "tAmyl" refers to a tert-amyl group, also known as 1,1-dimethylpropyl; the abbreviation "Cp" refers to cyclopentadienyl; the abbreviation "Cp*" refers to pentamethylcyclopentadienyl; the abbreviation "op" refers to (open)pentadienyl; the abbreviation "TMGCp" refers to the ligand (trimethylgermyl)cyclopentadienyl [Me$_3$GeCp]; the abbreviation "TMGCpH" refers to the molecule (trimethylgermyl)cyclopentadiene [Me$_3$GeCpH]; the abbreviation DMGCp refers to the ligand (dimethylgermyl)cyclopentadienyl [Me$_2$HGeCp]; the abbreviation "TMSCp" refers to the ligand (trimethylsilyl)cyclopentadienyl [Me$_3$SiCp]; and the abbreviation "TMSCpH" refers to the molecule (trimethylsilyl)cyclopentadiene [Me$_3$SiCpH].

The standard abbreviations of the elements from the periodic table of elements are used herein. It should be understood that elements may be referred to by these abbreviations (e.g., Ge refers to germanium, Si refers to silicon, C refers to carbon, etc.).

BRIEF DESCRIPTION OF THE FIGURES

For a further understanding of the nature and objects of the present invention, reference should be made to the following detailed description, taken in conjunction with the accompanying figure wherein.

DESCRIPTION OF PREFERRED EMBODIMENTS

Figure 1:
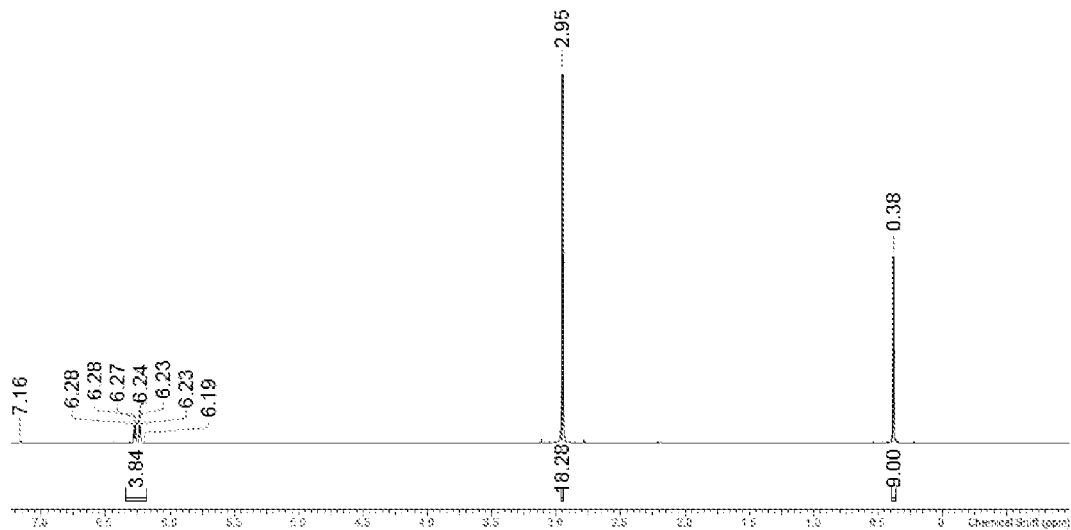
FIG. 1 is a $^1$HNMR spectrum of Zr(TMGCp)(NMe$_2$)$_3$.

Disclosed are Germanium- and Zirconium-film forming compositions comprising a Germanium- and Zirconium-containing precursor having the following formula:

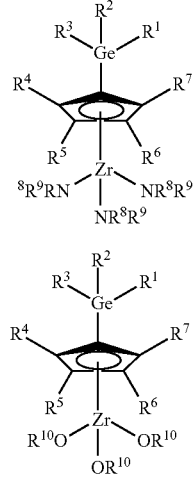

wherein each $R^1$, $R^2$, $R^3$, $R^4$, $R^5$, $R^6$, $R^7$, $R^8$, $R^9$ and $R^{10}$ is independently selected from H; a C1-C5 linear, branched, or cyclic alkyl group; or a C1-C5 linear, branched, or cyclic fluoroalkyl group. $R^1$, $R^2$ and $R^3$ may be identical or different. $R^4$, $R^5$, $R^6$ and $R^7$ may be identical or different. $R^8$ and $R^9$ may be identical or different.

Preferably $R^1$, $R^2$, $R^3$, $R^4$, $R^5$, $R^6$ and $R^7$ are H or Me because smaller alkyl groups may increase the volatility and decrease the melting point of the germanium- and zirconium-containing compound. Preferably $R^8$ and $R^9$ are H, Me or Et because smaller alkyl groups may increase the volatility and decrease the melting point of the germanium- and zirconium-containing compound. Preferably $R^{10}$ is Me, Et, iPr or tBu because the smaller alkyl groups (Me, Et) may increase the volatility and the larger alkyl groups (iPr, tBu) may decrease the melting point of the germanium- and zirconium-containing precursor.

Exemplary Germanium- and Zirconium-containing precursors of Formula I include but are not limited to Zr(TMG-Cp)(NMe$_2$)$_3$, Zr(TMG-Cp)(NHMe)$_3$, Zr(TMG-Cp)(NEt$_2$)$_3$, Zr(TMG-Cp)(NHEt)$_3$, Zr(TMG-Cp)(NEtMe)$_3$), Zr(TMG-Cp)(NnPr$_2$)$_3$, Zr(TMG-Cp)(NHnPr)$_3$, Zr(TMG-Cp)(NiPr$_2$)$_3$, Zr(TMG-Cp)(NHiPr)$_3$, Zr(TMG-Cp)(NnBu$_2$)$_3$), Zr(TMG-Cp)(NHnBu)$_3$, Zr(TMG-Cp)(NiBu$_2$)$_3$, Zr(TMG-Cp)(NHiBu)$_3$, Zr(TMG-Cp)(NsBu$_2$)$_3$, Zr(TMSG-Cp)(NHsBu)$_3$, Zr(TMG-Cp)(NtBu$_2$)$_3$, Zr(TMG-Cp)(NHtBu)$_3$, Zr(DMG-Cp)(NMe$_2$)$_3$, Zr(DMG-Cp)(NHMe)$_3$, Zr(DMG-Cp)(NEt$_2$)$_3$, Zr(DMG-Cp)(NHEt)$_3$, Zr(DMG-Cp)(NEtMe)$_3$, Zr(DMG-Cp)(NnPr$_2$)$_3$, Zr(DMG-Cp)(NHnPr)$_3$, Zr(DMG-Cp)(NiPr$_2$)$_3$, Zr(DMG-Cp)(NHiPr)$_3$, Zr(DMG-Cp)(NnBu$_2$)$_3$, Zr(DMG-Cp)(NHnBu)$_3$, Zr(DMG-Cp)(NiBu$_2$)$_3$, Zr(DMG-Cp)(NHiBu)$_3$, Zr(DMG-Cp)(NsBu$_2$)$_3$, Zr(DMG-Cp)(NHsBu)$_3$, Zr(DMG-Cp)(NtBu$_2$)$_3$, Zr(DMG-Cp)(NHtBu)$_3$, Zr(F$_3$Ge-Cp)(NMe$_2$)$_3$, Zr(F$_3$Ge-Cp)(NHMe)$_3$, Zr(F$_3$Ge-Cp)(NEt$_2$)$_3$, Zr(F$_3$Ge-Cp)(NHEt)$_3$, Zr(F$_3$Ge-Cp)(NEtMe)$_3$, Zr(F$_3$Ge-Cp)(NnPr$_2$)$_3$, Zr(F$_3$Ge-Cp)(NHnPr)$_3$, Zr(F$_3$Ge-Cp)(NiPr$_2$)$_3$, Zr(F$_3$Ge-Cp)(NHiPr)$_3$, Zr(F$_3$Ge-Cp)(NnBu$_2$)$_3$, Zr(F$_3$Ge-Cp)(NHnBu)$_3$, Zr(F$_3$Ge-Cp)(NiBu$_2$)$_3$, Zr(F$_3$Ge-Cp)(NHiBu)$_3$, Zr(F$_3$Ge-Cp)(NsBu$_2$)$_3$, Zr(F$_3$Ge-Cp)(NHsBu)$_3$, Zr(F$_3$Ge-Cp)(NtBu$_2$)$_3$, Zr(F$_3$Ge-Cp)(NHtBu)$_3$, Zr(F$_2$HGe-Cp)(NMe$_2$)$_3$, Zr(F$_2$HGe-Cp)(NHMe)$_3$, Zr(F$_2$HGe-Cp)(NEt$_2$)$_3$, Zr(F$_2$HGe-Cp)(NHEt)$_3$, Zr(F$_2$HGe-Cp)(NEtMe)$_3$, Zr(F$_2$HGe-Cp)(NnPr$_2$)$_3$, Zr(F$_2$HGe-Cp)(NHnPr)$_3$, Zr(F$_2$HGe-Cp)(NiPr$_2$)$_3$, Zr(F$_2$HGe-Cp)(NHiPr)$_3$, Zr(F$_2$HGe-Cp)(NnBu$_2$)$_3$, Zr(F$_2$HGe-Cp)(NHnBu)$_3$, Zr(F$_2$HGe-Cp)(NiBu$_2$)$_3$, Zr(F$_2$HGe-Cp)(NHiBu)$_3$, Zr(F$_2$HGe-Cp)(NsBu$_2$)$_3$, Zr(F$_2$HGe-Cp)(NHsBu)$_3$, Zr(F$_2$HGe-Cp)(NtBu$_2$)$_3$, Zr(F$_2$HGe-Cp)(NHtBu)$_3$, Zr(FH$_2$Ge-Cp)(NMe$_2$)$_3$, Zr(FH$_2$Ge-Cp)(NHMe)$_3$, Zr(FH$_2$Ge-Cp)(NEt$_2$)$_3$, Zr(FH$_2$Ge-Cp)(NHEt)$_3$, Zr(FH$_2$Ge-Cp)(NEtMe)$_3$, Zr(FH$_2$Ge-Cp)(NnPr$_2$)$_3$, Zr(FH$_2$Ge-Cp)(NHnPr)$_3$, Zr(FH$_2$Ge-Cp)(NiPr$_2$)$_3$, Zr(FH$_2$Ge-Cp)(NHiPr)$_3$, Zr(FH$_2$Ge-Cp)(NnBu$_2$)$_3$, Zr(FH$_2$Ge-Cp)(NHnBu)$_3$, Zr(FH$_2$Ge-Cp)(NiBu$_2$)$_3$, Zr(FH$_2$Ge-Cp)(NHiBu)$_3$, Zr(FH$_2$Ge-Cp)(NsBu$_2$)$_3$, Zr(FH$_2$Ge-Cp)(NHsBu)$_3$, Zr(FH$_2$Ge-Cp)(NtBu$_2$)$_3$, Zr(FH$_2$Ge-Cp)(NHtBu)$_3$, Zr(FMe$_2$Ge-Cp)(NMe$_2$)$_3$, Zr(FMe$_2$Ge-Cp)(NHMe)$_3$, Zr(FMe$_2$Ge-Cp)(NEt$_2$)$_3$, Zr(FMe$_2$Ge-Cp)(NHEt)$_3$, Zr(FMe$_2$Ge-Cp)(NEtMe)$_3$, Zr(FMe$_2$Ge-Cp)(NnPr$_2$)$_3$, Zr(FMe$_2$Ge-Cp)(NHnPr)$_3$, Zr(FMe$_2$Ge-Cp)(NiPr$_2$)$_3$, Zr(FMe$_2$Ge-Cp)(NHiPr)$_3$, Zr(FMe$_2$Ge-Cp)(NnBu$_2$)$_3$, Zr(FMe$_2$Ge-Cp)(NHnBu)$_3$, Zr(FMe$_2$Ge-Cp)(NiBu$_2$)$_3$, Zr(FMe$_2$Ge-Cp)(NHiBu)$_3$, Zr(FMe$_2$Ge-Cp)(NsBu$_2$)$_3$, Zr(FMe$_2$Ge-Cp)(NHsBu)$_3$, Zr(FMe$_2$Ge-Cp)(NtBu$_2$)$_3$, Zr(FMe$_2$Ge-Cp)(NHtBu)$_3$, Zr((CF$_3$)$_3$Ge-Cp)(NMe$_2$)$_3$, Zr((CF$_3$)$_3$Ge-Cp)(NHMe)$_3$, Zr((CF$_3$)$_3$Ge-Cp)(NEt$_2$)$_3$, Zr((CF$_3$)$_3$Ge-Cp)(NHEt)$_3$, Zr((CF$_3$)$_3$Ge-Cp)(NEtMe)$_3$, Zr((CF$_3$)$_3$Ge-Cp)(NnPr$_2$)$_3$, Zr((CF$_3$)$_3$Ge-Cp)(NHnPr)$_3$, Zr((CF$_3$)$_3$Ge-Cp)(NiPr$_2$)$_3$, Zr((CF$_3$)$_3$Ge-Cp)(NHiPr)$_3$, Zr((CF$_3$)$_3$Ge-Cp)(NnBu$_2$)$_3$, Zr((CF$_3$)$_3$Ge-Cp)(NHnBu)$_3$, Zr((CF$_3$)$_3$Ge-Cp)(NiBu$_2$)$_3$, Zr((CF$_3$)$_3$Ge-Cp)(NHiBu)$_3$, Zr((CF$_3$)$_3$Ge-Cp)(NsBu$_2$)$_3$, Zr((CF$_3$)$_3$Ge-Cp)(NHsBu)$_3$, Zr((CF$_3$)$_3$Ge-Cp)(NtBu$_2$)$_3$, Zr((CF$_3$)$_3$Ge-Cp)(NHtBu)$_3$, Zr((CF$_3$)$_2$HGe-Cp)(NMe)$_3$, Zr((CF$_3$)$_2$HGe-Cp)(NHMe)$_3$, Zr((CF$_3$)$_2$HGe-Cp)(NEt$_2$)$_3$, Zr((CF$_3$)$_2$HGe-Cp)(NHEt)$_3$, Zr((CF$_3$)$_2$HGe-Cp)(NEtMe)$_3$, Zr((CF$_3$)$_2$HGe-Cp)(NnPr$_2$)$_3$, Zr((CF$_3$)$_2$HGe-Cp)(NHnPr)$_3$, Zr((CF$_3$)$_2$HGe-Cp)(NiPr$_2$)$_3$, Zr((CF$_3$)$_2$HGe-Cp)(NHiPr)$_3$, Zr((CF$_3$)$_2$HGe-Cp)(NnBu$_2$)$_3$, Zr((CF$_3$)$_2$HGe-Cp)(NHnBu)$_3$, Zr((CF$_3$)$_2$HGe-Cp)(NiBu$_2$)$_3$, Zr((CF$_3$)$_2$HGe-Cp)(NHiBu)$_3$, Zr((CF$_3$)$_2$HGe-Cp)(NsBu$_2$)$_3$, Zr((CF$_3$)$_2$HGe-Cp)(NHsBu)$_3$, Zr((CF$_3$)$_2$HGe-Cp)(NtBu$_2$)$_3$, Zr((CF$_3$)$_2$HGe-Cp)(NHtBu)$_3$, Zr((CF$_3$)Me$_2$Ge-Cp)(NMe$_2$)$_3$, Zr((CF$_3$)Me$_2$Ge-Cp)(NHMe)$_3$, Zr((CF$_3$)Me$_2$Ge-Cp)(NEt$_2$)$_3$, Zr((CF$_3$)Me$_2$Ge-Cp)(NHEt)$_3$, Zr((CF$_3$)Me$_2$Ge-Cp)(NEtMe)$_3$, Zr((CF$_3$)Me$_2$Ge-Cp)(NnPr$_2$)$_3$, Zr((CF$_3$)Me$_2$Ge-Cp)(NHnPr)$_3$, Zr((CF$_3$)Me$_2$Ge-Cp)(NiPr$_2$)$_3$, Zr((CF$_3$)Me$_2$Ge-Cp)(NHiPr)$_3$, Zr((CF$_3$)Me$_2$Ge-Cp)(NnBu$_2$)$_3$, Zr((CF$_3$)Me$_2$Ge-Cp)(NHnBu)$_3$, Zr((CF$_3$)Me$_2$Ge-Cp)(NiBu$_2$)$_3$, Zr((CF$_3$)Me$_2$Ge-Cp)(NHiBu)$_3$, Zr((CF$_3$)Me$_2$Ge-Cp)(NsBu$_2$)$_3$, Zr((CF$_3$)Me$_2$Ge-Cp)(NHsBu)$_3$, Zr((CF$_3$)Me$_2$Ge-Cp)(NtBu$_2$)$_3$, or Zr((CF$_3$)Me$_2$Ge-Cp)(NHtBu)$_3$.

Exemplary Germanium- and Zirconium-containing precursors of Formula II include but are not limited to Zr(TMG-Cp)(OMe)$_3$, Zr(TMG-Cp)(OEt)$_3$, Zr(TMG-Cp)(OnPr)$_3$, Zr(TMG-Cp)(OiPr)$_3$, Zr(TMG-Cp)(OtBu)$_3$, Zr(TMG-Cp)(OsBu)$_3$, Zr(TMG-Cp)(OnBu)$_3$, Zr(TMG-Cp)(OiBu)$_3$, Zr(DMG-Cp)(OMe)$_3$, Zr(DMG-Cp)(OEt)$_3$, Zr(DMG-Cp)(OnPr)$_3$, Zr(DMG-Cp)(OiPr)$_3$, Zr(DMG-Cp)(OtBu)$_3$, Zr(DMG-Cp)(OsBu)$_3$, Zr(DMG-Cp)(OnBu)$_3$, Zr(DMG-Cp)(OiBu)$_3$, Zr(F$_3$Ge-Cp)(OMe)$_3$, Zr(F$_3$Ge-Cp)(OEt)$_3$, Zr(F$_3$Ge-Cp)(OnPr)$_3$, Zr(F$_3$Ge-Cp)(OiPr)$_3$, Zr(F$_3$Ge-Cp)(OtBu)$_3$, Zr(F$_3$Ge-Cp)(OsBu)$_3$, Zr(F$_3$Ge-Cp)(OnBu)$_3$, Zr(F$_3$Ge-Cp)(OiBu)$_3$, Zr(F$_2$HGe-Cp)(OMe)$_3$, Zr(F$_2$HGe-Cp)(OEt)$_3$, Zr(F$_2$HGe-Cp)(OnPr)$_3$, Zr(F$_2$HGe-Cp)(OiPr)$_3$, Zr(F$_2$HGe-Cp)(OtBu)$_3$, Zr(F$_2$HGe-Cp)(OsBu)$_3$, Zr(F$_2$HGe-Cp)(OnBu)$_3$, Zr(F$_2$HGe-Cp)(OiBu)$_3$, Zr(FH$_2$Ge-Cp)(OMe)$_3$, Zr(FH$_2$Ge-Cp)(OEt)$_3$, Zr(FH$_2$Ge-Cp)(OnPr)$_3$, Zr(FH$_2$Ge-Cp)(OiPr)$_3$, Zr(FH$_2$Ge-Cp)(OtBu)$_3$, Zr(FH$_2$Ge-Cp)(OsBu)$_3$, Zr(FH$_2$Ge-Cp)(OnBu)$_3$, Zr(FH$_2$Ge-Cp)(OiBu)$_3$, Zr(FMe$_2$Ge-Cp)(OMe)$_3$, Zr(FMe$_2$Ge-Cp)(OEt)$_3$, Zr(FMe$_2$Ge-Cp)(OnPr)$_3$, Zr(FMe$_2$Ge-Cp)(OiPr)$_3$, Zr(FMe$_2$Ge-Cp)(OtBu)$_3$, Zr(FMe$_2$Ge-Cp)(OsBu)$_3$, Zr(FMe$_2$Ge-Cp)(OnBu)$_3$, Zr(FMe$_2$Ge-Cp)(OiBu)$_3$, Zr((CF$_3$)$_3$Ge-Cp)(OMe)$_3$, Zr((CF$_3$)$_3$Ge-Cp)(OEt)$_3$, Zr((CF$_3$)$_3$Ge-Cp)(OnPr)$_3$, Zr((CF$_3$)$_3$Ge-Cp)(OiPr)$_3$, Zr((CF$_3$)$_3$Ge-Cp)(OtBu)$_3$, Zr((CF$_3$)$_3$Ge-Cp)(OsBu)$_3$, Zr((CF$_3$)$_3$Ge-Cp)(OnBu)$_3$, Zr((CF$_3$)$_3$Ge-Cp)(OiBu)$_3$, Zr((CF$_3$)$_2$HGe-Cp)(OMe)$_3$, Zr((CF$_3$)$_2$HGe-Cp)(OEt)$_3$, Zr((CF$_3$)$_2$HGe-Cp)(OnPr)$_3$, Zr((CF$_3$)$_2$HGe-Cp)(OiPr)$_3$, Zr((CF$_3$)$_2$HGe-Cp)(OtBu)$_3$, Zr((CF$_3$)$_2$HGe-Cp)(OsBu)$_3$, Zr((CF$_3$)$_2$HGe-Cp)(OnBu)$_3$, Zr((CF$_3$)$_2$HGe-Cp)(OiBu)$_3$, Zr((CF$_3$)Me$_2$Ge-Cp)(OMe)$_3$, Zr((CF$_3$)Me$_2$Ge-Cp)(OEt)$_3$, Zr((CF$_3$)Me$_2$Ge-Cp)(OnPr)$_3$, Zr((CF$_3$)Me$_2$Ge-Cp)(OiPr)$_3$, Zr((CF$_3$)Me$_2$Ge-Cp)(OtBu)$_3$, Zr((CF$_3$)Me$_2$Ge-Cp)(OsBu)$_3$, Zr((CF$_3$)Me$_2$Ge-Cp)(OnBu)$_3$, or Zr((CF$_3$)Me$_2$Ge-Cp)(OiBu)$_3$.

Preferably, the Germanium- and Zirconium-containing precursor is (trimethylgermyl)cyclopentadienyl tris(dimethylamino)Zirconium(IV), due to its vaporization results in atmospheric thermo gravimetric analysis, leaving a small amount of final residue (see Example 1).

The disclosed Germanium- and Zirconium-film forming compositions may be synthesized by reacting the corresponding tetrakis(amino)Zirconium(IV) or corresponding tetrakis(alkoxy) Zirconium(IV) with the corresponding (germyl)cyclopentadiene in a suitable solvent, such as toluene, THF or ether. (Germyl)cyclopentadiene are typically prepared according to the procedure described in Organometallics 1990, 9, 2488-2492. Alternatively the disclosed (germyl)cyclopentadienyl-tris(alkoxy)Zirconium-containing compounds may be synthesized by alcoholysis of the corresponding (germyl)cyclopentadienyl-tris(amino)Zirconium-containing compounds with 3 equivalents of the corresponding alcohol in a suitable solvent, such as toluene, THF or ether. Exemplary synthesis method containing further details are provided in the Examples that follow.

Purity of the disclosed Germanium- and Zirconium-film forming compositions is higher than 95% w/w, preferably higher than 98% w/w, and more preferably higher than 99% w/w. One of ordinary skill in the art will recognize that the purity may be determined by H NMR or gas or liquid chromatography with mass spectrometry. The disclosed Germanium- and Zirconium-film forming compositions may contain any of the following impurities: cyclopentadiene; (germyl)cyclopentadiene; dicyclopentadiene; alkylgermane; alkylamines such as tertbutylamine; dialkylamines such as dimethylamine; alkylimines; alcohol such as isopropylalcohol or tertbutylalcohol; THF; ether; pentane; cyclohexane; heptanes; toluene; chlorinated metal compounds; lithium, sodium or potassium alkoxy; lithium, sodium, or potassium alkylamino; or lithium, sodium, or potassium cyclopentadienyl. The total quantity of these impurities is below 5% w/w, preferably below 2% w/w, and more preferably below 1% w/w. The composition may be purified by recrystallisation, sublimation, distillation, and/or passing the gas or liquid through a suitable adsorbent, such as a 4A molecular sieve.

Purification of the disclosed Germanium- and Zirconium-film forming compositions may also result in metal impurities at the 0 ppbw (parts per billion weight) to 1 ppmw (parts per million weight) levels, preferably 0-500 ppbw level. These metal impurities include, but are not limited to, Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), Vanadium (V) and Zinc (Zn).

Also disclosed are methods for forming Zirconium-containing layers on a substrate using a vapor deposition process. The method may be useful in the manufacture of semiconductor, photovoltaic, LCD-TFT, or flat panel type devices. The disclosed Germanium- and Zirconium-film forming compositions may be used to deposit thin Zirconium-containing films using any deposition methods known to those of skill in the art.

Examples of suitable deposition methods include, without limitation, chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD), atmospheric pressure CVD (APCVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably ALD, PE-ALD, or spatial ALD in order to provide suitable step coverage and film thickness control.

The cubic/tetragonal crystalline phase of $ZrO_2$ provides the highest dielectric constant of the different $ZrO_2$ crystalline forms (cubic, tetragonal, amorphous, monoclinic, orthorhombic, and combinations thereof are the available crystalline phases). It is experimentally reported that a doping level (3-12%) of small ionic radius tetravalent dopant such as Ge is the most efficient in stabilizing the tetragonal zirconia phase. The substitution of a Zr atom by Ge in the tetragonal $ZrO_2$ structure results in reduced Ge—O bond with length similar to that in $GeO_2$. Therefore, $ZrO_2$ is an excellent host for Ge, which is easily incorporated into the "friendly" local environment of the oxide (J. Appl. Phys. 106, 024107, 2009). The advantage is that Ge is tetravalent therefore it substitutes Zr in the lattice without introducing O vacancies.

Applicants believe that the vapor deposition process conditions may be controlled so that Zr alone or both Zr and Ge may be deposited in the zirconium-containing layer. For instance, adjusting the ALD parameters to exhibit some parasitic CVD might be useful to deposit a finite amount of Ge in the $ZrO_2$ layer. Alternatively, the germanium content in $ZrO_2$ film may be controlled by alternating the deposition of $(Zr, Ge)O_2$ film using the disclosed Germanium- and Zirconium-film forming compositions and the deposition of pure $ZrO_2$ using another zirconium-containing precursor. For example, $ZrCp(NMe_2)_3$, $Zr(MeCp)(NMe_2)_3$ or $Zr(EtCp)(NMe_2)_3$ may serve as the Zr-containing precursor to produce pure $ZrO_2$ films. In other words x subcycles of $(Zr, Ge)O_2$ deposition using the Germanium- and Zirconium-film forming compositions may be alternated with y subcycles of pure $ZrO_2$ deposition using a zirconium-containing precursor, such as $ZrCp(NMe_2)_3$. The supercycle consisting of x subcycles of $(Zr, Ge)O_2$ and y subcycles of pure $ZrO_2$ may be repeated to obtain a desired thickness of $(Zr, Ge)O_2$ film, wherein x and y are integers which inclusively range from 1 to 20. Zr and Ge content may be controlled by adjusting x and y.

Alternatively, the germanium content in the $ZrO_2$ film may be controlled by depositing the $(Zr, Ge)O_2$ film using a mixture containing both the disclosed Germanium- and Zirconium-film forming compositions and a zirconium-containing precursor. For example, $ZrCp(NMe_2)_3$, $Zr(MeCp)(NMe_2)_3$, $Zr(EtCp)(NMe_2)_3$, $Zr(iPrCp)(NMe_2)_3$, or $Zr(tBuCp)(NMe_2)_3$ may serve as the Zr-containing precursor. The Zr and Ge content may be controlled by adjusting the ratio between the Germanium- and Zirconium-film forming composition and the zirconium-containing precursor in the mixture.

The disclosed Germanium- and Zirconium-film forming compositions may be supplied either in neat form or in a blend with a suitable solvent, such as ethyl benzene, xylene, mesitylene, decane, or dodecane. The disclosed compositions may be present in varying concentrations in the solvent.

The neat or blended Germanium- and Zirconium-film forming compositions are introduced into a reactor in vapor form by conventional means, such as tubing and/or flow meters. The composition in vapor form may be produced by vaporizing the neat or blended composition through a conventional vaporization step such as direct vaporization, distillation, direct liquid injection, by bubbling, or by using a sublimator such as the one disclosed in PCT Publication WO2009/087609 to Xu et al. The neat or blended composition may be fed in liquid state to a vaporizer where it is vaporized before it is introduced into the reactor. Alternatively, the neat or blended composition may be vaporized by passing a carrier gas into a container containing the compound or by bubbling the carrier gas into the composition. The carrier gas may include, but is not limited to, Ar, He, $N_2$, and mixtures thereof. Bubbling with a carrier gas may also remove any dissolved oxygen present in the neat or blended composition. The carrier gas and composition are then introduced into the reactor as a vapor.

If necessary, the container of disclosed composition may be heated to a temperature that permits the compound to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor, or other types of deposition systems under conditions suitable to cause the compounds to react and form the layers.

Generally, the reactor contains the substrate(s) onto which the thin films will be deposited. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combination thereof. Additionally, the wafers may include copper layers, tungsten layers, or noble metal layers (e.g., platinum, palladium rhodium, or gold). Plastic layers, such as poly(3,4-ethylenedioxythiophene) poly (styrenesulfonate) [PEDOT:PSS], may also be used. The layers may be planar or patterned. The disclosed processes may deposit the Zr-containing layer directly on the wafer or directly on one or more than one (when patterned layers from the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. For example, a $ZrO_2$ film may be deposited onto a TiN substrate. In subsequent processing, a TiN layer may be deposited on the $ZrO_2$ layer, forming a $TiN/ZrO_2/TiN$ stack used as DRAM capacitor.

The temperature and the pressure within the reactor are held at conditions suitable for vapor depositions. In other words, after introduction of the vaporized composition into the chamber, conditions within the chamber are such that at least part of the vaporized precursor is deposited onto the substrate to form a Zirconium-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 150° C. and about 400° C. One of ordinary skill in the art will recognize that "at least part of the vaporized precursor is deposited" means that some or all of the precursor reacts with or adheres to the substrate.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 150° C. to approximately 400° C. Alternatively, when a thermal process is performed, the deposition temperature may range from approximately 200° C. to approximately 500° C.

In addition to the disclosed compound, a reactant may also be introduced into the reactor. The reactant may be an oxidizing gas such as one of $O_2$, $O_3$, $H_2O$, $H_2O_2$, NO, $N_2O$, $NO_2$, oxygen-containing radicals such as O. or OH., NO, $NO_2$, carboxylic acids, formic acid, acetic acid, propionic acid, and mixtures thereof. Preferably, the oxidizing gas is selected from the group consisting of $O_2$, $O_3$, $H_2O$, $H_2O_2$, oxygen-containing radicals thereof such as O. or OH., and mixtures thereof.

Alternatively, the reactant may be a reducing gas such as one of $H_2$, $H_2CO$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminium, dimethylzinc, diethylzinc, radical species thereof, and mixtures thereof. Preferably, the reducing as is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof.

The reactant may be treated by plasma, in order to decompose the reactant into its radical form. $N_2$ may also be utilized as a reducing gas when treated with plasma. For instance, the plasma may be generated with a power ranging from about 50 W to about 500 W, preferably from about 100 W to about 400 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

For example, the reactant may be introduced into a direct plasma reactor, which generates plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of the reactant. In-situ plasma is typically a 13.56 MHz RF inductively coupled plasma that is generated between the showerhead and the substrate holder. The substrate or the showerhead may be the powered electrode depending on whether positive ion impact occurs. Typical applied powers in in-situ plasma generators are from approximately 30 W to approximately 1000 W. Preferably, powers from approximately 30 W to approximately 600 W are used in the disclosed methods. More preferably, the powers range from approximately 100 W to approximately 500 W. The disassociation of the reactant using in-situ plasma is typically less than achieved using a remote plasma source for the same power input and is therefore not as efficient in reactant disassociation as a remote plasma system, which may be beneficial for the deposition of Zirconium-containing films on substrates easily damaged by plasma.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 0.5 Torr to approximately 10 Torr, the reactant $O_2$ may be decomposed into two O. radicals. Preferably, the remote plasma may be generated with a power ranging from about 1 kW to about 10 kW, more preferably from about 2.5 kW to about 7.5 kW.

The vapor deposition conditions within the chamber allow the disclosed precursors and the reactant to react and form a Zirconium-containing film on the substrate. In some embodiments, Applicants believe that plasma-treating the reactant may provide the reactant with the energy needed to react with the disclosed precursor.

Depending on what type of film is desired to be deposited, an additional precursor compound may be introduced into the reactor. The additional precursor may be used to provide the same (i.e., Zr) or additional elements to the Zirconium-containing film. The additional elements may include Hafnium, Niobium, Tantalum, lanthanides (Ytterbium, Erbium, Dysprosium, Gadolinium, Praseodymium, Cerium, Lanthanum, Yttrium), germanium, silicon, titanium, manganese, cobalt, nickel, ruthenium, bismuth, lead, magnesium, aluminum, or mixtures of these. When an additional precursor compound is utilized, the resultant film deposited on the substrate may contain the Zirconium in combination with at least one additional element.

The Germanium- and Zirconium-film forming compositions and reactants may be introduced into the reactor either simultaneously (chemical vapor deposition), sequentially (atomic layer deposition), or different combinations thereof. The reactor may be purged with an inert gas between the introduction of the composition and the introduction of the reactant. Alternatively, the reactant and the composition may be mixed together to form a reactant/composition mixture, and then introduced to the reactor in mixture form. Another example is to introduce the reactant continuously and to introduce the Germanium- and Zirconium-film forming composition by pulse (pulsed chemical vapor deposition).

The vaporized composition and the reactant may be pulsed sequentially or simultaneously (e.g. pulsed CVD) into the reactor. Each pulse of composition may last for a time period ranging from about 0.01 seconds to about 10 seconds, alternatively from about 0.3 seconds to about 3 seconds, alternatively from about 0.5 seconds to about 2 seconds. In another embodiment, the reactant may also be pulsed into the reactor. In such embodiments, the pulse of each gas may last for a time period ranging from about 0.01 seconds to about 10 seconds, alternatively from about 0.3 seconds to about 3 seconds, alternatively from about 0.5 seconds to about 2 seconds. In another alternative, the vaporized composition and one or more reactants may be simultaneously sprayed from a shower head under which a susceptor holding several wafers is spun (spatial ALD).

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film thickness.

In one non-limiting exemplary CVD type process, the vapor phase of the disclosed Germanium- and Zirconium-film forming composition and a reactant are simultaneously introduced into the reactor. The two react to form the resulting Zirconium-containing thin film. When the reactant in this exemplary CVD process is treated with plasma, the exemplary CVD process becomes an exemplary PECVD process. The reactant may be treated with plasma prior or subsequent to introduction into the chamber.

In one non-limiting exemplary ALD type process, the vapor phase of the disclosed Germanium- and Zirconium-film forming composition is introduced into the reactor, where it is contacted with a suitable substrate. Excess composition may then be removed from the reactor by purging and/or evacuating the reactor. A desired gas (for example, $H_2$) is introduced into the reactor where it reacts with the absorbed composition in a self-limiting manner. Any excess reducing gas is removed from the reactor by purging and/or evacuating the reactor. If the desired film is a Zirconium film, this two-step process may provide the desired film thickness or may be repeated until a film having the necessary thickness has been obtained.

Alternatively, if the desired film contains Zirconium and a second element, the two-step process above may be followed by introduction of the vapor of an additional precursor compound into the reactor. The additional precursor compound will be selected based on the nature of the Zirconium film being deposited. After introduction into the reactor, the additional precursor compound is contacted with the substrate. Any excess precursor compound is removed from the reactor by purging and/or evacuating the reactor. Once again, a desired gas may be introduced into the reactor to react with the precursor compound. Excess gas is removed from the reactor by purging and/or evacuating the reactor. If a desired film thickness has been achieved, the process may be terminated. However, if a thicker film is desired, the entire four-step process may be repeated. By alternating the provision of the Germanium- and Zirconium-film forming composition, additional precursor compound, and reactant, a film of desired composition and thickness can be deposited.

When the reactant in this exemplary ALD process is treated with plasma, the exemplary ALD process becomes an exemplary PEALD process. The reactant may be treated with plasma prior or subsequent to introduction into the chamber.

In a second non-limiting exemplary ALD type process, the vapor phase of one of the disclosed Ge- and Zr-film forming compositions, for example (trimethylgermyl)cyclopentadienyl tris(dimethylamino) Zirconium(IV), is introduced into the reactor, where it is contacted with a TiN substrate. Excess Ge- and Zr-film forming composition may then be removed from the reactor by purging and/or evacuating the reactor. A desired gas (for example, $O_3$) is introduced into the reactor where it reacts with the absorbed Ge- and Zr-film forming composition in a self-limiting manner to form a $ZrO_2$ or $(Zr, Ge)O_2$ film. Any excess oxidizing gas is removed from the reactor by purging and/or evacuating the reactor. These two steps may be repeated until the $ZrO_2$ or $(Zr, Ge)O_2$ film obtains a desired thickness. A TiN layer may then be deposited on top of the $ZrO_2$ or $(Zr, Ge)O_2$ layer. The resulting TiN/$ZrO_2$/TiN or TiN/$(Zr, Ge)O_2$/TiN stack may be used in DRAM capacitors.

In a third non-limiting exemplary ALD type process, the vapor phase of one of the disclosed Ge- and Zr-film forming compositions, for example (trimethylgermyl)cyclopentadienyl tris(dimethylamino)Zirconium(IV), is introduced in a first step into the reactor, where it is contacted with a TiN substrate. Excess Ge- and Zr-film forming composition may then be removed from the reactor by purging and/or evacuating the reactor. A desired gas (for example, $O_3$) is introduced into the reactor where it reacts with the absorbed Ge- and Zr-containing precursor in a self-limiting manner to form a $(Zr, Ge)O_2$ film. Any excess oxidizing gas is removed from the reactor by purging and/or evacuating the reactor. These two steps may be considered as a subcycle and may be repeated x times to obtain a desired thickness of the $(Zr, Ge)O_2$ film. In a second step the vapor phase of a Zr-containing precursor, for example (methyl)cyclopentadienyl tris(dimethylamino)Zirconium(IV) or (ethyl)cyclopentadienyl tris(dimethylamino)Zirconium(IV) is introduced into the same reactor. Excess Zr-containing precursor may then be removed from the reactor by purging and/or evacuating the reactor. A desired gas (for example, $O_3$) is introduced into the reactor where it reacts with the Zr-containing precursor in a self-limiting manner to form a $ZrO_2$ film. Any excess oxidizing gas is removed from the reactor by purging and/or evacuating the reactor. These two steps may be considered as a subcycle and may be repeated y times to obtain a desired thickness of pure $ZrO_2$ film. The supercycle consisting of x subcycles of $(Zr, Ge)O_2$ and y subcycles of pure $ZrO_2$ may be be repeated to obtain a desired thickness of $(Zr, Ge)O_2$ film. Zr and Ge content may be controlled by adjusting the number of x and y cycles (x and y may independently range from 1 to 20). A TiN layer may then be deposited on top of the $ZrO_2$ or $(Zr, Ge)O_2$ layer. The resulting TiN/$ZrO_2$/TiN or TiN/$(Zr, Ge)O_2$/TiN stack may be used in DRAM capacitors.

In a fourth non-limiting exemplary ALD type process, the vapor phase of a mixture containing the disclosed Ge- and Zr-film forming composition, for example (trimethylgermyl) cyclopentadienyl tris(dimethylamino)Zirconium(IV), and a Zr-containing precursor, for example (isopropyl)cyclopentadienyl tris(dimethylamino)Zirconium(IV) or (tertbutyl)cyclopentadienyl tris(dimethylamino)Zirconium(IV), is introduced into the reactor, where it is contacted with a substrate, for example TiN, NbN, Ru, $TiO_2$, $MoO_2$ or $MoO_3$. Excess mixture may then be removed from the reactor by purging and/or evacuating the reactor. A desired gas (for example, $O_3$) is introduced into the reactor where it reacts with the absorbed mixture in a self-limiting manner to form a $(Zr, Ge)O_2$ film. Any excess oxidizing gas is removed from the reactor by purging and/or evacuating the reactor. These two steps may be repeated until the $(Zr, Ge)O_2$ film obtains a desired thickness. The Zr and Ge content may be controlled by adjusting the ratio between the Germanium- and Zirconium-film forming composition and the zirconium-containing precursor in the mixture. A TiN layer may be deposited on top of the $(Zr, Ge)O_2$ layer. The resulting TiN/$ZrO_2$/TiN or TiN/$(Zr, Ge)O_2$/TiN stack may be used in DRAM capacitors.

The Zirconium-containing films resulting from the processes discussed above may include a pure Zirconium, Zirconium silicide ($Zr_kSi_l$), Zirconium oxide ($Zr_mO_n$), Germanium-doped Zirconium oxide ($Zr_rGe_sO_t$), Zirconium nitride (ZOO, or germanium-doped silicon nitride ($Zr_tGe_u N_v$), wherein k, l, m, n, o, p, q, r, s, t, u and v are integers which inclusively range from 1 to 6. One of ordinary skill in the art will recognize that by judicial selection of the appropriate disclosed compound, optional precursor compounds, and reactant species, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the Zirconium-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds under a H-containing atmosphere or an O-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the Zirconium-containing film. This in turn tends to improve the resistivity of the film.

EXAMPLES

The following examples illustrate experiments performed in conjunction with the disclosure herein. The examples are not intended to be all inclusive and are not intended to limit the scope of disclosure described herein.

Example 1

(trimethylgermyl)cyclopentadienyl tris(dimethylamino) Zirconium(IV) synthesis [Zr(TMG-Cp)(NMe$_2$)$_3$]

To a solution of Zr(NMe$_2$)$_4$ (1.33 g, 0.005 mol) in ca. 20 mL of toluene at room temperature, was added dropwise a freshly distilled TMGCpH (0.93 g, 0.005 mol). The mixture was stirred overnight. Solvent was then removed under vacuum to give yellow oil. The material was then purified by distillation at 120° C.@6 mTorr to give 1.38 g (68%) of pure yellow oil. The NMR$^1$H spectrum is provided in FIG. 1. NMR$^1$H (δ, ppm, C6D6): 6.28 (t, 2H), 6.23 (t, 2H), 2.95 (s, 18H), 0.38 (s, 9H).

Figure 3:
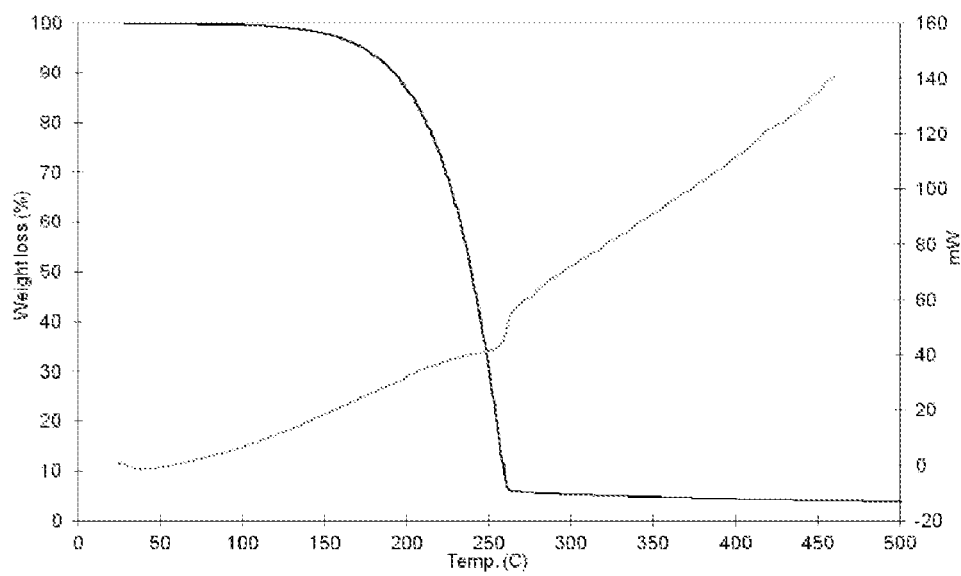
FIG. 3 is a ThermoGravimetric Analysis (TGA)/Differential Thermal Analysis (DTA) graph demonstrating the percentage of weight loss (TGA) or the differential temperature (DTA) with increasing temperature of Zr(TMGCp)(NMe$_2$)$_3$.

The oil left a 3.9% residual mass during TGA analysis measured at a temperature rising rate of 10° C./min in an atmosphere which flows nitrogen at 200 mL/min. These results are shown in FIG. 3, which is a TGA/DTA graph illustrating the percentage of weight loss (TGA) and differential temperature (DTA) upon temperature increase.

Example 2

(trimethylgermyl)cyclopentadienyl tris(isopropoxy) Zirconium(IV) synthesis [Zr(TMG-Cp)(OiPr)$_3$]

Figure 2:
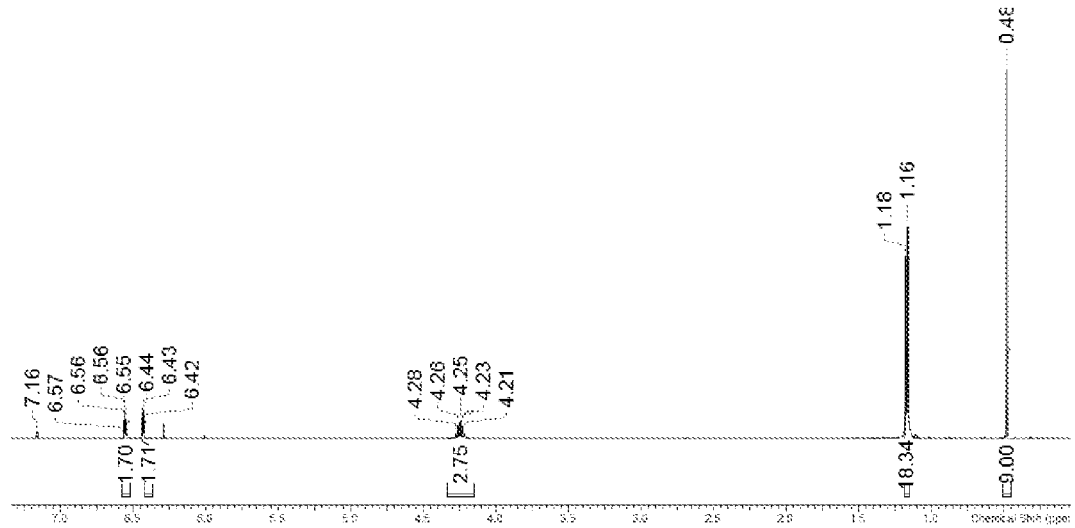
FIG. 2 is a $^1$HNMR spectrum of Zr(TMGCp)(OiPr)$_3$.

To a solution of Zr(TMGCp)(NMe$_2$)$_3$ (1.26 g, 2.8 mmol) in ca. 20 mL of THF, was added drop wise anhydrous isopropanol (0.63 g, 10.5 mmol). The mixture was stirred overnight at room temperature. Solvent was then removed under vacuum to give bright yellow oil. The material was then purified by distillation at 90° C.@20 mTorr to give 0.39 g (31%) of pure slightly yellow oil. The NMR$^1$H spectrum is provided in FIG. 2. NMR$^1$H (δ, ppm, C6D6): 6.56 (t, 2H), 6.43 (t, 2H), 4.25 (m, 3H), 1.17 (d, 18H), 0.48 (s, 9H).

Figure 4:
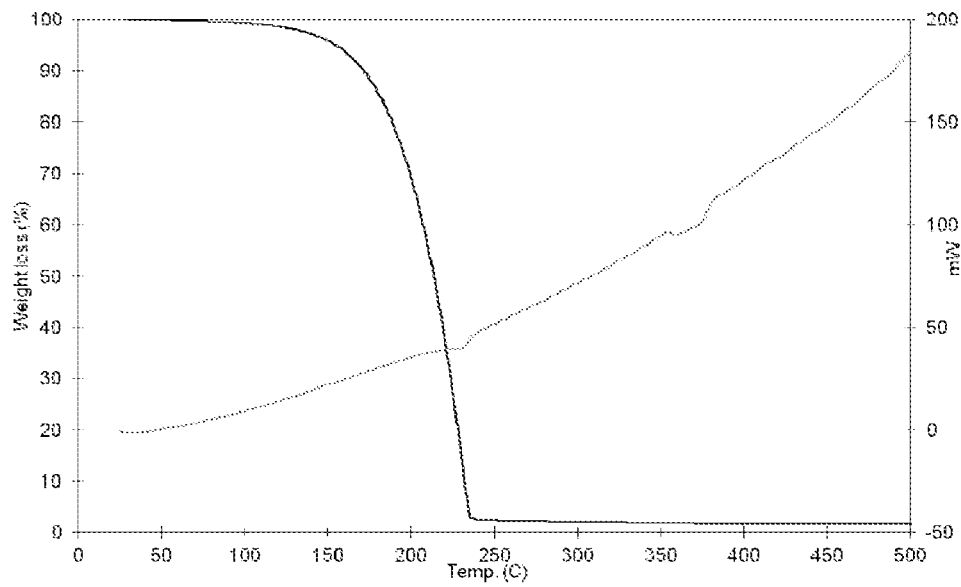
FIG. 4 is a TGA/DTA graph demonstrating the percentage of weight loss (TGA) or the differential temperature (DTA) with increasing temperature of Zr(TMGCp)(OiPr)$_3$.

The oil left a 1.6% residual mass during TGA analysis measured at a temperature rising rate of 10° C./min in an atmosphere which flows nitrogen at 200 mL/min. These results are shown in FIG. 4, which is a TGA/DTA graph illustrating the percentage of weight loss (TGA) and differential temperature (DTA) upon temperature increase.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:
1. A Germanium- and Zirconium-film forming composition comprising a precursor having one of the following formulae:

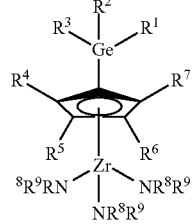

Formula I

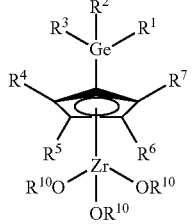

Formula II wherein each $R^1$, $R^2$, $R^3$, $R^4$, $R^5$, $R^6$, $R^7$, $R^8$, $R^9$ and $R^{10}$ is independently selected from the group consisting of H; a C1-C5 linear, branched, or cyclic alkyl group; and a C1-C5 linear, branched, or cyclic fluoroalkyl group.

2. The Germanium- and Zirconium-film forming composition of claim 1, having the Formula I:

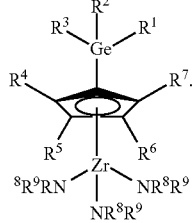

Formula I

3. The Germanium- and Zirconium-film forming composition of claim 2, wherein the precursor is selected from the group consisting of: (trimethylgermyl)cyclopentadienyl tris(Dimethylamino)Zirconium(IV) (Zr(TMG-Cp)(NMe$_2$)$_3$); (trimethylgermyl)cyclopentadienyl tris(methylamino) Zirconium(IV) (Zr(TMG-Cp)(NHMe)$_3$); (trimethylgermyl)cyclopentadienyl tris(Diethylamino)Zirconium(IV) (Zr(TMG-Cp)(NEt$_2$)$_3$); (trimethylgermyl)cyclopentadienyl tris(ethylamino)Zirconium(IV) (Zr(TMG-Cp)(NHEt)$_3$); (trimethylgermyl)cyclopentadienyl tris(ethylmethylamino) Zirconium(IV) (Zr(TMG-Cp)(NEtMe)$_3$); (trimethylgermyl) cyclopentadienyl tris(Di n-propylamino)Zirconium(IV) (Zr(TMG-Cp)(NnPr$_2$)$_3$); (trimethylgermyl)cyclopentadienyl tris(n-propylamino)Zirconium(IV) (Zr(TMG-Cp)(NHnPr)$_3$); (trimethylgermyl)cyclopentadienyl tris(Di isopropylamino)Zirconium(IV) (Zr(TMG-Cp)(NiPr$_2$)$_3$); (trimethylgermyl)cyclopentadienyl tris(isopropylamino)Zirconium(IV) (Zr(TMG-Cp)(NH iPr)$_3$); (trimethylgermyl) cyclopentadienyl tris(Di n-butylamino)Zirconium(IV) (Zr(TMG-Cp)(NnBu$_2$)$_3$); (trimethylgermyl)cyclopentadienyl tris(n-butylamino)Zirconium(IV) (Zr(TMG-Cp)(NHnBu)$_3$) (trimethylgermyl)cyclopentadienyl tris(Di isobutylamino) Zirconium(IV) (Zr(TMG-Cp)(NiBu$_2$)$_3$); (trimethylgermyl) cyclopentadienyl tris(isobutylamino)Zirconium(IV) (Zr(TMG-Cp)(NHiBu)$_3$); (trimethylgermyl)cyclopentadienyl tris(Di sec-butylamino)Zirconium(IV) (Zr(TMG-Cp)(NsBu$_2$)$_3$); (trimethylgermyl)cyclopentadienyl tris(sec-butylamino)Zirconium(IV) (Zr(TMG-Cp)(NHsBu)$_3$); (trimethylgermyl)cyclopentadienyl tris(Di tert-butylamino) Zirconium(IV) (Zr(TMG-Cp)(NtBu$_2$)$_3$); (trimethylgermyl) cyclopentadienyl tris(tert-butylamino)Zirconium(IV) (Zr(TMG-Cp)(NHtBu)$_3$); (dimethylgermyl)cyclopentadienyl tris(Dimethylamino)Zirconium(IV) (Zr(DMG-Cp)(NMe$_2$)$_3$); (dimethylgermyl)cyclopentadienyl tris(methylamino)Zirconium(IV) (Zr(DMG-Cp)(NHMe)$_3$); (dimethylgermyl)cyclopentadienyl tris(Diethylamino)Zirconium(IV) (Zr(DMG-Cp)(NEt$_2$)$_3$); (dimethylgermyl)cyclopentadienyl tris(ethylamino)Zirconium(IV) (Zr(DMG-Cp)(NHEt)$_3$); (dimethylgermyl)cyclopentadienyl tris(ethylmethylamino) Zirconium(IV) (Zr(DMG-Cp)(NEtMe)$_3$); (dimethylgermyl)cyclopentadienyl tris(Di n-propylamino)Zirconium(IV) (Zr(DMG-Cp)(NnPr$_2$)$_3$); (dimethylgermyl)cyclopentadienyl tris(n-propylamino)Zirconium(IV) (Zr(DMG-Cp)(NHnPr)$_3$); (dimethylgermyl)cyclopentadienyl tris(Di isopropylamino)Zirconium(IV) (Zr(DMG-Cp)(NiPr$_2$)$_3$); (dimethylgermyl)cyclopentadienyl tris(isopropylamino)Zirconium(IV) (Zr(DMG-Cp)(NHiPr)$_3$); (dimethylgermyl) cyclopentadienyl tris(Di n-butylamino)Zirconium(IV) (Zr(DMG-Cp)(NnBu$_2$)$_3$); (dimethylgermyl)cyclopentadienyl tris(n-butylamino)Zirconium(IV) (Zr(DMG-Cp)(NHnBu)$_3$); (dimethylgermyl)cyclopentadienyl tris(Di isobutylamino)Zirconium(IV) (Zr(DMG-Cp)(NiBu$_2$)$_3$); (dimethylgermyl)cyclopentadienyl tris(isobutylamino)Zirconium(IV) (Zr(DMG-Cp)(NHiBu)$_3$); (dimethylgermyl)cyclopentadienyl tris(Di sec-butylamino)Zirconium(IV) (Zr(DMG-Cp)(NsBu$_2$)$_3$); (dimethylgermyl)cyclopentadienyl tris(sec-butylamino)Zirconium(IV) (Zr(DMG-Cp)(NHsBu)$_3$); (dimethylgermyl)cyclopentadienyl tris(Di tert-butylamino)Zirconium(IV) (Zr(DMG-Cp)(NtBu$_2$)$_3$); (dimethylgermyl)cyclopentadienyl tris(tert-butylamino)Zirconium(IV) (Zr(DMG-Cp)(NHtBu)$_3$); (trifluorogermyl) cyclopentadienyl tris(Dimethylamino)Zirconium(IV) (Zr(F$_3$Ge-Cp)(NMe$_2$)$_3$); (trifluorogermyl)cyclopentadienyl tris (methylamino)Zirconium(IV) (Zr(F$_3$Ge-Cp)(NHMe)$_3$); (trifluorogermyl)cyclopentadienyl tris(Diethylamino) Zirconium(IV) (Zr(F$_3$Ge-Cp)(NEt$_2$)$_3$); (trifluorogermyl)cyclopentadienyl tris(ethylamino)Zirconium(IV) (Zr(F$_3$Ge-Cp)(NHEt)$_3$); (trifluorogermyl)cyclopentadienyl tris(Ethylmethylamino)Zirconium(IV) (Zr(F$_3$Ge-Cp)(NEtMe)$_3$); (trifluorogermyl)cyclopentadienyl tris(Di n-propylamino)Zirconium(IV) (Zr(F$_3$Ge-Cp)(NnPr$_2$)$_3$); (trifluorogermyl)cyclopentadienyl tris(n-propylamino)Zirconium (IV) (Zr(F$_3$Ge-Cp)(NHnPr)$_3$) (trifluorogermyl) cyclopentadienyl tris(Di isopropylamino)Zirconium(IV) (Zr(F$_3$Ge-Cp)(NiPr$_2$)$_3$); (trifluorogermyl)cyclopentadienyl tris(isopropylamino)Zirconium(IV) (Zr(F$_3$Ge-Cp)(NHiPr)$_3$); (trifluorogermyl)cyclopentadienyl tris(Di n-butylamino)Zirconium(IV) (Zr(F$_3$Ge-Cp)(NnBu$_2$)$_3$); (trifluorogermyl)cyclopentadienyl tris(n-butylamino)Zirconium(IV) (Zr(F$_3$Ge-Cp)(NHnBu)$_3$); (trifluorogermyl)cyclopentadienyl tris(Di isobutylamino)Zirconium(IV) (Zr(F$_3$Ge-Cp)(NiBu$_2$)$_3$); (trifluorogermyl)cyclopentadienyl tris(isobutylamino)Zirconium(IV) (Zr(F$_3$Ge-Cp)(NHiBu)$_3$); (trifluorogermyl)cyclopentadienyl tris(Di sec-butylamino)Zirconium(IV) (Zr(F$_3$Ge-Cp)(NsBu$_2$)$_3$); (trifluorogermyl)cyclopentadienyl tris(sec-butylamino)Zirconium(IV) (Zr(F$_3$Ge-Cp)(NHsBu)$_3$); (trifluorogermyl)cyclopentadienyl tris(Di tert-butylamino) Zirconium(IV) (Zr(F$_3$Ge-Cp)(NtBu$_2$)$_3$); (trifluorogermyl) cyclopentadienyl tris(tert-butylamino)Zirconium(IV) (Zr(F$_3$Ge-Cp)(NHtBu)$_3$); (difluorogermyl)cyclopentadienyl tris(Dimethylamino)Zirconium(IV) (Zr(F$_2$HGe-Cp)(NMe$_2$)$_3$); (difluorogermyl)cyclopentadienyl tris(methylamino)Zirconium(IV) (Zr(F$_2$HGe-Cp)(NHMe)$_3$); (difluorogermyl)cyclopentadienyl tris(Diethylamino)Zirconium(IV) (Zr(F$_2$HGe-Cp)(NEt$_2$)$_3$); (difluorogermyl)cyclopentadienyl tris(ethylamino)Zirconium(IV) (Zr(F$_2$HGe-Cp)(NHEt)$_3$); (difluorogermyl)cyclopentadienyl tris(Ethylmethylamino) Zirconium(IV) (Zr(F$_2$HGe-Cp)(NEtMe)$_3$); (difluorogermyl) cyclopentadienyl tris(Di n-propylamino)Zirconium(IV) (Zr(F$_2$HGe-Cp)(NnPr$_2$)$_3$); (difluorogermyl)cyclopentadienyl tris(n-propylamino)Zirconium(IV) (Zr(F$_2$HGe-Cp)(NHnPr)$_3$); (difluorogermyl)cyclopentadienyl tris(Di isopropylamino)Zirconium(IV) (Zr(F$_2$HGe-Cp)(NiPr$_2$)$_3$); (difluorogermyl)cyclopentadienyl tris(isopropylamino)Zirconium(IV) (Zr(F$_2$HGe-Cp)(NHiPr)$_3$); (difluorogermyl) cyclopentadienyl tris(Di n-butylamino)Zirconium(IV) (Zr(F$_2$HGe-Cp)(NnBu$_2$)$_3$); (difluorogermyl)cyclopentadienyl tris(n-butylamino)Zirconium(IV) (Zr(F$_2$HGe-Cp)(NHnBu)$_3$); (difluorogermyl)cyclopentadienyl tris(Di isobutylamino)Zirconium(IV) (Zr(F$_2$HGe-Cp)(NiBu$_2$)$_3$); (difluorogermyl)cyclopentadienyl tris(isobutylamino)Zirconium (IV) (Zr(F$_2$HGe-Cp)(NHiBu)$_3$); (difluorogermyl) cyclopentadienyl tris(Di sec-butylamino)Zirconium(IV) (Zr(F$_2$HGe-Cp)(NsBu$_2$)$_3$); (difluorogermyl)cyclopentadienyl tris(sec-butylamino)Zirconium(IV) (Zr(F$_2$HGe-Cp)(NHsBu)$_3$); (difluorogermyl)cyclopentadienyl tris(Di tert-butylamino)Zirconium(IV) (Zr(F$_2$HGe-Cp)(NtBu$_2$)$_3$); (difluorogermyl)cyclopentadienyl tris(tert-butylamino) Zirconium(IV) (Zr(F$_2$HGe-Cp)(NHtBu)$_3$); (monofluorogermyl)cyclopentadienyl tris(Dimethylamino) Zirconium(IV) (Zr(FH$_2$Ge-Cp)(NMe$_2$)$_3$); (monofluorogermyl)cyclopentadienyl tris(methylamino)Zirconium(IV) (Zr(FH$_2$Ge-Cp)(NHMe)$_3$); (monofluorogermyl) cyclopentadienyl tris(Diethylamino)Zirconium(IV) (Zr(FH$_2$Ge-Cp)(NEt$_2$)$_3$); (monofluorogermyl)cyclopentadienyl tris(ethylamino)Zirconium(IV) (Zr(FH$_2$Ge-Cp)(NHEO$_3$); (monofluorogermyl)cyclopentadienyl tris(Ethylmethylamino)Zirconium(IV) (Zr(FH$_2$Ge-Cp)(NEtMe)$_3$); (monofluorogermyl)cyclopentadienyl tris(Di n-propylamino)Zirconium(IV) (Zr(FH$_2$Ge-Cp)(NnPr$_2$)$_3$); (monofluorogermyl) cyclopentadienyl tris(n-propylamino)Zirconium(IV) (Zr(FH$_2$Ge-Cp)(NHnPr)$_3$); (monofluorogermyl) cyclopentadienyl tris(Diisopropylamino)Zirconium(IV) (Zr(FH$_2$Ge-Cp)(NiPr$_2$)$_3$); (monofluorogermyl) cyclopentadienyl tris(isopropylamino)Zirconium(IV) (Zr (FH₂Ge-Cp)(NHiPr)₃); (monofluorogermyl)cyclopentadienyl tris(Di n-butylamino)Zirconium(IV) (Zr(FH₂Ge-Cp)(NnBu₂)₃); (monofluorogermyl)cyclopentadienyl tris(n-butylamino)Zirconium(IV) (Zr(FH₂Ge-Cp)(NHnBu)₃); (monofluorogermyl)cyclopentadienyl tris(Di isobutylamino)Zirconium(IV) (Zr(FH₂Ge-Cp)(NiBu₂)₃) (monofluorogermyl)cyclopentadienyl tris(isobutylamino)Zirconium(IV) (Zr(FH₂Ge-Cp)(NHiBu)₃); (monofluorogermyl)cyclopentadienyl tris(Di sec-butylamino)Zirconium(IV) (Zr(FH₂Ge-Cp)(NsBu₂)₃); (monofluorogermyl)cyclopentadienyl tris(sec-butylamino)Zirconium(IV) (Zr(FH₂Ge-Cp)(NHsBO₃); (monofluorogermyl)cyclopentadienyl tris(Di tert-butylamino)Zirconium(IV) (Zr(FH₂Ge-Cp)(NtBu₂)₃); (monofluorogermyl)cyclopentadienyl tris(tert-butylamino)Zirconium(IV) (Zr(FH₂Ge-Cp)(NHtBu)₃); (fluoro dimethylgermyl)cyclopentadienyl tris(Dimethylamino) Zirconium(IV) (Zr(FMe₂Ge-Cp)(NMe₂)₃); (fluoro dimethylgermyl)cyclopentadienyl tris(methylamino)Zirconium(IV) (Zr(FMe₂Ge-Cp)(NHMe)₃); (fluoro dimethylgermyl)cyclopentadienyl tris(Diethylamino)Zirconium(IV) (Zr(FMe₂Ge-Cp)(NEt₂)₃); (fluoro dimethylgermyl)cyclopentadienyl tris(ethylamino)Zirconium(IV) (Zr(FMe₂Ge-Cp)(NHEt)₃); (fluoro dimethylgermyl)cyclopentadienyl tris(Ethylmethylamino)Zirconium(IV) (Zr(FMe₂Ge-Cp)(NEtMe)₃); (fluoro dimethylgermyl)cyclopentadienyl tris(Di n-propylamino) Zirconium(IV) (Zr(FMe₂Ge-Cp)(NnPr₂)₃); (fluoro dimethylgermyl)cyclopentadienyl tris(n-propylamino)Zirconium(IV) (Zr(FMe₂Ge-Cp)(NHnPr)₃); (fluoro dimethylgermyl)cyclopentadienyl tris(Diisopropylamino)Zirconium(IV) (Zr(FMe₂Ge-Cp)(NiPr₂)₃); (fluoro dimethylgermyl)cyclopentadienyl tris(isopropylamino) Zirconium(IV) (Zr(FMe₂Ge-Cp)(NHiPr)₃); (fluoro dimethylgermyl)cyclopentadienyl tris(Di n-butylamino)Zirconium(IV) (Zr(FMe₂Ge-Cp)(NnBu₂)₃); (fluoro dimethylgermyl)cyclopentadienyl tris(n-butylamino)Zirconium(IV) (Zr(FMe₂Ge-Cp)(NHnBu)₃); (fluoro dimethylgermyl)cyclopentadienyl tris(Di isobutylamino)Zirconium(IV) (Zr(FMe₂Ge-Cp)(NiBu₂)₃); (fluoro dimethylgermyl)cyclopentadienyl tris(isobutylamino) Zirconium(IV) (Zr(FMe₂Ge-Cp)(NHiBu)₃); (fluoro dimethylgermyl)cyclopentadienyl tris(Di sec-butylamino) Zirconium(IV) (Zr(FMe₂Ge-Cp)(NsBu₂)₃); (fluoro dimethylgermyl)cyclopentadienyl tris(sec-butylamino)Zirconium(IV) (Zr(FMe₂Ge-Cp)(NHsBu)₃); (fluoro dimethylgermyl)cyclopentadienyl tris(Di tert-butylamino)Zirconium(IV) (Zr(FMe₂Ge-Cp)(NtBu₂)₃); (fluoro dimethylgermyl)cyclopentadienyl tris(tert-butylamino) Zirconium(IV) (Zr(FMe₂Ge-Cp)(NHtBu)₃); (tris(trifluoromethyl)germyl)cyclopentadienyl tris(Dimethylamino) Zirconium(IV) (Zr((CF₃)₃Ge-Cp)(NMe₂)₃); (tris(trifluoromethyl)germyl)cyclopentadienyl tris(methylamino) Zirconium(IV) (Zr((CF₃)₃Ge-Cp)(NHMe)₃); (tris(trifluoromethyl)germyl)cyclopentadienyl tris(Diethylamino) Zirconium(IV) (Zr((CF₃)₃Ge-Cp)(NEt₂)₃); (tris(trifluoromethyl)germyl)cyclopentadienyl tris(ethylamino) Zirconium(IV) (Zr((CF₃)₃ Ge-Cp)(NHEt)₃); (tris(trifluoromethyl)germyl)cyclopentadienyl tris(Ethylmethylamino) Zirconium(IV) (Zr((CF₃)₃Ge-Cp)(NEtMe)₃); (tris(trifluoromethyl)germyl)cyclopentadienyl tris(Di n-propylamino) Zirconium(IV) (Zr((CF₃)₃Ge-Cp)(NnPr₂)₃); (tris(trifluoromethyl)germyl)cyclopentadienyl tris(n-propylamino) Zirconium(IV) (Zr((CF₃)₃Ge-Cp)(NHnPr)₃); (tris(trifluoromethyl)germyl)cyclopentadienyl tris(Diisopropylamino) Zirconium(IV) (Zr((CF₃)₃Ge-Cp)(NiPr₂)₃); (tris(trifluoromethyl)germyl)cyclopentadienyl tris(isopropylamino) Zirconium(IV) (Zr((CF₃)₃Ge-Cp)(NHiPr)₃); (tris(trifluoromethyl)germyl)cyclopentadienyl tris(Di n-butylamino) Zirconium(IV) (Zr((CF₃)₃Ge-Cp)(NnBu₂)₃); (tris(trifluoromethyl)germyl)cyclopentadienyl tris(n-butylamino) Zirconium(IV) (Zr((CF₃)₃ Ge-Cp)(NHnBu)₃); (tris(trifluoromethyl)germyl)cyclopentadienyl tris(Di isobutylamino) Zirconium(IV) (Zr((CF₃)₃Ge-Cp)(NiBu₂)₃); (tris(trifluoromethyl)germyl)cyclopentadienyl tris(isobutylamino) Zirconium(IV) (Zr((CF₃)₃Ge-Cp)(NHiBu)₃); (tris(trifluoromethyl)germyl)cyclopentadienyl tris(Di sec-butylamino) Zirconium(IV) (Zr((CF₃)₃Ge-Cp)(NsBu₂)₃); (tris(trifluoromethyl)germyl)cyclopentadienyl tris(sec-butylamino) Zirconium(IV) (Zr((CF₃)₃Ge-Cp)(NHsBu)₃); (tris(trifluoromethyl)germyl)cyclopentadienyl tris(Di tert-butylamino) Zirconium(IV) (Zr((CF₃)₃Ge-Cp)(NtBu₂)₃); (tris(trifluoromethyl)germyl)cyclopentadienyl tris(tert-butylamino) Zirconium(IV) (Zr((CF₃)₃Ge-Cp)(NHtBu)₃); (bis(trifluoromethyl)germyl)cyclopentadienyl tris(Dimethylamino) Zirconium(IV) (Zr((CF₃)₂HGe-Cp)(NMe₂)₃); (bis(trifluoromethyl)germyl)cyclopentadienyl tris(methylamino) Zirconium(IV) (Zr((CF₃)₂HGe-Cp)(NHMe)₃); (bis(trifluoromethyl)germyl)cyclopentadienyl tris(Diethylamino) Zirconium(IV) (Zr((CF₃)₂HGe-Cp)(NEt₂)₃); (bis(trifluoromethyl)germyl)cyclopentadienyl tris(ethylamino) Zirconium(IV) (Zr((CF₃)₂ HGe-Cp)(NHEt)₃); (bis(trifluoromethyl)germyl)cyclopentadienyl tris(Ethylmethylamino) Zirconium(IV) (Zr((CF₃)₂HGe-Cp)(NEtMe)₃); (bis(trifluoromethyl)germyl)cyclopentadienyl tris(Di n-propylamino) Zirconium (IV) (Zr((CF₃)₂HGe-Cp)(NnPr₂)₃); (bis(trifluoromethyl)germyl)cyclopentadienyl tris(n-propylamino) Zirconium (IV) (Zr((CF₃)₂HGe-Cp)(NHnPr)₃); (bis(trifluoromethyl)germyl)cyclopentadienyl tris(Diisopropylamino) Zirconium (IV) (Zr((CF₃)₂HGe-Cp)(NiPr₂)₃); (bis(trifluoromethyl)germyl)cyclopentadienyl tris(isopropylamino) Zirconium (IV) (Zr((CF₃)₂HGe-Cp)(NHiPr)₃); (bis(trifluoromethyl)germyl)cyclopentadienyl tris(Di n-butylamino) Zirconium (IV) (Zr((CF₃)₂HGe-Cp)(NnBu₂)₃); (bis(trifluoromethyl)germyl)cyclopentadienyl tris(n-butylamino) Zirconium(IV) (Zr((CF₃)₂HGe-Cp)(NHnBu)₃); (bis(trifluoromethyl)germyl)cyclopentadienyl tris(Di isobutylamino) Zirconium(IV) (Zr((CF₃)₂HGe-Cp)(NiBu₂)₃); (bis(trifluoromethyl)germyl)cyclopentadienyl tris(isobutylamino) Zirconium(IV) (Zr((CF₃)₂HGe-Cp)(NHiBu)₃); (bis(trifluoromethyl)germyl)cyclopentadienyl tris(Di sec-butylamino) Zirconium(IV) (Zr((CF₃)₂HGe-Cp)(NsBu₂)₃); (bis(trifluoromethyl)germyl)cyclopentadienyl tris(sec-butylamino) Zirconium(IV) (Zr((CF₃)₂HGe-Cp)(NHsBu)₃); (bis(trifluoromethyl)germyl)cyclopentadienyl tris(Di tert-butylamino) Zirconium(IV) (Zr((CF₃)₂HGe-Cp)(NtBu₂)₃); (bis(trifluoromethyl)germyl)cyclopentadienyl tris(tert-butylamino) Zirconium(IV) (Zr((CF₃)₂HGe-Cp)(NHtBu)₃); ((trifluoromethyl)dimethylgermyl)cyclopentadienyl tris(Dimethylamino) Zirconium(IV) (Zr((CF₃)Me₂Ge-Cp)(NMe₂)₃); ((trifluoromethyl)dimethylgermyl)cyclopentadienyl tris(methylamino) Zirconium(IV) (Zr((CF₃)Me₂Ge-Cp)(NHMe)₃); ((trifluoromethyl)dimethylgermyl)cyclopentadienyl tris(Diethylamino) Zirconium (IV) (Zr((CF₃)Me₂Ge-Cp)(NEt₂)₃); ((trifluoromethyl)dimethylgermyl)cyclopentadienyl tris(ethylamino) Zirconium (IV) (Zr((CF₃)Me₂Ge-Cp)(NHEt)₃); ((trifluoromethyl) dimethylgermyl)cyclopentadienyl tris(Ethylmethylamino) Zirconium(IV) (Zr((CF₃)Me₂Ge-Cp)(NEtMe)₃); ((trifluoromethyl)dimethylgermyl)cyclopentadienyl tris(Di n-propylamino)Zirconium(IV) (Zr((CF₃)Me₂Ge-Cp)(NnPr₂)₃); ((trifluoromethyl)dimethylgermyl)cyclopentadienyl tris(n-propylamino) Zirconium(IV) (Zr((CF₃)Me₂Ge-Cp)(NHnPr)₃); ((trifluoromethyl)dimethylgermyl)cyclopentadienyl tris(Di isopropylamino)Zirconium(IV) (Zr ((CF₃)Me₂Ge-Cp)(NiPr₂)₃); ((trifluoromethyl)dimethylgermyl)cyclopentadienyl tris(isopropylamino) Zirconium(IV) (Zr((CF₃)Me₂Ge-Cp)(NHiPr)₃); ((trifluoromethyl)dimethylgermyl)cyclopentadienyl tris(Di n-butylamino)Zirconium(IV) (Zr((CF₃)Me₂Ge-Cp)(NnBu₂)₃); ((trifluoromethyl)dimethylgermyl)cyclopentadienyl tris(n-butylamino) Zirconium(IV) (Zr((CF₃)Me₂Ge-Cp)(NHnBu)₃); ((trifluoromethyl)dimethylgermyl)cyclopentadienyl tris(Di isobutylamino)Zirconium(IV) (Zr((CF₃)Me₂Ge-Cp)(NiBu₂)₃); ((trifluoromethyl)dimethylgermyl)cyclopentadienyl tris(isobutylamino) Zirconium(IV) (Zr((CF₃)Me₂Ge-Cp)(NHiBu)₃); ((trifluoromethyl)dimethylgermyl)cyclopentadienyl tris(Di sec-butylamino) Zirconium(IV) (Zr((CF₃)Me₂Ge-Cp)(NsBu₂)₃); ((trifluoromethyl)dimethylgermyl)cyclopentadienyl tris (sec-butylamino) Zirconium(IV) (Zr((CF₃)Me₂Ge-Cp)(NHsBu)₃); ((trifluoromethyl)dimethylgermyl)cyclopentadienyl tris(Di tert-butylamino)Zirconium(IV) (Zr((CF₃)Me₂Ge-Cp)(NtBu₂)₃); and ((trifluoromethyl)dimethylgermyl)cyclopentadienyl tris(tert-butylamino) Zirconium(IV) (Zr((CF₃)Me₂Ge-Cp)(NHtBu)₃).

4. The Germanium- and Zirconium-film forming composition of claim 3, wherein the precursor is (trimethylgermyl)cyclopentadienyl tris(dimethylamino)Zirconium(IV) [Zr(TMG-Cp)(NMe₂)₃].

5. The Germanium- and Zirconium-film forming composition of claim 1, having the Formula II:

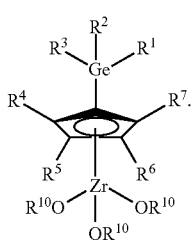

Formula II

6. The Germanium- and Zirconium-film forming composition of claim 5, wherein the precursor is selected from the group consisting of: (trimethylgermyl)cyclopentadienyl tris(methoxy)Zirconium(IV) (Zr(TMG-Cp)(OMe)₃); (trimethylgermyl)cyclopentadienyl tris(ethoxy)Zirconium(IV) (Zr(TMG-Cp)(OEt)₃); (trimethylgermyl)cyclopentadienyl tris(n-propoxy) Zirconium(IV) (Zr(TMG-Cp)(OnPr)₃); (trimethylgermyl)cyclopentadienyl tris(isopropoxy)Zirconium(IV) (Zr(TMG-Cp)(OiPr)₃); (trimethylgermyl)cyclopentadienyl tris(tert-butoxy)Zirconium(IV) (Zr(TMG-Cp)(OtBu)₃); (trimethylgermyl)cyclopentadienyl tris(sec-butoxy) Zirconium(IV) (Zr(TMG-Cp)(OsBu)₃); (trimethylgermyl)cyclopentadienyl tris(n-butoxy)Zirconium(IV) (Zr(TMG-Cp)(OnBu)₃); (trimethylgermyl)cyclopentadienyl tris(iso-butoxy)Zirconium(IV) (Zr(TMG-Cp)(OiBu)₃); (dimethylgermyl)cyclopentadienyl tris(methoxy) Zirconium(IV) (Zr(DMG-Cp)(OMe)₃); (dimethylgermyl)cyclopentadienyl tris(ethoxy) Zirconium(IV) (Zr(DMG-Cp)(OEt)₃); (dimethylgermyl)cyclopentadienyl tris(n-propoxy) Zirconium(IV) (Zr(DMG-Cp)(OnPr)₃); (dimethylgermyl)cyclopentadienyl tris(isopropoxy)Zirconium(IV) (Zr(DMG-Cp)(OiPr)₃); (dimethylgermyl)cyclopentadienyl tris(tert-butoxy) Zirconium(IV) (Zr(DM G-Cp)(OtBu)₃); (dimethylgermyl)cyclopentadienyl tris(sec-butoxy)Zirconium(IV) (Zr(DMG-Cp)(OsBu)₃); (dimethylgermyl)cyclopentadienyl tris(n-butoxy)Zirconium(IV) (Zr(DMG-Cp)(OnBu)₃); (dimethylgermyl)cyclopentadienyl tris (isobutoxy) Zirconium(IV) (Zr(DM G-Cp)(OiBu)₃); (trifluorogermyl)cyclopentadienyl tris(methoxy)Zirconium (IV) (Zr(F₃Ge-Cp)(OMe)₃); (trifluorogermyl)cyclopentadienyl tris(ethoxy)Zirconium(IV) (Zr(F₃Ge-Cp)(OEt)₃); (trifluorogermyl)cyclopentadienyl tris(n-propoxy)Zirconium (IV) (Zr(F₃Ge-Cp)(OnPr)₃); (trifluorogermyl)cyclopentadienyl tris(isopropoxy) Zirconium(IV) (Zr(F₃Ge-Cp)(OiPr)₃); (trifluorogermyl)cyclopentadienyl tris(tert-butoxy)Zirconium(IV) (Zr(F₃Ge-Cp)(OtBu)₃); (trifluorogermyl)cyclopentadienyl tris(sec-butoxy)Zirconium(IV) (Zr(F₃Ge-Cp)(OsBu)₃); (trifluorogermyl)cyclopentadienyl tris(n-butoxy)Zirconium(IV) (Zr(F₃Ge-Cp)(OnBu)₃); (trifluorogermyl)cyclopentadienyl tris(isobutoxy) Zirconium(IV) (Zr(F₃Ge-Cp)(OiBu)₃); (difluorogermyl)cyclopentadienyl tris(methoxy)Zirconium(IV) (Zr(F₂HGe-Cp)(OMe)₃); (difluorogermyl)cyclopentadienyl tris(ethoxy)Zirconium(IV) (Zr(F₂HGe-Cp)(OEt)₃); (difluorogermyl)cyclopentadienyl tris(n-propoxy)Zirconium(IV) (Zr(F₂HGe-Cp)(OnPr)₃); (difluorogermyl)cyclopentadienyl tris (isopropoxy) Zirconium(IV) (Zr(F₂HGe-Cp)(OiPr)₃); (difluorogermyl)cyclopentadienyl tris(tert-butoxy)Zirconium(IV) (Zr(F₂HGe-Cp)(OtBu)₃); (difluorogermyl)cyclopentadienyl tris(sec-butoxy)Zirconium(IV) (Zr(F₂HGe-Cp)(OsBu)₃); (difluorogermyl)cyclopentadienyl tris(n-butoxy) Zirconium(IV) (Zr(F₂HGe-Cp)(OnBu)₃); (difluorogermyl)cyclopentadienyl tris(isobutoxy)Zirconium(IV) (Zr(F₂HGe-Cp)(OiBu)₃); (monofluorogermyl)cyclopentadienyl tris (methoxy)Zirconium(IV) (Zr(FH₂Ge-Cp)(OMe)₃); (monofluorogermyl)cyclopentadienyl tris(ethoxy)Zirconium(IV) (Zr(FH₂Ge-Cp)(OEt)₃); (monofluorogermyl)cyclopentadienyl tris(n-propoxy)Zirconium(IV) (Zr(FH₂Ge-Cp)(OnPr)₃); (monofluorogermyl)cyclopentadienyl tris (isopropoxy)Zirconium(IV) (Zr(FH₂Ge-Cp)(OiPr)₃); (monofluorogermyl)cyclopentadienyl tris(tert-butoxy)Zirconium(IV) (Zr(FH₂Ge-Cp)(OtBu)₃); (monofluorogermyl)cyclopentadienyl tris(sec-butoxy)Zirconium(IV) (Zr(FH₂Ge-Cp)(OsBu)₃); (monofluorogermyl)cyclopentadienyl tris(n-butoxy)Zirconium(IV) (Zr(FH₂Ge-Cp)(OnBu)₃); (monofluorogermyl)cyclopentadienyl tris (isobutoxy)Zirconium(IV) (Zr(FH₂Ge-Cp)(OiBu)₃); (fluoro dimethylgermyl)cyclopentadienyl tris(methoxy)Zirconium (IV) (Zr(FMe₂Ge-Cp)(OMe)₃); (fluoro dimethylgermyl)cyclopentadienyl tris(ethoxy)Zirconium(IV) (Zr(FMe₂Ge-Cp)(OEt)₃); (fluoro dimethylgermyl)cyclopentadienyl tris(n-propoxy)Zirconium(IV) (Zr(FMe₂Ge-Cp)(OnPr)₃); (fluoro dimethylgermyl)cyclopentadienyl tris(isopropoxy)Zirconium(IV) (Zr(FMe₂Ge-Cp)(OiPr)₃); (fluoro dimethylgermyl)cyclopentadienyl tris(tert-butoxy)Zirconium(IV) (Zr(FMe₂Ge-Cp)(OtBu)₃); (fluoro dimethylgermyl)cyclopentadienyl tris(sec-butoxy)Zirconium(IV) (Zr(FMe₂Ge-Cp)(OsBu)₃); (fluoro dimethylgermyl)cyclopentadienyl tris(n-butoxy)Zirconium(IV) (Zr(FMe₂Ge-Cp)(OnBu)₃); (fluoro dimethylgermyl)cyclopentadienyl tris(isobutoxy)Zirconium(IV) (Zr(FMe₂Ge-Cp)(OiBu)₃); (tris(trifluoromethyl)germyl)cyclopentadienyl tris(methoxy) Zirconium(IV) (Zr((CF₃)₃Ge-Cp)(OMe)₃); (tris(trifluoromethyl)germyl)cyclopentadienyl tris(ethoxy)Zirconium(IV) (Zr((CF₃)₃Ge-Cp)(OEt)₃); (tris(trifluoromethyl)germyl)cyclopentadienyl tris(n-propoxy) Zirconium(IV) (Zr((CF₃)₃Ge-Cp)(OnPr)₃); (tris(trifluoromethyl)germyl)cyclopentadienyl tris(isopropoxy) Zirconium(IV) (Zr((CF₃)₃Ge-Cp)(OiPr)₃); (tris(trifluoromethyl)germyl)cyclopentadienyl tris(tert-butoxy) Zirconium (IV) (Zr((CF₃)₃Ge-Cp)(OtBu)₃); (tris(trifluoromethyl)germyl)cyclopentadienyl tris(sec-butoxy) Zirconium(IV) (Zr((CF₃)₃Ge-Cp)(OsBu)₃); (tris(trifluoromethyl)germyl)cyclopentadienyl tris(n-butoxy) Zirconium(IV) (Zr ((CF$_3$)$_3$Ge-Cp)(OnBu)$_3$); (tris(trifluoromethyl)germyl) cyclopentadienyl tris(isobutoxy) Zirconium(IV) (Zr((CF$_3$)$_3$ Ge-Cp)(OiBu)$_3$); (bis(trifluoromethyl)germyl)cyclopentadienyl tris(methoxy) Zirconium(IV) (Zr((CF$_3$)$_2$ HGe-Cp) (OMe)$_3$); (bis(trifluoromethyl)germyl)cyclopentadienyl tris (ethoxy)Zirconium(IV) (Zr((CF$_3$)$_2$ HGe-CP)(OEt)$_3$); (bis (trifluoromethyl)germyl)cyclopentadienyl tris(n-propoxy) Zirconium(IV) (Zr((CF$_3$)$_2$ HGe-Cp)(OnPr)$_3$); (bis(trifluoromethyl)germyl)cyclopentadienyl tris(isopropoxy) Zirconium(IV) (Zr((CF$_3$)$_2$HGe-Cp)(OiPr)$_3$); (bis(trifluoromethyl) germyl)cyclopentadienyl tris(tert-butoxy) Zirconium(IV) (Zr((CF$_3$)$_2$HGe-Cp)(OtBu)$_3$); (bis(trifluoromethyl)germyl) cyclopentadienyl tris(sec-butoxy) Zirconium(IV) (Zr((CF$_3$)$_2$ HGe-Cp)(OsBu)$_3$); (bis(trifluoromethyl)germyl)cyclopentadienyl tris(n-butoxy) Zirconium(IV) (Zr((CF$_3$)$_2$HGe-Cp) (OnBu)$_3$); (bis(trifluoromethyl)germyl)cyclopentadienyl tris (iso-butoxy) Zirconium(IV) (Zr((CF$_3$)$_2$HGe-Cp)(OiBu)$_3$); ((trifluoromethyl)dimethylgermyl)cyclopentadienyl tris (methoxy) Zirconium(IV) (Zr((CF$_3$)Me$_2$Ge-Cp)(OMe)$_3$); ((trifluoromethyl)dimethylgermyl)cyclopentadienyl tris (ethoxy) Zirconium(IV) (Zr((CF$_3$)Me$_2$Ge-Cp)(OEt)$_3$); ((trifluoromethyl)dimethylgermyl)cyclopentadienyl tris(n-propoxy) Zirconium(IV) (Zr((CF$_3$)Me$_2$Ge-Cp)(OnPr)$_3$); ((trifluoromethyl)dimethylgermyl)cyclopentadienyl tris(iso-propoxy) Zirconium(IV) (Zr((CF$_3$)Me$_2$Ge-Cp)(OiPr)$_3$); ((trifluoromethyl)dimethylgermyl)cyclopentadienyl tris (tert-butoxy) Zirconium(IV) (Zr((CF$_3$)Me$_2$Ge-Cp)(OtBu)$_3$); ((trifluoromethyl)dimethylgermyl)cyclopentadienyl tris (sec-butoxy) Zirconium(IV) (Zr((CF$_3$)Me$_2$Ge-Cp)(OsBu)$_3$); ((trifluoromethyl)dimethylgermyl)cyclopentadienyl tris(n-butoxy) Zirconium(IV) (Zr((CF$_3$)Me$_2$Ge-Cp)(OnBu)$_3$); and ((trifluoromethyl)dimethylgermyl)cyclopentadienyl tris (isobutoxy) Zirconium(IV) (Zr((CF$_3$)Me$_2$Ge-Cp)(OiBu)$_3$).

7. The Germanium- and Zirconium-film forming composition of claim 6, wherein the precursor is (trimethylgermyl) cyclopentadienyl tris(isopropoxy) Zirconium(IV) [Zr(TMG-Cp)(OiPr)$_3$].

8. The Germanium- and Zirconium-film forming composition of claim 1, the composition comprising between approximately 95% w/w and approximately 100% w/w of the precursor.

9. The Germanium- and Zirconium-film forming composition of claim 1, the composition comprising between approximately 0.0% w/w and approximately 5.0% w/w impurities.

10. The Germanium- and Zirconium-film forming composition of claim 9, the impurities including alcohol; alkylamines; dialkylamines; alkylimines; cyclopentadiene; dicyclopentadiene; alkylgermane; THF; ether; pentane; cyclohexane; heptane; benzene; toluene; chlorinated metal compounds; lithium, sodium, or potassium alkylamino; lithium, sodium, or potassium alkylakoxy; and/or lithium, sodium, or potassium cyclopentadienyl.

11. The Germanium- and Zirconium-film forming composition of claim 1, the composition comprising between approximately 0 ppbw and approximately 1 ppmw metal impurities.

12. The Germanium- and Zirconium-film forming composition of claim 11, the metal impurities including Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), and/or Zinc (Zn).

13. A process for the deposition of a Zirconium-containing film on a substrate, the process comprising the steps of: introducing a vapor of the Germanium- and Zirconium-containing precursor into a reactor having a substrate disposed therein and depositing at least part of the Germanium- and Zirconium-containing precursor onto the substrate, the precursor having one of the following formulae:

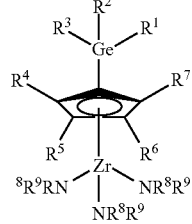

Formula I

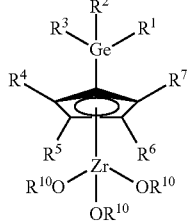

Formula II wherein each $R^1$, $R^2$, $R^3$, $R^4$, $R^5$, $R^6$, $R^7$, $R^8$, $R^9$ and $R^{10}$ is independently selected from the group consisting of H; a C1-C5 linear, branched, or cyclic alkyl group; and a C1-C5 linear, branched, or cyclic fluoroalkyl group.

14. The process of claim 13, wherein the Germanium- and Zirconium-containing precursor is selected from the group consisting of: (trimethylgermyl)cyclopentadienyl tris(Dimethylamino)Zirconium(IV) (Zr(TMG-Cp)(NMe$_2$)$_3$); (trimethylgermyl)cyclopentadienyl tris(methylamino) Zirconium (IV) (Zr(TMG-Cp)(NHMe)$_3$); (trimethylgermyl) cyclopentadienyl tris(Diethylamino)Zirconium(IV) (Zr (TMG-Cp)(NEt$_2$)$_3$); (trimethylgermyl)cyclopentadienyl tris (ethylamino)Zirconium(IV) (Zr(TMG-Cp)(NHEt)$_3$); (trimethylgermyl)cyclopentadienyl tris(ethylmethylamino) Zirconium(IV) (Zr(TMG-Cp)(NEtMe)$_3$); (trimethylgermyl) cyclopentadienyl tris(Di n-propylamino)Zirconium(IV) (Zr (TMG-Cp)(NnPr$_2$)$_3$); (trimethylgermyl)cyclopentadienyl tris(n-propylamino)Zirconium(IV) (Zr(TMG-Cp) (NHnPr)$_3$); (trimethylgermyl)cyclopentadienyl tris(Di isopropylamino)Zirconium(IV) (Zr(TMG-Cp)(NiPr$_2$)$_3$); (trimethylgermyl)cyclopentadienyl tris(isopropylamino)Zirconium(IV) (Zr(TMG-Cp)(NH iPr)$_3$); (trimethylgermyl) cyclopentadienyl tris(Di n-butylamino)Zirconium(IV) (Zr (TMG-Cp)(NnBu$_2$)$_3$); (trimethylgermyl)cyclopentadienyl tris(n-butylamino)Zirconium(IV) (Zr(TMG-Cp)(NHnBu)$_3$) (trimethylgermyl)cyclopentadienyl tris(Di isobutylamino) Zirconium(IV) (Zr(TMG-Cp)(NiBu$_2$)$_3$); (trimethylgermyl) cyclopentadienyl tris(isobutylamino)Zirconium(IV) (Zr (TMG-Cp)(NHiBu)$_3$); (trimethylgermyl)cyclopentadienyl tris(Di sec-butylamino)Zirconium(IV) (Zr(TMG-Cp) (NsBu$_2$)$_3$); (trimethylgermyl)cyclopentadienyl tris(sec-butylamino)Zirconium(IV) (Zr(TMG-Cp)(NHsBu)$_3$); (trimethylgermyl)cyclopentadienyl tris(Di tert-butylamino) Zirconium(IV) (Zr(TMG-Cp)(NtBu$_2$)$_3$); (trimethylgermyl) cyclopentadienyl tris(tert-butylamino)Zirconium(IV) (Zr (TMG-Cp)(NHtBu)$_3$); (dimethylgermyl)cyclopentadienyl tris(Dimethylamino)Zirconium(IV) (Zr(DMG-Cp)

(NMe₂)₃); (dimethylgermyl)cyclopentadienyl tris(methylamino)Zirconium(IV) (Zr(DMG-Cp)(NHMe)₃); (dimethylgermyl)cyclopentadienyl tris(Diethylamino)Zirconium(IV) (Zr(DMG-Cp)(NEt₂)₃); (dimethylgermyl)cyclopentadienyl tris(ethylamino)Zirconium(IV) (Zr(DMG-Cp)(NHEt)₃); (dimethylgermyl)cyclopentadienyl tris(ethylmethylamino) Zirconium(IV) (Zr(DMG-Cp)(NEtMe)₃); (dimethylgermyl)cyclopentadienyl tris(Di n-propylamino)Zirconium(IV) (Zr(DMG-Cp)(NnPr₂)₃); (dimethylgermyl)cyclopentadienyl tris(n-propylamino)Zirconium(IV) (Zr(DMG-Cp)(NHnPr)₃); (dimethylgermyl)cyclopentadienyl tris(Di isopropylamino)Zirconium(IV) (Zr(DMG-Cp)(NiPr₂)₃); (dimethylgermyl)cyclopentadienyl tris(isopropylamino)Zirconium(IV) (Zr(DMG-Cp)(NH iPr)₃); (dimethylgermyl)cyclopentadienyl tris(Di n-butylamino)Zirconium(IV) (Zr(DMG-Cp)(NnBu₂)₃); (dimethylgermyl)cyclopentadienyl tris(n-butylamino)Zirconium(IV) (Zr(DMG-Cp)(NHnBu)₃); (dimethylgermyl)cyclopentadienyl tris(Di isobutylamino)Zirconium(IV) (Zr(DMG-Cp)(NiBu₂)₃); (dimethylgermyl)cyclopentadienyl tris(isobutylamino)Zirconium(IV) (Zr(DMG-Cp)(NHiBu)₃); (dimethylgermyl)cyclopentadienyl tris(Di sec-butylamino)Zirconium(IV) (Zr(DMG-Cp)(NsBu₂)₃); (dimethylgermyl)cyclopentadienyl tris(sec-butylamino)Zirconium(IV) (Zr(DMG-Cp)(NHsBu)₃); (dimethylgermyl)cyclopentadienyl tris(Di tert-butylamino)Zirconium(IV) (Zr(DMG-Cp)(NtBu₂)₃); (dimethylgermyl)cyclopentadienyl tris(tert-butylamino)Zirconium(IV) (Zr(DMG-Cp)(NHtBu)₃); (trifluorogermyl)cyclopentadienyl tris(Dimethylamino)Zirconium(IV) (Zr(F₃Ge-Cp)(NMe₂)₃); (trifluorogermyl)cyclopentadienyl tris(methylamino)Zirconium(IV) (Zr(F₃Ge-Cp)(NHMe)₃); (trifluorogermyl)cyclopentadienyl tris(Diethylamino) Zirconium(IV) (Zr(F₃Ge-Cp)(NEt₂)₃); (trifluorogermyl)cyclopentadienyl tris(ethylamino)Zirconium(IV) (Zr(F₃Ge-Cp)(NHEt)₃); (trifluorogermyl)cyclopentadienyl tris(Ethylmethylamino)Zirconium(IV) (Zr(F₃Ge-Cp)(NEtMe)₃); (trifluorogermyl)cyclopentadienyl tris(Di n-propylamino)Zirconium(IV) (Zr(F₃Ge-Cp)(NnPr₂)₃); (trifluorogermyl)cyclopentadienyl tris(n-propylamino)Zirconium(IV) (Zr(F₃Ge-Cp)(NHnPr)₃) (trifluorogermyl)cyclopentadienyl tris(Di isopropylamino)Zirconium(IV) (Zr(F₃Ge-Cp)(NiPr₂)₃); (trifluorogermyl)cyclopentadienyl tris(isopropylamino)Zirconium(IV) (Zr(F₃Ge-Cp)(NHiPr)₃); (trifluorogermyl)cyclopentadienyl tris(Di n-butylamino)Zirconium(IV) (Zr(F₃Ge-Cp)(NnBu₂)₃); (trifluorogermyl)cyclopentadienyl tris(n-butylamino)Zirconium(IV) (Zr(F₃Ge-Cp)(NHnBu)₃); (trifluorogermyl)cyclopentadienyl tris(Di isobutylamino)Zirconium(IV) (Zr(F₃Ge-Cp)(NiBu₂)₃); (trifluorogermyl)cyclopentadienyl tris(isobutylamino)Zirconium(IV) (Zr(F₃Ge-Cp)(NHiBu)₃); (trifluorogermyl)cyclopentadienyl tris(Di sec-butylamino)Zirconium(IV) (Zr(F₃Ge-Cp)(NsBu₂)₃); (trifluorogermyl)cyclopentadienyl tris(sec-butylamino)Zirconium(IV) (Zr(F₃Ge-Cp)(NHsBu)₃); (trifluorogermyl)cyclopentadienyl tris(Di tert-butylamino)Zirconium(IV) (Zr(F₃Ge-Cp)(NtBu₂)₃); (trifluorogermyl)cyclopentadienyl tris(tert-butylamino)Zirconium(IV) (Zr(F₃Ge-Cp)(NHtBu)₃); (difluorogermyl)cyclopentadienyl tris(Dimethylamino)Zirconium(IV) (Zr(F₂HGe-Cp)(NMe₂)₃); (difluorogermyl)cyclopentadienyl tris(methylamino)Zirconium(IV) (Zr(F₂HGe-Cp)(NHMe)₃); (difluorogermyl)cyclopentadienyl tris(Diethylamino)Zirconium(IV) (Zr(F₂HGe-Cp)(NEt₂)₃); (difluorogermyl)cyclopentadienyl tris(ethylamino)Zirconium(IV) (Zr(F₂HGe-Cp)(NHEt)₃); (difluorogermyl)cyclopentadienyl tris(Ethylmethylamino) Zirconium(IV) (Zr(F₂HGe-Cp)(NEtMe)₃); (difluorogermyl)cyclopentadienyl tris(Di n-propylamino)Zirconium(IV) (Zr(F₂HGe-Cp)(NnPr₂)₃); (difluorogermyl)cyclopentadienyl tris(n-propylamino)Zirconium(IV) (Zr(F₂HGe-Cp)(NHnPr)₃); (difluorogermyl)cyclopentadienyl tris(Di isopropylamino)Zirconium(IV) (Zr(F₂HGe-Cp)(NiPr₂)₃); (difluorogermyl)cyclopentadienyl tris(isopropylamino)Zirconium(IV) (Zr(F₂HGe-Cp)(NH iPr)₃); (difluorogermyl)cyclopentadienyl tris(Di n-butylamino)Zirconium(IV) (Zr(F₂HGe-Cp)(NnBu₂)₃); (difluorogermyl)cyclopentadienyl tris(n-butylamino)Zirconium(IV) (Zr(F₂HGe-Cp)(NHnBu)₃); (difluorogermyl)cyclopentadienyl tris(Di isobutylamino)Zirconium(IV) (Zr(F₂HGe-Cp)(NiBu₂)₃); (difluorogermyl)cyclopentadienyl tris(isobutylamino)Zirconium(IV) (Zr(F₂HGe-Cp)(NHiBu)₃); (difluorogermyl)cyclopentadienyl tris(Di sec-butylamino)Zirconium(IV) (Zr(F₂HGe-Cp)(NsBu₂)₃); (difluorogermyl)cyclopentadienyl tris(sec-butylamino)Zirconium(IV) (Zr(F₂HGe-Cp)(NHsBu)₃); (difluorogermyl)cyclopentadienyl tris(Di tert-butylamino)Zirconium(IV) (Zr(F₂HGe-Cp)(NtBu₂)₃); (difluorogermyl)cyclopentadienyl tris(tert-butylamino)Zirconium(IV) (Zr(F₂HGe-Cp)(NHtBu)₃); (monofluorogermyl)cyclopentadienyl tris(Dimethylamino)Zirconium(IV) (Zr(FH₂Ge-Cp)(NMe₂)₃); (monofluorogermyl)cyclopentadienyl tris(methylamino)Zirconium(IV) (Zr(FH₂Ge-Cp)(NHMe)₃); (monofluorogermyl)cyclopentadienyl tris(Diethylamino)Zirconium(IV) (Zr(FH₂Ge-Cp)(NEt₂)₃); (monofluorogermyl)cyclopentadienyl tris(ethylamino)Zirconium(IV) (Zr(FH₂Ge-Cp)(NHEO)₃); (monofluorogermyl)cyclopentadienyl tris(Ethylmethylamino)Zirconium(IV) (Zr(FH₂Ge-Cp)(NEtMe)₃); (monofluorogermyl)cyclopentadienyl tris(Di n-propylamino)Zirconium(IV) (Zr(FH₂Ge-Cp)(NnPr₂)₃); (monofluorogermyl)cyclopentadienyl tris(n-propylamino)Zirconium(IV) (Zr(FH₂Ge-Cp)(NHnPr)₃); (monofluorogermyl)cyclopentadienyl tris(Diisopropylamino)Zirconium(IV) (Zr(FH₂Ge-Cp)(NiPr₂)₃); (monofluorogermyl)cyclopentadienyl tris(isopropylamino)Zirconium(IV) (Zr(FH₂Ge-Cp)(NHiPr)₃); (monofluorogermyl)cyclopentadienyl tris(Di n-butylamino)Zirconium(IV) (Zr(FH₂Ge-Cp)(NnBu₂)₃); (monofluorogermyl)cyclopentadienyl tris(n-butylamino)Zirconium(IV) (Zr(FH₂Ge-Cp)(NHnBu)₃); (monofluorogermyl)cyclopentadienyl tris(Di isobutylamino)Zirconium(IV) (Zr(FH₂Ge-Cp)(NiBu₂)₃) (monofluorogermyl)cyclopentadienyl tris(isobutylamino)Zirconium(IV) (Zr(FH₂Ge-Cp)(NHiBu)₃); (monofluorogermyl)cyclopentadienyl tris(Di sec-butylamino)Zirconium(IV) (Zr(FH₂Ge-Cp)(NsBu₂)₃); (monofluorogermyl)cyclopentadienyl tris(sec-butylamino)Zirconium(IV) (Zr(FH₂Ge-Cp)(NHsBO₃)); (monofluorogermyl)cyclopentadienyl tris(Di tert-butylamino)Zirconium(IV) (Zr(FH₂Ge-Cp)(NtBu₂)₃); (monofluorogermyl)cyclopentadienyl tris(tert-butylamino)Zirconium(IV) (Zr(FH₂Ge-Cp)(NHtBu)₃); (fluoro dimethylgermyl)cyclopentadienyl tris(Dimethylamino) Zirconium(IV) (Zr(FMe₂Ge-Cp)(NMe₂)₃); (fluoro dimethylgermyl)cyclopentadienyl tris(methylamino)Zirconium(IV) (Zr(FMe₂Ge-Cp)(NHMe)₃); (fluoro dimethylgermyl)cyclopentadienyl tris(Diethylamino)Zirconium(IV) (Zr(FMe₂Ge-Cp)(NEt₂)₃); (fluoro dimethylgermyl)cyclopentadienyl tris(ethylamino)Zirconium(IV) (Zr(FMe₂Ge-Cp)(NHEt)₃); (fluoro dimethylgermyl)cyclopentadienyl tris(Ethylmethylamino)Zirconium(IV) (Zr(FMe₂Ge-Cp)(NEtMe)₃); (fluoro dimethylgermyl)cyclopentadienyl tris(Di n-propylamino) Zirconium(IV) (Zr(FMe₂Ge-Cp)(NnPr₂)₃); (fluoro dimethylgermyl)cyclopentadienyl tris(n-propylamino)Zirconium(IV) (Zr(FMe₂Ge-Cp)(NHnPr)₃); (fluoro dimethylgermyl)cyclopentadienyl tris(Diisopropylamino)Zirconium(IV) (Zr (FMe$_2$Ge-Cp)(NiPr$_2$)$_3$); (fluoro dimethylgermyl)cyclopentadienyl tris(isopropylamino) Zirconium(IV) (Zr(FMe$_2$Ge-Cp)(NHiPr)$_3$); (fluoro dimethylgermyl)cyclopentadienyl tris (Di n-butylamino)Zirconium(IV) (Zr(FMe$_2$Ge-Cp)(NnBu$_2$)$_3$); (fluoro dimethylgermyl)cyclopentadienyl tris(n-butylamino)Zirconium(IV) (Zr(FMe$_2$Ge-Cp)(NHnBu)$_3$); (fluoro dimethylgermyl)cyclopentadienyl tris(Di isobutylamino)Zirconium(IV) (Zr(FMe$_2$Ge-Cp)(NiBu$_2$)$_3$); (fluoro dimethylgermyl)cyclopentadienyl tris(isobutylamino) Zirconium(IV) (Zr(FMe$_2$Ge-Cp)(NHiBu)$_3$); (fluoro dimethylgermyl)cyclopentadienyl tris(Di sec-butylamino) Zirconium (IV) (Zr(FMe$_2$Ge-Cp)(NsBu$_2$)$_3$); (fluoro dimethylgermyl) cyclopentadienyl tris(sec-butylamino)Zirconium(IV) (Zr (FMe$_2$Ge-Cp)(NHsBu)$_3$); (fluoro dimethylgermyl) cyclopentadienyl tris(Di tert-butylamino)Zirconium(IV) (Zr (FMe$_2$Ge-Cp)(NtBu$_2$)$_3$); (fluoro dimethylgermyl) cyclopentadienyl tris(tert-butylamino) Zirconium(IV) (Zr (FMe$_2$Ge-Cp)(NHtBu)$_3$); (tris(trifluoromethyl)germyl) cyclopentadienyl tris(Dimethylamino) Zirconium(IV) (Zr ((CF$_3$)$_3$Ge-Cp)(NMe$_2$)$_3$); (tris(trifluoromethyl)germyl) cyclopentadienyl tris(methylamino) Zirconium(IV) (Zr ((CF$_3$)$_3$Ge-Cp)(NHMe)$_3$); (tris(trifluoromethyl)germyl) cyclopentadienyl tris(Diethylamino) Zirconium(IV) (Zr ((CF$_3$)$_3$Ge-Cp)(NEt$_2$)$_3$); (tris(trifluoromethyl)germyl) cyclopentadienyl tris(ethylamino) Zirconium(IV) (Zr ((CF$_3$)$_3$ Ge-Cp)(NHEt)$_3$); (tris(trifluoromethyl)germyl) cyclopentadienyl tris(Ethylmethylamino) Zirconium(IV) (Zr((CF$_3$)$_3$Ge-Cp)(NEtMe)$_3$); (tris(trifluoromethyl)germyl) cyclopentadienyl tris(Di n-propylamino) Zirconium(IV) (Zr ((CF$_3$)$_3$Ge-Cp)(NnPr$_2$)$_3$); (tris(trifluoromethyl)germyl)cyclopentadienyl tris(n-propylamino) Zirconium(IV) (Zr ((CF$_3$)$_3$Ge-Cp)(NHnPr)$_3$); (tris(trifluoromethyl)germyl) cyclopentadienyl tris(Diisopropylamino) Zirconium(IV) (Zr ((CF$_3$)$_3$Ge-Cp)(NiPr$_2$)$_3$); (tris(trifluoromethyl)germyl) cyclopentadienyl tris(isopropylamino) Zirconium(IV) (Zr ((CF$_3$)$_3$Ge-Cp)(NHiPr)$_3$); (tris(trifluoromethyl)germyl) cyclopentadienyl tris(Di n-butylamino) Zirconium(IV) (Zr ((CF$_3$)$_3$Ge-Cp)(NnBu$_2$)$_3$); (tris(trifluoromethyl)germyl) cyclopentadienyl tris(n-butylamino) Zirconium(IV) (Zr ((CF$_3$)$_3$Ge-Cp)(NHnBu)$_3$); (tris(trifluoromethyl)germyl) cyclopentadienyl tris(Di isobutylamino) Zirconium(IV) (Zr ((CF$_3$)$_3$Ge-Cp)(NiBu$_2$)$_3$); (tris(trifluoromethyl)germyl) cyclopentadienyl tris(isobutylamino) Zirconium(IV) (Zr ((CF$_3$)$_3$Ge-Cp)(NHiBu)$_3$); (tris(trifluoromethyl)germyl) cyclopentadienyl tris(Di sec-butylamino) Zirconium(IV) (Zr ((CF$_3$)$_3$Ge-Cp)(NsBu$_2$)$_3$); (tris(trifluoromethyl)germyl) cyclopentadienyl tris(sec-butylamino) Zirconium(IV) (Zr ((CF$_3$)$_3$Ge-Cp)(NHsBu)$_3$); (tris(trifluoromethyl)germyl) cyclopentadienyl tris(Di tert-butylamino) Zirconium(IV) (Zr((CF$_3$)$_3$Ge-Cp)(NtBu$_2$)$_3$); (tris(trifluoromethyl)germyl) cyclopentadienyl tris(tert-butylamino) Zirconium(IV) (Zr ((CF$_3$)$_3$Ge-Cp)(NHtBu)$_3$); (bis(trifluoromethyl)germyl)cyclopentadienyl tris(Dimethylamino) Zirconium(IV) (Zr ((CF$_3$)$_2$HGe-Cp)(NMe$_2$)$_3$); (bis(trifluoromethyl)germyl) cyclopentadienyl tris(methylamino) Zirconium(IV) (Zr ((CF$_3$)$_2$HGe-Cp)(NHMe)$_3$); (bis(trifluoromethyl)germyl) cyclopentadienyl tris(Diethylamino) Zirconium(IV) (Zr ((CF$_3$)$_2$HGe-Cp)(NEt$_2$)$_3$); (bis(trifluoromethyl)germyl) cyclopentadienyl tris(ethylamino) Zirconium(IV) (Zr ((CF$_3$)$_2$ HGe-Cp)(NHEt)$_3$); (bis(trifluoromethyl)germyl) cyclopentadienyl tris(Ethylmethylamino) Zirconium(IV) (Zr((CF$_3$)$_2$HGe-Cp)(NEtMe)$_3$); (bis(trifluoromethyl)germyl) cyclopentadienyl tris(Di n-propylamino) Zirconium (IV) (Zr((CF$_3$)$_2$HGe-Cp)(NnPr$_2$)$_3$); (bis(trifluoromethyl) germyl)cyclopentadienyl tris(n-propylamino) Zirconium (IV) (Zr((CF$_3$)$_2$HGe-Cp)(NHnPr)$_3$); (bis(trifluoromethyl) germyl)cyclopentadienyl tris(Diisopropylamino) Zirconium (IV) (Zr((CF$_3$)$_2$HGe-Cp)(NiPr$_2$)$_3$); (bis(trifluoromethyl) germyl)cyclopentadienyl tris(isopropylamino) Zirconium (IV) (Zr((CF$_3$)$_2$HGe-Cp)(NHiPr)$_3$); (bis(trifluoromethyl) germyl)cyclopentadienyl tris(Di n-butylamino) Zirconium (IV) (Zr((CF$_3$)$_2$HGe-Cp)(NnBu$_2$)$_3$); (bis(trifluoromethyl) germyl)cyclopentadienyl tris(n-butylamino) Zirconium(IV) (Zr((CF$_3$)$_2$HGe-Cp)(NHnBu)$_3$); (bis(trifluoromethyl)germyl)cyclopentadienyl tris(Di isobutylamino) Zirconium(IV) (Zr((CF$_3$)$_2$HGe-Cp)(NiBu$_2$)$_3$); (bis(trifluoromethyl)germyl) cyclopentadienyl tris(isobutylamino) Zirconium(IV) (Zr ((CF$_3$)$_2$HGe-Cp)(NHiBu)$_3$); (bis(trifluoromethyl)germyl) cyclopentadienyl tris(Di sec-butylamino) Zirconium(IV) (Zr ((CF$_3$)$_2$HGe-Cp)(NsBu$_2$)$_3$); (bis(trifluoromethyl)germyl) cyclopentadienyl tris(sec-butylamino) Zirconium(IV) (Zr ((CF$_3$)$_2$HGe-Cp)(NHsBu)$_3$); (bis(trifluoromethyl)germyl) cyclopentadienyl tris(Di tert-butylamino) Zirconium(IV) (Zr((CF$_3$)$_2$HGe-Cp)(NtBu$_2$)$_3$); (bis(trifluoromethyl)germyl) cyclopentadienyl tris(tert-butylamino) Zirconium(IV) (Zr ((CF$_3$)$_2$HGe-Cp)(NHtBu)$_3$); ((trifluoromethyl)dimethylgermyl)cyclopentadienyl tris(Dimethylamino) Zirconium(IV) (Zr((CF$_3$)Me$_2$Ge-Cp)(NMe$_2$)$_3$); ((trifluoromethyl)dimethylgermyl)cyclopentadienyl tris(methylamino) Zirconium(IV) (Zr((CF$_3$)Me$_2$Ge-Cp)(NHMe)$_3$); ((trifluoromethyl)dimethylgermyl)cyclopentadienyl tris(Diethylamino) Zirconium (IV) (Zr((CF$_3$)Me$_2$Ge-Cp)(NEt$_2$)$_3$); ((trifluoromethyl)dimethylgermyl)cyclopentadienyl tris(ethylamino) Zirconium (IV) (Zr((CF$_3$)Me$_2$Ge-Cp)(NHEt)$_3$); ((trifluoromethyl) dimethylgermyl)cyclopentadienyl tris(Ethylmethylamino) Zirconium(IV) (Zr((CF$_3$)Me$_2$Ge-Cp)(NEtMe)$_3$); ((trifluoromethyl)dimethylgermyl)cyclopentadienyl tris(Di n-propylamino)Zirconium(IV) (Zr((CF$_3$)Me$_2$Ge-Cp) (NnPr$_2$)$_3$); ((trifluoromethyl)dimethylgermyl)cyclopentadienyl tris(n-propylamino) Zirconium(IV) (Zr((CF$_3$)Me$_2$Ge-Cp)(NHnPr)$_3$); ((trifluoromethyl)dimethylgermyl) cyclopentadienyl tris(Di isopropylamino)Zirconium(IV) (Zr ((CF$_3$)Me$_2$Ge-Cp)(NiPr$_2$)$_3$); ((trifluoromethyl) dimethylgermyl)cyclopentadienyl tris(isopropylamino) Zirconium(IV) (Zr((CF$_3$)Me$_2$Ge-Cp)(NHiPr)$_3$); ((trifluoromethyl)dimethylgermyl)cyclopentadienyl tris(Di n-butylamino)Zirconium(IV) (Zr((CF$_3$)Me$_2$Ge-Cp)(NnBu$_2$)$_3$); ((trifluoromethyl)dimethylgermyl)cyclopentadienyl tris(n-butylamino) Zirconium(IV) (Zr((CF$_3$)Me$_2$Ge-Cp) (NHnBu)$_3$); ((trifluoromethyl)dimethylgermyl)cyclopentadienyl tris(Di isobutylamino)Zirconium(IV) (Zr((CF$_3$) Me$_2$Ge-Cp)(NiBu$_2$)$_3$); ((trifluoromethyl)dimethylgermyl) cyclopentadienyl tris(isobutylamino) Zirconium(IV) (Zr ((CF$_3$)Me$_2$Ge-Cp)(NHiBu)$_3$); ((trifluoromethyl) dimethylgermyl)cyclopentadienyl tris(Di sec-butylamino) Zirconium(IV) (Zr((CF$_3$)Me$_2$Ge-Cp)(NsBu$_2$)$_3$); ((trifluoromethyl)dimethylgermyl)cyclopentadienyl tris (sec-butylamino) Zirconium(IV) (Zr((CF$_3$)Me$_2$Ge-Cp) (NHsBu)$_3$); ((trifluoromethyl)dimethylgermyl)cyclopentadienyl tris(Di tert-butylamino)Zirconium(IV) (Zr((CF$_3$) Me$_2$Ge-Cp)(NtBu$_2$)$_3$); and ((trifluoromethyl) dimethylgermyl)cyclopentadienyl tris(tert-butylamino) Zirconium(IV) (Zr((CF$_3$)Me$_2$Ge-Cp)(NHtBu)$_3$).

15. The process of claim 13, wherein the Germanium- and Zirconium-containing precursor is selected from the group consisting of: (trimethylgermyl)cyclopentadienyl tris (methoxy)Zirconium(IV) (Zr(TMG-Cp)(OMe)$_3$); (trimethylgermyl)cyclopentadienyl tris(ethoxy)Zirconium(IV) (Zr (TMG-Cp)(OEt)$_3$); (trimethylgermyl)cyclopentadienyl tris (n-propoxy) Zirconium(IV) (Zr(TMG-Cp)(OnPr)$_3$); (trimethylgermyl)cyclopentadienyl tris(isopropoxy)Zirconium(IV) (Zr(TMG-Cp)(OiPr)$_3$); (trimethylgermyl)cyclopentadienyl tris(tert-butoxy)Zirconium(IV) (Zr(TMG-Cp) (OtBu)$_3$); (trimethylgermyl)cyclopentadienyl tris(sec-butoxy) Zirconium(IV) (Zr(TMG-Cp)(OsBu)$_3$); (trimethylgermyl)cyclopentadienyl tris(n-butoxy)Zirconium (IV) (Zr(TMG-Cp)(OnBu)$_3$); (trimethylgermyl)cyclopentadienyl tris(iso-butoxy)Zirconium(IV) (Zr(TMG-Cp)(OiBu)$_3$); (dimethylgermyl)cyclopentadienyl tris(methoxy) Zirconium(IV) (Zr(DMG-Cp)(OMe)$_3$); (dimethylgermyl)cyclopentadienyl tris(ethoxy) Zirconium(IV) (Zr(DMG-Cp)(OEt)$_3$); (dimethylgermyl)cyclopentadienyl tris(n-propoxy)Zirconium(IV) (Zr(DMG-Cp)(OnPr)$_3$); (dimethylgermyl)cyclopentadienyl tris(isopropoxy)Zirconium(IV) (Zr(DMG-Cp)(OiPr)$_3$); (dimethylgermyl)cyclopentadienyl tris(tert-butoxy) Zirconium(IV) (Zr(DMG-Cp)(OtBu)$_3$); (dimethylgermyl)cyclopentadienyl tris(sec-butoxy)Zirconium(IV) (Zr(DMG-Cp)(OsBu)$_3$); (dimethylgermyl)cyclopentadienyl tris(n-butoxy)Zirconium(IV) (Zr(DMG-Cp)(OnBu)$_3$); (dimethylgermyl)cyclopentadienyl tris (isobutoxy) Zirconium(IV) (Zr(DMG-Cp)(OiBu)$_3$); (trifluorogermyl)cyclopentadienyl tris(methoxy)Zirconium (IV) (Zr(F$_3$Ge-Cp)(OMe)$_3$); (trifluorogermyl)cyclopentadienyl tris(ethoxy)Zirconium(IV) (Zr(F$_3$Ge-Cp)(OEt)$_3$); (trifluorogermyl)cyclopentadienyl tris(n-propoxy)Zirconium (IV) (Zr(F$_3$Ge-Cp)(OnPr)$_3$); (trifluorogermyl)cyclopentadienyl tris(isopropoxy) Zirconium(IV) (Zr(F$_3$Ge-Cp)(OiPr)$_3$); (trifluorogermyl)cyclopentadienyl tris(tert-butoxy)Zirconium(IV) (Zr(F$_3$Ge-Cp)(OtBu)$_3$); (trifluorogermyl)cyclopentadienyl tris(sec-butoxy)Zirconium(IV) (Zr(F$_3$Ge-Cp)(OsBu)$_3$); (trifluorogermyl)cyclopentadienyl tris(n-butoxy)Zirconium(IV) (Zr(F$_3$Ge-Cp)(OnBu)$_3$); (trifluorogermyl)cyclopentadienyl tris(isobutoxy) Zirconium(IV) (Zr(F$_3$Ge-Cp)(OiBu)$_3$); (difluorogermyl)cyclopentadienyl tris(methoxy)Zirconium(IV) (Zr(F$_2$HGe-Cp)(OMe)$_3$); (difluorogermyl)cyclopentadienyl tris(ethoxy)Zirconium(IV) (Zr(F$_2$HGe-Cp)(OEt)$_3$); (difluorogermyl)cyclopentadienyl tris(n-propoxy)Zirconium(IV) (Zr(F$_2$HGe-Cp)(OnPr)$_3$); (difluorogermyl)cyclopentadienyl tris (isopropoxy) Zirconium(IV) (Zr(F$_2$HGe-Cp)(OiPr)$_3$); (difluorogermyl)cyclopentadienyl tris(tert-butoxy)Zirconium(IV) (Zr(F$_2$HGe-Cp)(OtBu)$_3$); (difluorogermyl)cyclopentadienyl tris(sec-butoxy)Zirconium(IV) (Zr(F$_2$HGe-Cp)(OsBu)$_3$); (difluorogermyl)cyclopentadienyl tris(n-butoxy) Zirconium(IV) (Zr(F$_2$HGe-Cp)(OnBu)$_3$); (difluorogermyl)cyclopentadienyl tris(isobutoxy)Zirconium(IV) (Zr(F$_2$HGe-Cp)(OiBu)$_3$); (monofluorogermyl)cyclopentadienyl tris (methoxy)Zirconium(IV) (Zr(FH$_2$Ge-Cp)(OMe)$_3$); (monofluorogermyl)cyclopentadienyl tris(ethoxy)Zirconium(IV) (Zr(FH$_2$Ge-Cp)(OEt)$_3$); (monofluorogermyl)cyclopentadienyl tris(n-propoxy)Zirconium(IV) (Zr(FH$_2$Ge-Cp)(OnPr)$_3$); (monofluorogermyl)cyclopentadienyl tris (isopropoxy)Zirconium(IV) (Zr(FH$_2$Ge-Cp)(OiPr)$_3$); (monofluorogermyl)cyclopentadienyl tris(tert-butoxy)Zirconium(IV) (Zr(FH$_2$Ge-Cp)(OtBu)$_3$); (monofluorogermyl)cyclopentadienyl tris(sec-butoxy)Zirconium(IV) (Zr(FH$_2$Ge-Cp)(OsBu)$_3$); (monofluorogermyl)cyclopentadienyl tris(n-butoxy)Zirconium(IV) (Zr(FH$_2$Ge-Cp)(OnBu)$_3$); (monofluorogermyl)cyclopentadienyl tris (isobutoxy)Zirconium(IV) (Zr(FH$_2$Ge-Cp)(OiBu)$_3$); (fluoro dimethylgermyl)cyclopentadienyl tris(methoxy)Zirconium (IV) (Zr(FMe$_2$Ge-Cp)(OMe)$_3$); (fluoro dimethylgermyl)cyclopentadienyl tris(ethoxy)Zirconium(IV) (Zr(FMe$_2$Ge-Cp)(OEt)$_3$); (fluoro dimethylgermyl)cyclopentadienyl tris(n-propoxy)Zirconium(IV) (Zr(FMe$_2$Ge-Cp)(OnPr)$_3$); (fluoro dimethylgermyl)cyclopentadienyl tris(isopropoxy)Zirconium(IV) (Zr(FMe$_2$Ge-Cp)(OiPr)$_3$); (fluoro dimethylgermyl)cyclopentadienyl tris(tert-butoxy)Zirconium(IV) (Zr(FMe$_2$Ge-Cp)(OtBu)$_3$); (fluoro dimethylgermyl)cyclopentadienyl tris(sec-butoxy)Zirconium(IV) (Zr(FMe$_2$Ge-Cp)(OsBu)$_3$); (fluoro dimethylgermyl)cyclopentadienyl tris(n-butoxy)Zirconium(IV) (Zr(FMe$_2$Ge-Cp)(OnBu)$_3$); (fluoro dimethylgermyl)cyclopentadienyl tris(isobutoxy)Zirconium(IV) (Zr(FMe$_2$Ge-Cp)(OiBu)$_3$); (tris(trifluoromethyl)germyl)cyclopentadienyl tris(methoxy) Zirconium(IV) (Zr((CF$_3$)$_3$Ge-Cp)(OMe)$_3$); (tris(trifluoromethyl)germyl)cyclopentadienyl tris(ethoxy)Zirconium(IV) (Zr((CF$_3$)$_3$Ge-Cp)(OEt)$_3$); (tris(trifluoromethyl)germyl)cyclopentadienyl tris(n-propoxy) Zirconium(IV) (Zr((CF$_3$)$_3$Ge-Cp)(OnPr)$_3$); (tris(trifluoromethyl)germyl)cyclopentadienyl tris(isopropoxy) Zirconium(IV) (Zr((CF$_3$)$_3$Ge-Cp)(OiPr)$_3$); (tris(trifluoromethyl)germyl)cyclopentadienyl tris(tert-butoxy) Zirconium (IV) (Zr((CF$_3$)$_3$Ge-Cp)(OtBu)$_3$); (tris(trifluoromethyl)germyl)cyclopentadienyl tris(sec-butoxy) Zirconium(IV) (Zr((CF$_3$)$_3$Ge-Cp)(OsBu)$_3$); (tris(trifluoromethyl)germyl)cyclopentadienyl tris(n-butoxy) Zirconium(IV) (Zr((CF$_3$)$_3$Ge-Cp)(OnBu)$_3$); (tris(trifluoromethyl)germyl)cyclopentadienyl tris(isobutoxy) Zirconium(IV) (Zr((CF$_3$)$_3$ Ge-Cp)(OiBu)$_3$); (bis(trifluoromethyl)germyl)cyclopentadienyl tris (methoxy) Zirconium(IV) (Zr((CF$_3$)$_2$ HGe-Cp)(OMe)$_3$); (bis(trifluoromethyl)germyl)cyclopentadienyl tris(ethoxy) Zirconium(IV) (Zr((CF$_3$)$_2$HGe-Cp)(OEt)$_3$); (bis(trifluoromethyl)germyl)cyclopentadienyl tris(n-propoxy) Zirconium (IV) (Zr((CF$_3$)$_2$HGe-Cp)(OnPr)$_3$); (bis(trifluoromethyl)germyl)cyclopentadienyl tris(isopropoxy) Zirconium(IV) (Zr((CF$_3$)$_2$HGe-Cp)(OiPr)$_3$); (bis(trifluoromethyl)germyl)cyclopentadienyl tris(tert-butoxy) Zirconium(IV) (Zr((CF$_3$)$_2$ HGe-Cp)(OtBu)$_3$); (bis(trifluoromethyl)germyl)cyclopentadienyl tris(sec-butoxy) Zirconium(IV) (Zr((CF$_3$)$_2$ HGe-Cp)(OsBu)$_3$); (bis(trifluoromethyl)germyl)cyclopentadienyl tris(n-butoxy) Zirconium(IV) (Zr((CF$_3$)$_2$HGe-Cp)(OnBu)$_3$); (bis(trifluoromethyl)germyl)cyclopentadienyl tris (iso-butoxy) Zirconium(IV) (Zr((CF$_3$)$_2$HGe-Cp)(OiBu)$_3$); ((trifluoromethyl)dimethylgermyl)cyclopentadienyl tris (methoxy) Zirconium(IV) (Zr((CF$_3$)Me$_2$Ge-Cp)(OMe)$_3$); ((trifluoromethyl)dimethylgermyl)cyclopentadienyl tris (ethoxy) Zirconium(IV) (Zr((CF$_3$)Me$_2$Ge-Cp)(OEt)$_3$); ((trifluoromethyl)dimethylgermyl)cyclopentadienyl tris(n-propoxy) Zirconium(IV) (Zr((CF$_3$)Me$_2$Ge-Cp)(OnPr)$_3$); ((trifluoromethyl)dimethylgermyl)cyclopentadienyl tris(isopropoxy) Zirconium(IV) (Zr((CF$_3$)Me$_2$Ge-Cp)(OiPr)$_3$); ((trifluoromethyl)dimethylgermyl)cyclopentadienyl tris (tert-butoxy) Zirconium(IV) (Zr((CF$_3$)Me$_2$Ge-Cp)(OtBu)$_3$); ((trifluoromethyl)dimethylgermyl)cyclopentadienyl tris (sec-butoxy) Zirconium(IV) (Zr((CF$_3$)Me$_2$Ge-Cp)(OsBu)$_3$); ((trifluoromethyl)dimethylgermyl)cyclopentadienyl tris(n-butoxy) Zirconium(IV) (Zr((CF$_3$)Me$_2$Ge-Cp)(OnBu)$_3$); and ((trifluoromethyl)dimethylgermyl)cyclopentadienyl tris (isobutoxy) Zirconium(IV) (Zr((CF$_3$)Me$_2$Ge-Cp)(OiBu)$_3$).

16. The process of claim 13, further comprising introducing at least one reactant into the reactor.

17. The process of claim 16, wherein the reactant is selected from the group consisting of H$_2$, H$_2$CO N$_2$H$_4$, NH$_3$, SiH$_4$, Si$_2$H$_6$, Si$_3$H$_8$, SiH$_2$Me$_2$, SiH$_2$Et$_2$, N(SiH$_3$)$_3$, hydrogen radicals thereof, and mixtures thereof.

18. The process of claim 16, wherein the reactant is selected from the group consisting of: O$_2$, O$_3$, H$_2$O, H$_2$O$_2$NO, N$_2$O, NO$_2$, oxygen radicals thereof, and mixtures thereof.

19. The process of claim 16, wherein the Germanium- and Zirconium-containing precursor and the reactant are introduced into the reactor simultaneously and the reactor is configured for chemical vapor deposition.

20. The process of claim 16, wherein the Germanium- and Zirconium-containing precursor and the reactant are introduced into the chamber sequentially and the reactor is configured for atomic layer deposition.

* * * * *